United States Patent
Hartwell et al.

(10) Patent No.: US 12,263,294 B2
(45) Date of Patent: Apr. 1, 2025

(54) SYSTEMS AND METHODS FOR OPERATING NEGATIVE PRESSURE WOUND THERAPY DEVICES

(71) Applicant: T.J.Smith and Nephew, Limited, Hull (GB)

(72) Inventors: Edward Yerbury Hartwell, Hull (GB); Felix Clarence Quintanar, Hull (GB); Johannes Dagevos van Rij, Cottingham (GB)

(73) Assignee: T.J.Smith and Nephew, Limited, Hull (GB)

( * ) Notice: Subject to any disclaimer, the term of this patent is extended or adjusted under 35 U.S.C. 154(b) by 654 days.

(21) Appl. No.: 17/457,647

(22) Filed: Dec. 3, 2021

(65) Prior Publication Data

US 2022/0088289 A1   Mar. 24, 2022
US 2023/0148439 A9   May 11, 2023

Related U.S. Application Data

(63) Continuation-in-part of application No. 16/650,806, filed as application No. PCT/EP2018/075751 on Sep.
(Continued)

(30) Foreign Application Priority Data

Jul. 13, 2018   (GB) .................................... 1811494

(51) Int. Cl.
*A61M 1/00*   (2006.01)
*A61F 13/02*   (2024.01)
*A61F 13/05*   (2024.01)

(52) U.S. Cl.
CPC ............. *A61M 1/966* (2021.05); *A61F 13/05* (2024.01); *A61M 2205/18* (2013.01);
(Continued)

(58) Field of Classification Search
CPC .............. A61M 1/966; A61M 2205/18; A61M 2205/3327; A61M 2205/3553;
(Continued)

(56) References Cited

U.S. PATENT DOCUMENTS

| 695,270 A | 3/1902 | Beringer |
| 3,194,239 A | 7/1965 | Sullivan et al. |

(Continued)

FOREIGN PATENT DOCUMENTS

| CN | 1797418 A | 7/2006 |
| CN | 102961815 A | 3/2013 |

(Continued)

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.
(Continued)

*Primary Examiner* — Susan S Su
*Assistant Examiner* — Brandon W. Levy
(74) *Attorney, Agent, or Firm* — Knobbe, Martens, Olson & Bear, LLP

(57) ABSTRACT

Embodiments of negative pressure wound therapy devices and methods for controlling and operating such devices are disclosed. A negative pressure wound therapy apparatus can include a housing, a negative pressure source, a pressure sensor, and an electronic control circuitry. The negative pressure source can couple via a fluid flow path to a wound dressing covering a wound and provide negative pressure to the wound. The electronic controller circuitry can operate the negative pressure source, detect a presence of blockage in the fluid flow path based on comparing one or more peak-to-peak measurments of pressure in the fluid flow path measured by the pressure sensor to a threshold, and adjust
(Continued)

the threshold responsive to a determination that the housing is positioned in a moving transporter. The moving transporter can be an automobile, train, or airplane.

17 Claims, 35 Drawing Sheets

Related U.S. Application Data 24, 2018, now abandoned, application No. 17/457,647 is a continuation-in-part of application No. 16/333,948, filed as application No. PCT/US2017/053839 on Sep. 27, 2017, now abandoned.

(60) Provisional application No. 62/563,889, filed on Sep. 27, 2017, provisional application No. 62/401,019, filed on Sep. 28, 2016.

(52) U.S. Cl.
CPC .............. *A61M 2205/3327* (2013.01); *A61M 2205/3553* (2013.01); *A61M 2205/502* (2013.01); *A61M 2205/581* (2013.01); *A61M 2205/6063* (2013.01)

(58) Field of Classification Search
CPC ...... A61M 2205/502; A61M 2205/581; A61M 2205/6063; A61M 2205/6018; A61M 2205/6072; A61M 1/918; A61M 1/96; A61M 1/74; A61M 1/73; A61M 2205/3334; A61M 1/732; A61M 2205/3306; A61M 2205/583; A61M 1/962; A61M 1/984; A61M 1/982; A61M 2205/3561; A61M 2205/52; A61M 2205/6081; A61M 2205/3584; A61M 2205/3592; A61M 2209/086; A61F 13/05; A61B 5/411; G16H 40/67; G16H 10/00; G16H 10/60

See application file for complete search history.

(56) References Cited

U.S. PATENT DOCUMENTS

| | | | |
|---|---|---|---|
| 4,832,299 | A | 5/1989 | Gorton et al. |
| 5,219,428 | A | 6/1993 | Stern |
| 5,473,536 | A | 12/1995 | Wimmer |
| 5,899,665 | A | 5/1999 | Makino et al. |
| 5,960,403 | A | 9/1999 | Brown |
| 6,055,506 | A | 4/2000 | Frasca et al. |
| 6,336,900 | B1 | 1/2002 | Alleckson et al. |
| 6,353,445 | B1 | 3/2002 | Babula et al. |
| 6,375,614 | B1 | 4/2002 | Braun et al. |
| 6,385,622 | B2 | 5/2002 | Bouve et al. |
| 6,406,426 | B1 | 6/2002 | Reuss et al. |
| 6,434,572 | B2 | 8/2002 | Derzay et al. |
| 6,460,041 | B2 | 10/2002 | Lloyd |
| 6,574,518 | B1 | 6/2003 | Lounsberry et al. |
| 6,640,145 | B2 | 10/2003 | Hoffberg et al. |
| 6,640,246 | B1 | 10/2003 | Gary et al. |
| 6,675,131 | B2 | 1/2004 | Hahn |
| 6,681,003 | B2 | 1/2004 | Linder et al. |
| 6,723,046 | B2 | 4/2004 | Lichtenstein et al. |
| 6,747,556 | B2 | 6/2004 | Medema et al. |
| 6,779,024 | B2 | 8/2004 | DeLaHuerga |
| 6,782,285 | B2 | 8/2004 | Birkenbach et al. |
| 6,856,825 | B2 | 2/2005 | Hahn |
| 6,868,528 | B2 | 3/2005 | Roberts |
| 6,871,211 | B2 | 3/2005 | Labounty et al. |
| 6,909,974 | B2 | 6/2005 | Yung et al. |
| 6,912,481 | B2 | 6/2005 | Breunissen et al. |
| 6,961,731 | B2 | 11/2005 | Holbrook |
| 7,004,915 | B2 | 2/2006 | Boynton et al. |
| 7,022,113 | B2 | 4/2006 | Lockwood et al. |
| 7,051,012 | B2 | 5/2006 | Cole et al. |
| 7,062,251 | B2 | 6/2006 | Birkett et al. |
| 7,066,883 | B2 | 6/2006 | Schmidt et al. |
| 7,103,578 | B2 | 9/2006 | Beck et al. |
| 7,108,683 | B2 | 9/2006 | Zamierowski |
| 7,120,488 | B2 | 10/2006 | Nova et al. |
| 7,133,869 | B2 | 11/2006 | Bryan et al. |
| 7,167,858 | B2 | 1/2007 | Naeymi-Rad et al. |
| 7,212,829 | B1 | 5/2007 | Lau et al. |
| 7,264,591 | B2 | 9/2007 | Brown |
| 7,300,418 | B2 | 11/2007 | Zaleski |
| 7,304,573 | B2 | 12/2007 | Postma |
| 7,311,665 | B2 | 12/2007 | Hawthorne et al. |
| 7,333,002 | B2 | 2/2008 | Bixler et al. |
| 7,353,179 | B2 | 4/2008 | Ott et al. |
| 7,384,267 | B1 | 6/2008 | Franks et al. |
| 7,430,598 | B2 | 9/2008 | Raden et al. |
| 7,438,705 | B2 | 10/2008 | Karpowicz et al. |
| 7,451,002 | B2 | 11/2008 | Choubey |
| 7,457,804 | B2 | 11/2008 | Uber et al. |
| 7,460,872 | B2 | 12/2008 | Millard et al. |
| 7,492,278 | B2 | 2/2009 | Zigmond et al. |
| 7,534,240 | B1 | 5/2009 | Johnson |
| 7,598,855 | B2 | 10/2009 | Scalisi et al. |
| 7,608,066 | B2 | 10/2009 | Vogel |
| 7,627,334 | B2 | 12/2009 | Cohen et al. |
| 7,649,449 | B2 | 1/2010 | Fenske et al. |
| 7,671,733 | B2 | 3/2010 | McNeal et al. |
| 7,684,999 | B2 | 3/2010 | Brown |
| 7,734,764 | B2 | 6/2010 | Weiner et al. |
| 7,749,164 | B2 | 7/2010 | Davis |
| 7,758,555 | B2 | 7/2010 | Kelch et al. |
| 7,779,153 | B2 | 8/2010 | Van den Heuvel et al. |
| 7,789,828 | B2 | 9/2010 | Clapp |
| 7,794,438 | B2 | 9/2010 | Henley et al. |
| 7,827,148 | B2 | 11/2010 | Mori et al. |
| 7,865,375 | B2 | 1/2011 | Lancaster et al. |
| 7,889,069 | B2 | 2/2011 | Fifolt et al. |
| 7,890,887 | B1 | 2/2011 | Linardos et al. |
| 7,912,823 | B2 | 3/2011 | Ferrari et al. |
| 7,925,603 | B1 | 4/2011 | Laidig et al. |
| 7,933,817 | B2 | 4/2011 | Radl et al. |
| 7,976,519 | B2 | 7/2011 | Bubb et al. |
| 7,981,098 | B2 | 7/2011 | Boehringer et al. |
| 7,988,850 | B2 | 8/2011 | Roncadi et al. |
| 8,015,443 | B2 | 9/2011 | Adachi |
| 8,015,972 | B2 | 9/2011 | Pirzada |
| 8,019,618 | B2 | 9/2011 | Brown |
| 8,036,925 | B2 | 10/2011 | Choubey |
| 8,054,950 | B1 | 11/2011 | Hung et al. |
| 8,069,057 | B2 | 11/2011 | Choubey et al. |
| 8,094,009 | B2 | 1/2012 | Allen et al. |
| 8,126,735 | B2 | 2/2012 | Dicks et al. |
| 8,130,095 | B2 | 3/2012 | Allen et al. |
| 8,131,472 | B2 | 3/2012 | Chow et al. |
| 8,180,750 | B2 | 5/2012 | Wilmering et al. |
| 8,190,445 | B2 | 5/2012 | Kuth et al. |
| 8,190,448 | B2 | 5/2012 | Bajars et al. |
| 8,228,188 | B2 | 7/2012 | Key et al. |
| 8,246,606 | B2 | 8/2012 | Stevenson et al. |
| 8,249,894 | B2 | 8/2012 | Brown |
| 8,255,241 | B2 | 8/2012 | Cafer |
| 8,260,630 | B2 | 9/2012 | Brown |
| 8,280,682 | B2 | 10/2012 | Vock et al. |
| 8,284,046 | B2 | 10/2012 | Allen et al. |
| 8,290,792 | B2 | 10/2012 | Sekura |
| 8,291,337 | B2 | 10/2012 | Gannin et al. |
| 8,323,263 | B2 | 12/2012 | Wood et al. |
| 8,332,233 | B2 | 12/2012 | Ott et al. |
| 8,334,768 | B2 | 12/2012 | Eaton et al. |
| 8,337,482 | B2 | 12/2012 | Wood et al. |
| 8,360,975 | B1 | 1/2013 | Schwieterman et al. |
| 8,400,295 | B1 | 3/2013 | Khaira |
| 8,422,377 | B2 | 4/2013 | Weiner et al. |
| 8,424,517 | B2 | 4/2013 | Sutherland et al. |
| 8,436,871 | B2 | 5/2013 | Alberte |
| 8,439,882 | B2 | 5/2013 | Kelch |
| 8,444,613 | B2 | 5/2013 | Svedman et al. |

(56) References Cited

U.S. PATENT DOCUMENTS

| | | |
|---|---|---|
| 8,457,740 B2 | 6/2013 | Osche |
| 8,480,641 B2 | 7/2013 | Jacobs |
| 8,515,776 B2 | 8/2013 | Schoenberg |
| 8,532,764 B2 | 9/2013 | Duke |
| 8,540,688 B2 | 9/2013 | Eckstein et al. |
| 8,545,483 B2 | 10/2013 | Schwabe et al. |
| 8,554,195 B2 | 10/2013 | Rao |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,600,777 B2 | 12/2013 | Schoenberg et al. |
| 8,626,342 B2 | 1/2014 | Williams et al. |
| 8,626,526 B2 | 1/2014 | Lemke et al. |
| 8,632,485 B2 | 1/2014 | Schlaeper et al. |
| 8,641,693 B2 | 2/2014 | Locke et al. |
| 8,659,420 B2 | 2/2014 | Salvat et al. |
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,725,528 B2 | 5/2014 | Locke et al. |
| 8,756,078 B2 | 6/2014 | Collins et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,838,136 B2 | 9/2014 | Carnes et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,943,168 B2 | 1/2015 | Wiesner et al. |
| 8,945,073 B2 | 2/2015 | Croizat et al. |
| 8,947,237 B2 | 2/2015 | Margon et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 | 6/2015 | Buan et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,075 B1 | 12/2015 | Poltorak |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,424,020 B2 | 8/2016 | Borges et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,474,679 B2 | 10/2016 | Locke et al. |
| 9,483,614 B2 | 11/2016 | Ash et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,700,462 B2 | 7/2017 | DeBusk et al. |
| 9,716,757 B2 | 7/2017 | Fernandes |
| 9,717,565 B2 | 8/2017 | Blair |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,864,066 B2 | 1/2018 | Park et al. |
| 9,871,866 B2 | 1/2018 | Borges et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,064,551 B2 | 9/2018 | Cosentino et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,207,031 B2 | 2/2019 | Toth |
| 10,276,038 B2 | 4/2019 | Hastings |
| 2002/0013516 A1 | 1/2002 | Freyre et al. |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2003/0009244 A1 | 1/2003 | Engleson et al. |
| 2003/0018736 A1 | 1/2003 | Christ et al. |
| 2003/0105389 A1 | 6/2003 | Noonan et al. |
| 2003/0105649 A1 | 6/2003 | Sheiner et al. |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0019464 A1 | 1/2004 | Martucci et al. |
| 2004/0054775 A1 | 3/2004 | Poliac et al. |
| 2004/0078223 A1 | 4/2004 | Sacco et al. |
| 2004/0143458 A1 | 7/2004 | Pulkkinen et al. |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0278409 A1 | 12/2005 | Kutzik et al. |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0064491 A1 | 3/2006 | Ebert et al. |

(56) References Cited

U.S. PATENT DOCUMENTS

| | | |
|---|---|---|
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0224051 A1 | 10/2006 | Teller et al. |
| 2006/0246922 A1 | 11/2006 | Gasbarro et al. |
| 2007/0136099 A1 | 6/2007 | Neligh et al. |
| 2007/0156456 A1 | 7/2007 | McGillin et al. |
| 2007/0197881 A1 | 8/2007 | Wolf et al. |
| 2007/0219532 A1 | 9/2007 | Karpowicz et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0009681 A1 | 1/2008 | Al Hussiny |
| 2008/0086357 A1 | 4/2008 | Choubey et al. |
| 2008/0091659 A1 | 4/2008 | McFaul |
| 2008/0119705 A1 | 5/2008 | Patel et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177579 A1 | 7/2008 | Dehaan |
| 2008/0221396 A1 | 9/2008 | Garces et al. |
| 2008/0242945 A1 | 10/2008 | Gugliotti et al. |
| 2008/0312953 A1 | 12/2008 | Claus |
| 2009/0037220 A1 | 2/2009 | Chambers et al. |
| 2009/0048492 A1 | 2/2009 | Rantala et al. |
| 2009/0048865 A1 | 2/2009 | Breazeale, Jr. |
| 2009/0097623 A1 | 4/2009 | Bharadwaj |
| 2009/0099866 A1 | 4/2009 | Newman |
| 2009/0099867 A1 | 4/2009 | Newman |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0208385 A1 | 8/2009 | Howorth et al. |
| 2009/0224889 A1 | 9/2009 | Aggarwal et al. |
| 2009/0270833 A1 | 10/2009 | DeBelser et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0145161 A1 | 6/2010 | Niyato et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2011/0004188 A1 | 1/2011 | Shekalim |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0106561 A1 | 5/2011 | Eaton, Jr. et al. |
| 2011/0112857 A1 | 5/2011 | Yurko et al. |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0246219 A1 | 10/2011 | Smith et al. |
| 2011/0275353 A1 | 11/2011 | Liu |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0109034 A1 | 5/2012 | Locke et al. |
| 2012/0123323 A1 | 5/2012 | Kagan et al. |
| 2012/0123796 A1 | 5/2012 | McFaul |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0191475 A1 | 7/2012 | Pandey |
| 2012/0212455 A1 | 8/2012 | Kloeffel |
| 2012/0215455 A1 | 8/2012 | Patil et al. |
| 2012/0226768 A1 | 9/2012 | Gaines et al. |
| 2012/0259651 A1 | 10/2012 | Mallon et al. |
| 2012/0271256 A1 | 10/2012 | Locke et al. |
| 2012/0290217 A1 | 11/2012 | Shoval et al. |
| 2012/0293322 A1 | 11/2012 | Ray et al. |
| 2012/0295566 A1 | 11/2012 | Collins et al. |
| 2012/0310205 A1 | 12/2012 | Lee et al. |
| 2013/0018355 A1 | 1/2013 | Brand et al. |
| 2013/0023719 A1 | 1/2013 | Bennett |
| 2013/0035615 A1 | 2/2013 | Hsieh |
| 2013/0045764 A1 | 2/2013 | Vik et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0133036 A1 | 5/2013 | Wang et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0172691 A1 | 7/2013 | Tran |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |

(56) References Cited

U.S. PATENT DOCUMENTS

| | | |
|---|---|---|
| 2013/0345524 A1 | 12/2013 | Meyer et al. |
| 2014/0002234 A1 | 1/2014 | Alwan |
| 2014/0009473 A1 | 1/2014 | Korkishko |
| 2014/0018637 A1 | 1/2014 | Bennett et al. |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0039424 A1 | 2/2014 | Locke |
| 2014/0055588 A1 | 2/2014 | Bangera et al. |
| 2014/0058714 A1 | 2/2014 | Boyer |
| 2014/0067426 A1 | 3/2014 | Neff |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0136218 A1 | 5/2014 | Bolene et al. |
| 2014/0148138 A1 | 5/2014 | Chou |
| 2014/0171753 A1 | 6/2014 | Montejo et al. |
| 2014/0187888 A1 | 7/2014 | Hatziantoniou |
| 2014/0207090 A1 | 7/2014 | Jian |
| 2014/0222377 A1 | 8/2014 | Bitan et al. |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0316819 A1 | 10/2014 | Dunsirn et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025482 A1 | 1/2015 | Begin et al. |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094830 A1 | 4/2015 | Lipoma et al. |
| 2015/0095056 A1 | 4/2015 | Ryan et al. |
| 2015/0095059 A1 | 4/2015 | Yegge et al. |
| 2015/0095066 A1 | 4/2015 | Ryan et al. |
| 2015/0095068 A1 | 4/2015 | Ryan et al. |
| 2015/0100340 A1 | 4/2015 | Folsom et al. |
| 2015/0112707 A1 | 4/2015 | Manice et al. |
| 2015/0112725 A1 | 4/2015 | Ryan |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0120328 A1 | 4/2015 | Ryan et al. |
| 2015/0143300 A1 | 5/2015 | Zhang et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0227712 A1 | 8/2015 | Ryan et al. |
| 2015/0227716 A1 | 8/2015 | Ryan et al. |
| 2015/0227717 A1 | 8/2015 | Ryan et al. |
| 2015/0228043 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0250961 A1 | 9/2015 | Whitman et al. |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0290441 A1 | 10/2015 | Locke et al. |
| 2015/0304478 A1 | 10/2015 | Kim et al. |
| 2015/0310182 A1 | 10/2015 | Henze et al. |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004824 A1 | 1/2016 | Stanton et al. |
| 2016/0015962 A1 | 1/2016 | Shokoueinejad Maragheh et al. |
| 2016/0018963 A1 | 1/2016 | Robbins et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0067104 A1 | 3/2016 | Sarangapani et al. |
| 2016/0074234 A1 | 3/2016 | Abichandani et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0110985 A1 | 4/2016 | Lee et al. |
| 2016/0128571 A1 | 5/2016 | Adler |
| 2016/0129186 A1 | 5/2016 | Douglas et al. |
| 2016/0135752 A1 | 5/2016 | Beaumont |
| 2016/0136339 A1 | 5/2016 | Begin et al. |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0165719 A1 | 6/2016 | Li et al. |
| 2016/0166438 A1 | 6/2016 | Rovaniemi |
| 2016/0171866 A1 | 6/2016 | Dupasquier et al. |
| 2016/0180031 A1 | 6/2016 | Slater |
| 2016/0184496 A1* | 6/2016 | Jaecklein .............. A61M 1/982 604/318 |
| 2016/0184497 A1 | 6/2016 | Phillips et al. |
| 2016/0196399 A1 | 7/2016 | Bonhomme |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0246943 A1 | 8/2016 | Lake et al. |
| 2016/0260035 A1 | 9/2016 | Crooks et al. |
| 2016/0287189 A1 | 10/2016 | Modai et al. |
| 2016/0303358 A1 | 10/2016 | Croizat et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2017/0004106 A1 | 1/2017 | Joshua et al. |
| 2017/0004271 A1 | 1/2017 | Ash et al. |
| 2017/0007494 A1 | 1/2017 | Rock et al. |
| 2017/0014028 A1 | 1/2017 | Clear, Jr. |
| 2017/0017765 A1 | 1/2017 | Yegge et al. |
| 2017/0032648 A1 | 2/2017 | McClain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0061096 A1 | 3/2017 | Kelly et al. |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0116373 A1 | 4/2017 | Ginsburg et al. |
| 2017/0140120 A1 | 5/2017 | Thrower |
| 2017/0150939 A1 | 6/2017 | Shah |
| 2017/0188946 A1* | 7/2017 | Klusmann .............. G01P 15/18 |
| 2017/0193181 A1 | 7/2017 | Carter et al. |
| 2017/0212995 A1 | 7/2017 | Ingmanson |
| 2017/0220755 A1 | 8/2017 | Fowler et al. |
| 2017/0257682 A1 | 9/2017 | Shtalryd |
| 2017/0270533 A1 | 9/2017 | Barton et al. |
| 2017/0273116 A1 | 9/2017 | Elghazzawi |

(56) References Cited

U.S. PATENT DOCUMENTS

| | | | |
|---|---|---|---|
| 2017/0304510 A1 | 10/2017 | Askem et al. | |
| 2017/0327371 A1 | 11/2017 | Bai et al. | |
| 2017/0372010 A1 | 12/2017 | Doherty et al. | |
| 2018/0004908 A1 | 1/2018 | Barrus et al. | |
| 2018/0052454 A1 | 2/2018 | Magno et al. | |
| 2018/0055359 A1 | 3/2018 | Shamim et al. | |
| 2018/0089387 A1 | 3/2018 | Swank | |
| 2018/0121629 A1 | 5/2018 | Dyer et al. | |
| 2018/0139572 A1 | 5/2018 | Hansen | |
| 2018/0144817 A1 | 5/2018 | Lofgren et al. | |
| 2018/0158545 A1 | 6/2018 | Blomquist | |
| 2018/0160907 A1 | 6/2018 | Verma | |
| 2018/0181714 A1 | 6/2018 | Pillarisetty et al. | |
| 2018/0224559 A1 | 8/2018 | Park et al. | |
| 2018/0228945 A1 | 8/2018 | Guirguis et al. | |
| 2018/0229014 A1 | 8/2018 | Guirguis et al. | |
| 2018/0233016 A1 | 8/2018 | Daniel et al. | |
| 2018/0233221 A1 | 8/2018 | Blomquist | |
| 2018/0234499 A1 | 8/2018 | Borges et al. | |
| 2018/0279880 A1 | 10/2018 | Bacchi | |
| 2018/0286502 A1 | 10/2018 | Lane et al. | |
| 2018/0308569 A1 | 10/2018 | Luellen | |
| 2018/0308573 A1 | 10/2018 | Hochrein et al. | |
| 2018/0315492 A1 | 11/2018 | Bishop et al. | |
| 2018/0322944 A1 | 11/2018 | Valdizan | |
| 2019/0021911 A1 | 1/2019 | Askem et al. | |
| 2019/0231939 A1 | 8/2019 | Askem et al. | |
| 2020/0038249 A1 | 2/2020 | Pratt et al. | |
| 2020/0060879 A1 | 2/2020 | Edwards et al. | |
| 2020/0078224 A1 | 3/2020 | Carroll et al. | |
| 2021/0106736 A1 | 4/2021 | Askem | |
| 2022/0203015 A1 | 6/2022 | Hartwell et al. | |

FOREIGN PATENT DOCUMENTS

| | | |
|---|---|---|
| CN | 104200234 A | 12/2014 |
| CN | 104702683 A | 6/2015 |
| CN | 104721008 A | 6/2015 |
| CN | 104721892 A | 6/2015 |
| CN | 105453128 A | 3/2016 |
| CN | 105939658 A | 9/2016 |
| DE | 102010036405 A1 | 1/2012 |
| DE | 202016008343 U1 | 8/2017 |
| EP | 0980227 A1 | 2/2000 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |
| EP | 1587017 A2 | 10/2005 |
| EP | 1684146 A2 | 7/2006 |
| EP | 1788503 A2 | 5/2007 |
| EP | 1839244 A1 | 10/2007 |
| EP | 1839615 A1 | 10/2007 |
| EP | 1857950 A2 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2172859 A1 | 4/2010 |
| EP | 2214552 A1 | 8/2010 |
| EP | 2218478 A1 | 8/2010 |
| EP | 1404213 B1 | 3/2011 |
| EP | 1247229 B1 | 4/2011 |
| EP | 1406540 B1 | 6/2011 |
| EP | 1812094 B1 | 8/2011 |
| EP | 2384472 A1 | 11/2011 |
| EP | 2226002 B1 | 1/2012 |
| EP | 1610494 B1 | 3/2012 |
| EP | 1248660 B1 | 4/2012 |
| EP | 2023800 B1 | 4/2012 |
| EP | 2451513 A1 | 5/2012 |
| EP | 1248661 B1 | 8/2012 |
| EP | 2488977 A1 | 8/2012 |
| EP | 2562665 A2 | 2/2013 |
| EP | 2619723 A2 | 7/2013 |
| EP | 1881784 B1 | 10/2013 |
| EP | 2664194 A2 | 11/2013 |
| EP | 2743850 A2 | 6/2014 |
| EP | 2745204 A1 | 6/2014 |
| EP | 2795492 A1 | 10/2014 |
| EP | 2841895 A1 | 3/2015 |
| EP | 2850771 A1 | 3/2015 |
| EP | 2876567 A1 | 5/2015 |
| EP | 2891999 A2 | 7/2015 |
| EP | 2894581 A1 | 7/2015 |
| EP | 2906101 A2 | 8/2015 |
| EP | 2945084 A1 | 11/2015 |
| EP | 2962266 A1 | 1/2016 |
| EP | 2968829 A1 | 1/2016 |
| EP | 2973089 A1 | 1/2016 |
| EP | 3000082 A1 | 3/2016 |
| EP | 3010398 A1 | 4/2016 |
| EP | 3054389 A2 | 8/2016 |
| EP | 3070628 A1 | 9/2016 |
| EP | 3078010 A1 | 10/2016 |
| EP | 3096113 A1 | 11/2016 |
| EP | 2563437 B1 | 3/2017 |
| EP | 2773393 B1 | 3/2017 |
| EP | 3134854 A1 | 3/2017 |
| EP | 3027242 B1 | 4/2017 |
| EP | 2556650 B1 | 5/2017 |
| EP | 3174569 A1 | 6/2017 |
| EP | 3187200 A1 | 7/2017 |
| EP | 2632407 B1 | 8/2017 |
| EP | 3209358 A1 | 8/2017 |
| EP | 3041571 B1 | 9/2017 |
| EP | 2856767 B1 | 11/2017 |
| EP | 3252635 A1 | 12/2017 |
| EP | 2320971 B1 | 5/2018 |
| EP | 2335173 B1 | 5/2018 |
| EP | 3100188 B1 | 6/2018 |
| EP | 3330973 A1 | 6/2018 |
| EP | 3352174 A1 | 7/2018 |
| EP | 2440112 B1 | 10/2018 |
| EP | 3400549 A1 | 11/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 3377130 B1 | 4/2019 |
| EP | 2881875 B1 | 5/2019 |
| EP | 2836269 B1 | 8/2019 |
| EP | 2866851 B1 | 9/2019 |
| GB | 2409951 A | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 A | 5/2011 |
| GB | 2488904 A | 9/2012 |
| GB | 2446923 B | 5/2013 |
| GB | 2499986 A | 9/2013 |
| GB | 2491946 B | 8/2014 |
| GB | 2499873 B | 5/2016 |
| GB | 2533910 A | 7/2016 |
| GB | 2541286 A | 2/2017 |
| GB | 2550576 B | 6/2018 |
| JP | 2011234805 A | 11/2011 |
| WO | WO-9627163 A1 | 9/1996 |
| WO | WO-9744745 A1 | 11/1997 |
| WO | WO-9924927 A1 | 5/1999 |
| WO | WO-9963886 A1 | 12/1999 |

(56) References Cited

FOREIGN PATENT DOCUMENTS

| | | |
|---|---|---|
| WO | WO-0032088 A1 | 6/2000 |
| WO | WO-0060522 A2 | 10/2000 |
| WO | WO-0133457 A1 | 5/2001 |
| WO | WO-0181829 A1 | 11/2001 |
| WO | WO-0217075 A2 | 2/2002 |
| WO | WO-0233577 A1 | 4/2002 |
| WO | WO-02078594 A2 | 10/2002 |
| WO | WO-02101713 A1 | 12/2002 |
| WO | WO-03054668 A2 | 7/2003 |
| WO | WO-03065878 A2 | 8/2003 |
| WO | WO-03094090 A2 | 11/2003 |
| WO | WO-2004057514 A2 | 7/2004 |
| WO | WO-2004074457 A2 | 9/2004 |
| WO | WO-2005022349 A2 | 3/2005 |
| WO | WO-2005031632 A2 | 4/2005 |
| WO | WO-2005036447 A2 | 4/2005 |
| WO | WO-2005045461 A1 | 5/2005 |
| WO | WO-2005053793 A1 | 6/2005 |
| WO | WO-2005057466 A2 | 6/2005 |
| WO | WO-2005083619 A2 | 9/2005 |
| WO | WO-2005101282 A2 | 10/2005 |
| WO | WO-2005109297 A2 | 11/2005 |
| WO | WO-2005120097 A2 | 12/2005 |
| WO | WO-2006021154 A1 | 3/2006 |
| WO | WO-2006066583 A1 | 6/2006 |
| WO | WO-2006066585 A2 | 6/2006 |
| WO | WO-2006071711 A2 | 7/2006 |
| WO | WO-2006099120 A2 | 9/2006 |
| WO | WO-2006108304 A1 | 10/2006 |
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |
| WO | WO-2007137869 A2 | 12/2007 |
| WO | WO-2008010012 A2 | 1/2008 |
| WO | WO-2008036344 A1 | 3/2008 |
| WO | WO-2008039223 A1 | 4/2008 |
| WO | WO-2008039314 A2 | 4/2008 |
| WO | WO-2008062382 A2 | 5/2008 |
| WO | WO-2008067314 A2 | 6/2008 |
| WO | WO-2008116295 A1 | 10/2008 |
| WO | WO-2008150633 A2 | 12/2008 |
| WO | WO-2009061940 A2 | 5/2009 |
| WO | WO-2009140669 A2 | 11/2009 |
| WO | WO-2010017484 A2 | 2/2010 |
| WO | WO-2010025166 A1 | 3/2010 |
| WO | WO-2010025467 A1 | 3/2010 |
| WO | WO-2010078558 A1 | 7/2010 |
| WO | WO-2010085033 A2 | 7/2010 |
| WO | WO-2010132617 A2 | 11/2010 |
| WO | WO-2010145780 A1 | 12/2010 |
| WO | WO-2011005633 A2 | 1/2011 |
| WO | WO-2011023384 A1 | 3/2011 |
| WO | WO-2011039676 A2 | 4/2011 |
| WO | WO-2011046860 A2 | 4/2011 |
| WO | WO-2011047334 A1 | 4/2011 |
| WO | WO-2011123933 A1 | 10/2011 |
| WO | WO-2011137230 A1 | 11/2011 |
| WO | WO-2012051278 A1 | 4/2012 |
| WO | WO-2012100624 A1 | 8/2012 |
| WO | WO-2012127281 A1 | 9/2012 |
| WO | WO-2013026999 A1 | 2/2013 |
| WO | WO-2013036853 A2 | 3/2013 |
| WO | WO-2013061887 A1 | 5/2013 |
| WO | WO-2013102855 A1 | 7/2013 |
| WO | WO-2013109517 A1 | 7/2013 |
| WO | WO-2013138182 A1 | 9/2013 |
| WO | WO-2013141870 A1 | 9/2013 |
| WO | WO-2013155193 A1 | 10/2013 |
| WO | WO-2013175076 A1 | 11/2013 |
| WO | WO-2014015215 A2 | 1/2014 |
| WO | WO-2014018786 A2 | 1/2014 |
| WO | WO-2014075494 A1 | 5/2014 |
| WO | WO-2014089086 A1 | 6/2014 |
| WO | WO-2014100036 A1 | 6/2014 |
| WO | WO-2014100687 A2 | 6/2014 |
| WO | WO-2014106056 A2 | 7/2014 |
| WO | WO-2014123846 A1 | 8/2014 |
| WO | WO-2014133822 A2 | 9/2014 |
| WO | WO-2014141221 A2 | 9/2014 |
| WO | WO-2014145496 A1 | 9/2014 |
| WO | WO-2014150255 A2 | 9/2014 |
| WO | WO-2014152963 A1 | 9/2014 |
| WO | WO-2014189070 A1 | 11/2014 |
| WO | WO-2014009876 A3 | 12/2014 |
| WO | WO-2015019273 A2 | 2/2015 |
| WO | WO-2015025482 A1 | 2/2015 |
| WO | WO-2015026387 A1 | 2/2015 |
| WO | WO-2015050816 A1 | 4/2015 |
| WO | WO-2015078112 A1 | 6/2015 |
| WO | WO-2015085249 A1 | 6/2015 |
| WO | WO-2015091070 A1 | 6/2015 |
| WO | WO-2015124670 A1 | 8/2015 |
| WO | WO-2015132528 A1 | 9/2015 |
| WO | WO-2015140801 A2 | 9/2015 |
| WO | WO-2015143099 A2 | 9/2015 |
| WO | WO-2015145455 A1 | 10/2015 |
| WO | WO-2015156143 A1 | 10/2015 |
| WO | WO-2015164787 A1 | 10/2015 |
| WO | WO-2015168720 A1 | 11/2015 |
| WO | WO-2015179915 A1 | 12/2015 |
| WO | WO-2015179916 A1 | 12/2015 |
| WO | WO-2015179917 A1 | 12/2015 |
| WO | WO-2015181836 A2 | 12/2015 |
| WO | WO-2015187480 A1 | 12/2015 |
| WO | WO-2016001088 A1 | 1/2016 |
| WO | WO-2016006536 A1 | 1/2016 |
| WO | WO-2016075656 A1 | 5/2016 |
| WO | WO-2016103035 A2 | 6/2016 |
| WO | WO-2016108163 A1 | 7/2016 |
| WO | WO-2016118318 A1 | 7/2016 |
| WO | WO-2016120820 A2 | 8/2016 |
| WO | WO-2016136694 A1 | 9/2016 |
| WO | WO-2016141799 A1 | 9/2016 |
| WO | WO-2016151364 A1 | 9/2016 |
| WO | WO-2016160849 A1 | 10/2016 |
| WO | WO-2016175649 A1 | 11/2016 |
| WO | WO-2016178936 A1 | 11/2016 |
| WO | WO-2016190978 A1 | 12/2016 |
| WO | WO-2017001848 A1 | 1/2017 |
| WO | WO-2017004423 A1 | 1/2017 |
| WO | WO-2017027729 A2 | 2/2017 |
| WO | WO-2017027850 A1 | 2/2017 |
| WO | WO-2017035024 A1 | 3/2017 |
| WO | WO-2017053384 A1 | 3/2017 |
| WO | WO-2017062042 A1 | 4/2017 |
| WO | WO-2017142100 A1 | 8/2017 |
| WO | WO-2017146986 A1 | 8/2017 |
| WO | WO-2017165895 A1 | 9/2017 |
| WO | WO-2017186771 A1 | 11/2017 |
| WO | WO-2017192673 A1 | 11/2017 |
| WO | WO-2017195038 A1 | 11/2017 |
| WO | WO-2018007100 A1 | 1/2018 |
| WO | WO-2018013666 A1 | 1/2018 |
| WO | WO-2018033819 A1 | 2/2018 |
| WO | WO-2018044894 A1 | 3/2018 |
| WO | WO-2018064234 A1 | 4/2018 |
| WO | WO-2018067593 A2 | 4/2018 |
| WO | WO-2018082813 A1 | 5/2018 |
| WO | WO-2018091492 A1 | 5/2018 |
| WO | WO-2018096390 A1 | 5/2018 |
| WO | WO-2018145880 A1 | 8/2018 |
| WO | WO-2019063462 A1 | 4/2019 |
| WO | WO-2019238927 A1 | 12/2019 |

OTHER PUBLICATIONS

International Preliminary Report on Patentability for Application No. PCT/EP2018/075751, mailed on Apr. 9, 2020, 13 pages.
International Preliminary Report on Patentability for Application No. PCT/US2017/053839, mailed on Apr. 11, 2019, 8 pages.

(56) References Cited

OTHER PUBLICATIONS

International Search Report and Written Opinion for Application No. PCT/EP2018/081198, mailed on Feb. 28, 2019, 17 pages.
International Search Report and Written Opinion for Application No. PCT/US2017/053839, mailed on Dec. 5, 2017, 15 pages.
International Search Report and Written Opinion for PCT Application No. PCT/EP2018/075751, mailed on Mar. 11, 2019, 20 pages.
Invitation to Pay Additional Fees and Partial Search Report for Application No. PCT/EP2018/075751, mailed on Jan. 10, 2019, 18 pages.
NXP., "NXP Semiconductors—AN11276 NTAG Antenna Design Guide," Revision 1.5, released Apr. 27, 2016, 47 pages.

* cited by examiner

SYSTEMS AND METHODS FOR OPERATING NEGATIVE PRESSURE WOUND THERAPY DEVICES

CROSS-REFERENCE TO RELATED APPLICATIONS

This application is a continuation in part of U.S. application Ser. No. 16/650806, filed Mar. 25, 2020, which is a U.S. national stage application of International Patent Application No. PCT/EP2018/075751, filed Sep. 24, 2018, which claims the benefit of U.S. Provisional Application No. 62/563,889, filed Sep. 27, 2017, and U.K. Provisional Application No. 1811494.2, filed Jul. 13, 2018.

This application is a continuation in part of U.S. application Ser. No. 16/333948, filed Mar. 15, 2019, which is a U.S. national stage application of International Patent Application No. PCT/US2017/053839, filed Sep. 27, 2017, which claims the benefit of U.S. Provisional Application No. 62/401,019, filed Sep. 28, 2016, the disclosure of each of which is hereby incorporated by reference in its entirety.

TECHNICAL FIELD

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

However, prior art negative pressure wound therapy or other wound therapy systems provide little security measures to prevent exposure to security risks. This can cause the negative pressure therapy system to be exposed to security concerns.

SUMMARY

Disclosed embodiments relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound dressing material currently employed and can advance the rate of healing. The devices, methods, and systems may be simultaneously used with negative pressure to remove wound fluids.

In some embodiments, an apparatus for applying negative pressure to a wound is disclosed. The apparatus can include a housing, a pressure source supported by the housing and configured to couple via a fluid flow path to a wound dressing positioned on a wound and provide negative pressure to the wound, a controller supported by the housing and configured to operate the pressure source to provide negative pressure to the wound, and an output device supported by the housing and configured to provide identification data to an electronic device. The identification data being usable by the electronic device to access a label associated with the housing or one or more components supported by the housing.

The apparatus of the preceding paragraph can include one or more of the following features: The identification data can be usable by the electronic device to access the label from a remote database via a computer network. The output device can include a display that may present the identification data as an optical, machine-readable representation of the identification data. The optical, machine-readable representation of the identification data can include a two-dimensional barcode. The output device can include a transmitter configured to wirelessly transmit the identification data to the electronic device. The electronic device can execute an application that receives the identification data from the output device and transmits a request for the label according to the identification data. The electronic device can execute an application that receives the identification data from the output device, transmits via a computer network a request for the label according to the identification data, presents the label on a display to a user, and enables the user of the electronic device to instruct the controller to operate the pressure source to provide negative pressure to the wound dressing. The electronic device can execute an application that transmits a confirmation or a verification of presentation of the label on the display. The controller can determine a location of the housing and automatically select the identification data from a plurality of identification data according to the location. The controller can inactivate the pressure source until the output device provides the identification data to the electronic device. The electronic device can include a mobile personal computer that communicates via a cellular communications network.

In some embodiments, a method is disclosed for operating a wound therapy system. The method can include: retrieving identification data from a memory device of a wound therapy device; outputting the identification data from the wound therapy device to an electronic device; receiving the identification data with the electronic device; generating a request from the identification data with the electronic device, the request being a request to access a label associated with the wound therapy device; transmitting the request with the electronic device via a computer network to a remote database; receiving the label via the computer network; and outputting the label for presentation to a user of the electronic device.

The method of the preceding paragraph can include one or more of the following features: The method can include transmitting via the computer network a confirmation or a verification of the outputting. The outputting the identification data can include presenting, on a display of the negative pressure wound therapy device, the identification data as an optical, machine-readable representation of the identification data, and the receiving the identification data can include receiving the identification data with an image sensor of the electronic device. The outputting the identification data can include wirelessly transmitting the identification data with a transmitter of the negative pressure wound therapy device, and the receiving the identification data can include receiving the identification data with a receiver of the electronic device. The outputting the label can include displaying the label on a display of the electronic device.

In some embodiments, an apparatus for applying negative pressure to a wound is disclosed. The apparatus can include a pressure source configured to couple via a fluid flow path to a wound dressing and provide negative pressure to the wound dressing; and a controller. The controller can receive input data, determine a control value from the input data, and adjust an operation performed by the controller according to the control value so that the operation is performed differently than if the operation is performed not according to the control value.

The apparatus of the preceding paragraph can include one or more of the following features: The controller can transmit a verification or a confirmation adjustment to the operation to a remote device via a computer network. The control value can be indicative of operation of the pressure source at an altitude above a threshold, and the operation can be wound therapy performed using the pressure source. The fluid flow path can include a plurality of lumens. The sensor can monitor the pressure at the wound dressing, in one or lumens of the fluid flow path, or at or near an inlet of the pressure source. The controller can activate and deactivate the pressure source.

In some embodiments, an apparatus for applying pressure to a wound is disclosed. The apparatus can include a housing, a motion sensor supported by the housing and configured to output motion data indicative of a motion of the housing, a pressure source supported by the housing, and a controller. The pressure source can couple via a fluid flow path to a wound dressing positioned on a wound and provide negative pressure to the wound. The controller can detect an error condition associated with providing of negative pressure to the wound with the pressure source, determine a cause of the error condition from the motion data, and output an alert for presentation to a user notifying the user of the cause of the error condition.

The apparatus of the preceding paragraph can include one or more of the following features: The error condition can include a blockage in the fluid flow path or a low pressure level at the wound. The controller can determine the blockage from a flow in the fluid flow path or a level of activity of the pressure source. The apparatus can include a canister supported by the housing that may collect fluid aspirated from the wound, and the cause of the error condition can be a rotation of the housing that likely saturated a filter of the canister with the fluid or a vibration of the housing that likely saturated a filter of the canister with the fluid. The controller can output a user instruction to the user indicating how to remedy the cause of the error condition. The user instruction can indicate to replace a filter of a canister, and the canister can be supported by the housing and collect fluid aspirated from the wound. The controller can output a user instruction to the user indicating how to prevent future occurrences of the error condition. The user instruction can indicate not to rotate the housing as detected from the motion. The controller can, responsive to detection of the error condition, operate the pressure source differently than prior to detection of the error condition. The motion sensor can include an accelerometer. The controller can add an entry to a log indicating an occurrence of the error condition, determine a frequency of occurrence of the error condition from the log, and operate the pressure source. The apparatus can include a display, and the display can visually present the alert to the user. The apparatus can include a speaker, and the speaker can audibly present the alert to the user.

In some embodiments, a method for operating a wound therapy device is disclosed. The method can include: operating a pressure source of the wound therapy device to provide negative pressure via a fluid flow path to a wound dressing positioned on a wound, the pressure source being supported by a housing of the wound therapy device; generating motion data indicative of a motion of the housing; detecting an error condition associated with providing of negative pressure to the wound with the pressure source; determining a cause of the error condition from the motion data; and outputting an alert for presentation to a user notifying the user of the cause of the error condition.

The method of the preceding paragraph can include one or more of the following features: The wound therapy device can be a negative pressure wound therapy device. The wound therapy device can include a canister supported by the housing that may collect fluid aspirated from the wound, and the cause of the error condition can be a rotation of the housing that likely caused a filter of the canister to become saturated with the fluid. The method can include outputting a user instruction to the user indicating how to remedy the cause of the error condition. The user instruction can indicate to replace a filter of a canister, and the canister can be supported by the housing and collect fluid aspirated from the wound. The method can include outputting a user instruction to the user indicating how to prevent future occurrences of the error condition or operating the pressure source differently responsive to determining the cause of the error condition.

In certain embodiments, an apparatus for applying negative pressure to a wound is provided, the apparatus comprises a controller coupled to a memory and a negative pressure source configured to provide negative pressure via a fluid flow path to a wound covered by a wound dressing. The controller may be configured to operate the negative pressure source to provide negative pressure to the wound, communicate with a remote computing device via a computer network according to a security protocol, and/or process data received from the remote computing device according to a security rule. The security protocol can comprise periodically assigning a new IP address to the apparatus.

The apparatus of the preceding paragraph can further comprise one or more of the following features: The security protocol can further comprise assigning a new IP address to the apparatus for each communication request to the remote computing device and encrypting communications with the remote computing device through mutual authentication. The security rule can comprise not responding to any redirect requests to a network address different from a network address of the remote computing device. The mutual authentication may be performed via security certificates stored in the memory of the apparatus and on the remote computing device. The security certificate stored in the memory can uniquely identify the apparatus. The memory can stores instructions that, when executed by the controller, cause the controller to operate the negative pressure source, communicate with the remote computing device, and process data received from the remote computing device. The security rule may comprise, in response to receiving from the computing device an update of at least some instructions stored in the memory, verifying an identity of an author of the update prior to updating the at least some instructions. The apparatus may further comprise one or more anti-tampering mechanisms configured to indicate unauthorized use of the apparatus. The controller may be configured to process the data according to the security rule so that access to the data provided by the controller via the computer network is limited to one or more authenticated devices. The controller may be configured to receive the data according to the security rule so that the data is enabled to adjust a first function performable by the controller and prevented from adjusting a second function performable by the controller. The security rule can comprise enforcing code signing. The security rule can comprise enforcing transport encryption. Transport encryption may utilize transport layer security. The security rule can comprise utilizing mutual authentication. Mutual authentication may be established through use of server and client certificates. The data can comprise data indicative of operations of the negative pressure source or identification information for a user of the negative pressure source. The data can comprise data indicative of operations of the negative pressure source or patient data for a user of the apparatus.

In certain embodiments, a method for operating a negative pressure wound therapy apparatus, the method comprises: activating a negative pressure source configured to provide negative pressure via a fluid flow path to a wound covered by a wound dressing, communicating with a remote computing device via a computer network according to a security protocol, and processing data received from the remote computing device according to a security rule. The security protocol can comprise periodically assigning a new IP address to the apparatus. The method may be performed by a controller of the apparatus.

The method of the preceding paragraph can further include one or more of the following features: The security protocol can further comprise assigning a new IP address to the apparatus for each communication request to the remote computing device and encrypting communications with the remote computing device through mutual authentication. The security rule can comprise not responding to any redirect requests to a network address different from a network address of the remote computing device. Mutual authentication may be performed via security certificates stored in a memory of the apparatus and on the remote computing device. The security certificate may be stored in the memory uniquely identifies the apparatus. The memory may store instructions that, when executed by the controller, cause the controller to operate the negative pressure source, communicate with the remote computing device, and process data received from the remote computing device. The security rule can comprise, in response to receiving from the computing device an update of at least some instructions stored in the memory, verifying an identity of an author of the update prior to updating the at least some instructions. The apparatus can further comprise one or more anti-tampering mechanisms configured to indicate unauthorized use of the apparatus. The controller may be configured to process the data according to the security rule so that access to the data provided by the controller via the computer network is limited to one or more authenticated devices. The controller may be configured to receive the data according to the security rule so that the data is enabled to adjust a first function performable by the controller and prevented from adjusting a second function performable by the controller. The security rule can comprise enforcing code signing. The security rule can comprise enforcing transport encryption. Transport encryption may utilize transport layer security. The security rule can comprise utilizing mutual authentication. Mutual authentication may be established through use of server and client certificates. The data can comprise data indicative of operations of the negative pressure source or identification information for a user of the negative pressure source. The data can comprise data indicative of operations of the negative pressure source or patient data for a user of the apparatus.

Other embodiments of wound closure devices, stabilizing structures and associated apparatuses are described below.

BRIEF DESCRIPTION OF THE DRAWINGS

Embodiments of the present disclosure will now be described hereinafter, by way of example only, with reference to the accompanying drawings in which.

DETAILED DESCRIPTION

Figure 1:
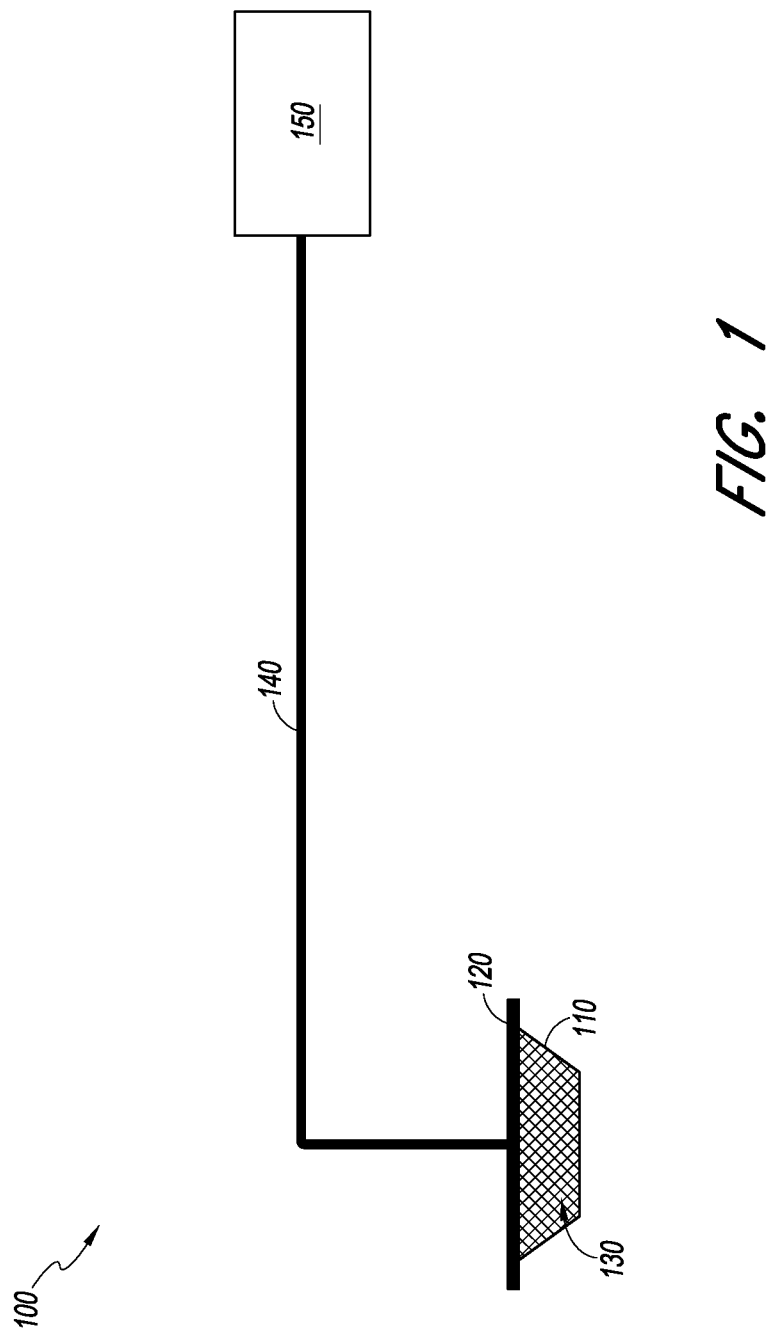
FIG. 1 illustrates a negative pressure wound therapy system according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below. Moreover, the features of this disclosure can be incorporated or implemented in other wound therapy apparatuses, such as positive pressure therapy devices, or other medical apparatuses usable for treating a patient.

TNP therapy can assist in the closure and healing of many forms of "hard to heal" wounds by reducing tissue oedema, encouraging blood flow and granular tissue formation, or removing excess exudate and can reduce bacterial load (and thus infection risk). In addition, TNP therapy may allow for less disturbance of a wound leading to more rapid healing. TNP systems can also assist in the healing of surgically closed wounds by removing fluid or help to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Overview

In some instances, updates to labelling for a TNP apparatus may be desirable or needed. For example, a label can be updated when an indication of use for the TNP apparatus may be added or changed or when a change may occur in the standards that the TNP apparatus is expected or required to meet (for instance, IEC 60601-1, FCC, etc., as well as if the device is released or operated in a new country with particular compliance rules).

It may be difficult, in some instances, to ensure that a patient is reliably provided up-to-date labelling for a TNP apparatus. For example, the ability of a TNP apparatus to receive and present an updated label may be limited or not dependable. Some features disclosed herein address this technical difficulty by facilitating a TNP apparatus to direct another electronic device to quickly access and present an up-to-date label and thereby relieving the TNP apparatus from the burden of having to provide the up-to-date label. Advantageously, in certain embodiments, these features can reduce the memory or hardware requirements for a TNP apparatus because the TNP apparatus can enable access to the up-to-date label but not itself receive or present the up-to-date label. Moreover, this may increase the robustness and security of a TNP apparatus because the TNP apparatus may not be susceptible to receiving malicious or improper code via an update to label information for the TNP apparatus.

Moreover, some features disclosed herein relate to approaches for making a TNP apparatus more responsive and intelligent when handling various conditions or environments.

Wound Therapy System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected to the wound cover 120 with a TNP apparatus 150 configured to supply reduced pressure. The wound cover 120 can be in fluidic communication with the wound cavity 110. In any of the system embodiments disclosed herein, as in the embodiment illustrated in FIG. 1, the TNP apparatus can be a canisterless TNP apparatus (meaning that exudate is collected in the wound dressing or is transferred via tube 140 for collection to another location). However, any of the TNP apparatus embodiments disclosed herein can be configured to include or support a canister. Additionally, in any of the system embodiments disclosed herein, any of the TNP apparatus embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renasys Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the TNP apparatus 150 and the wound cover 120, so as to supply the reduced pressure provided by the TNP apparatus 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the TNP apparatus 150. The TNP apparatus 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the TNP apparatus 150 and tubing 140 so that the tubing 140 can be quickly and easily removed from the TNP apparatus 150 can facilitate or improve the process of dressing or pump changes, if necessary. Any of the pump embodiments disclosed herein can be configured to have any suitable connection between the tubing and the pump.

The TNP apparatus 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the TNP apparatus 150.

In operation, the wound filler 130 is inserted into the wound cavity 110 and wound cover 120 is placed so as to seal the wound cavity 110. The TNP apparatus 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the TNP apparatus and other embodiments of the present application include Renasys-F, Renasys-G, Renasys Aft and Pico Dressings available from Smith & Nephew. Further description of such wound dressings and other components of a negative pressure wound therapy system that may be used with the TNP apparatus and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Figure 2A:
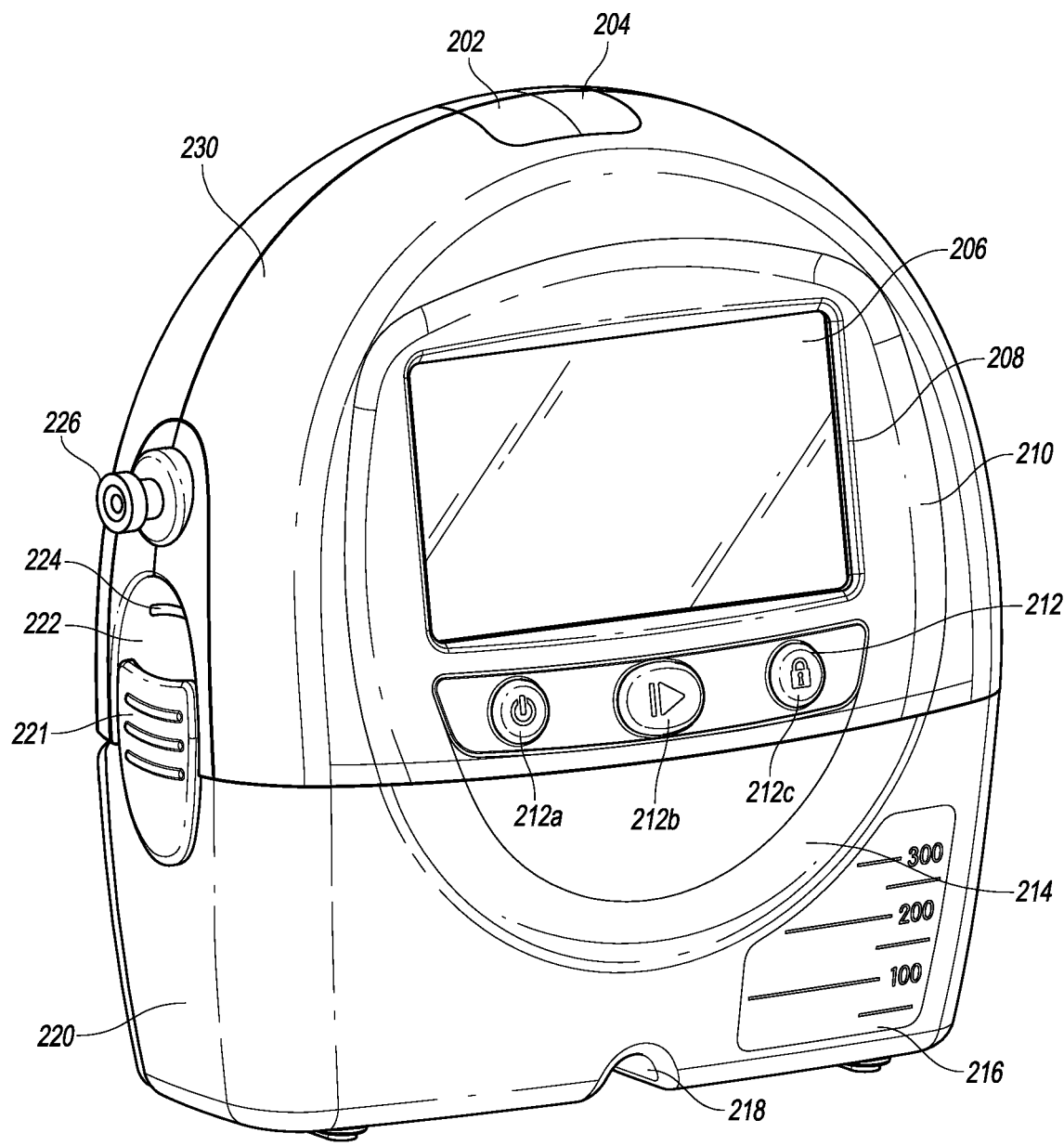
FIGS. 2A, 2B, and 2C illustrate a TNP apparatus according to some embodiments.

FIG. 2A illustrates a front view of a pump assembly 230 and canister 220 according to some embodiments. As is illustrated, the pump assembly 230 and the canister 220 are connected, thereby forming a TNP apparatus. The pump assembly 230 can be similar to or the same as the TNP apparatus 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons configured to allow the user to operate and monitor the operation of the TNP system. As is illustrated, there buttons 212a, 212b, and 212c (collectively referred to as buttons 212) are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
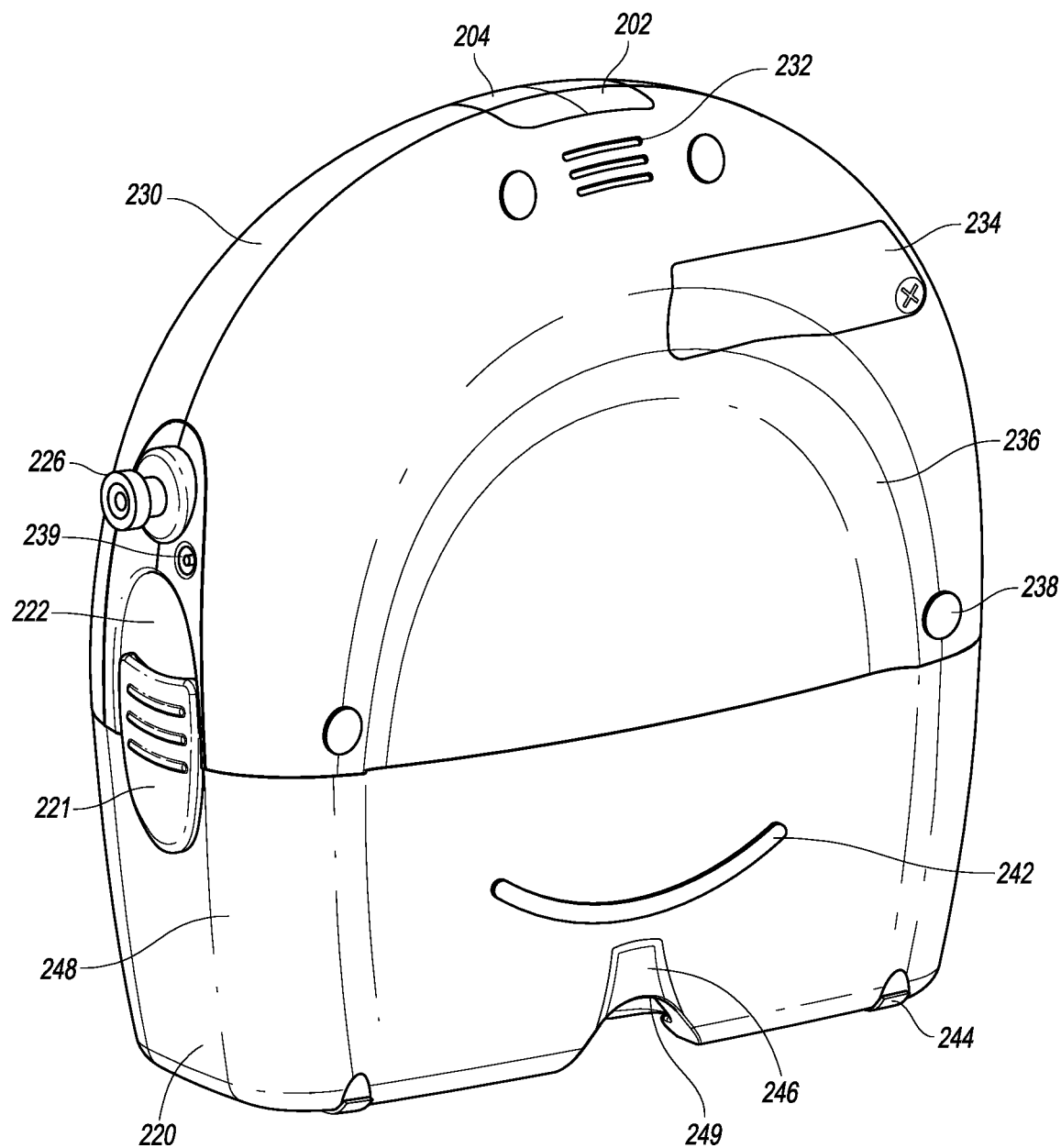

FIG. 2B illustrates a rear view of the pump assembly 230 and canister 220 according to some embodiments. The pump assembly 230 comprises a speaker port 232 for producing sound. The pump assembly 230 includes a filter access door 234 with a screw for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
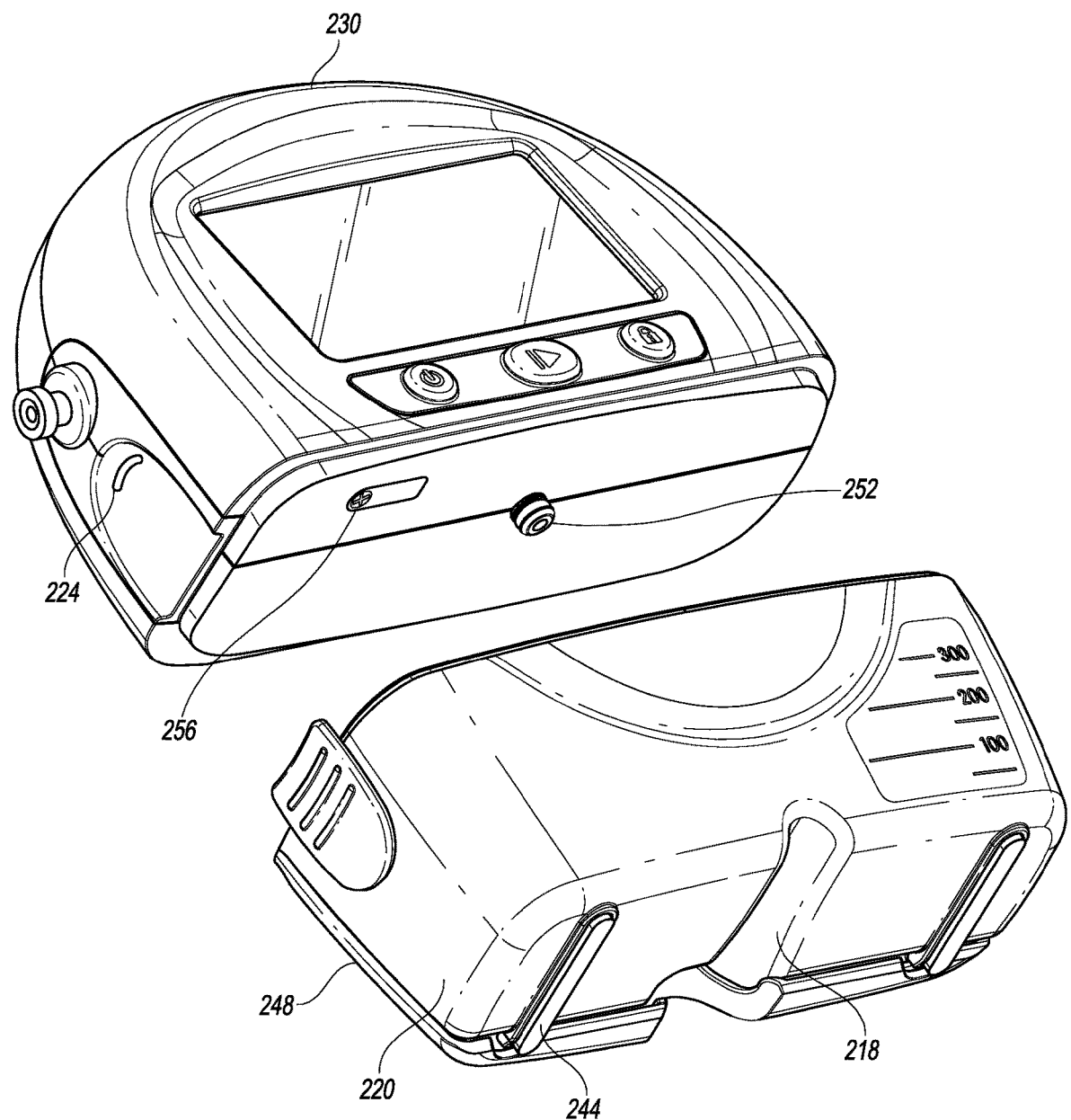

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, or hybrid data transfer interfaces, such as SD, Compact Disc (CD), DVD, FireWire, Thunderbolt, PCI Express, and the like. In other embodiments, one or more of these additional ports are accessed through the door 234.

Figure 3A:
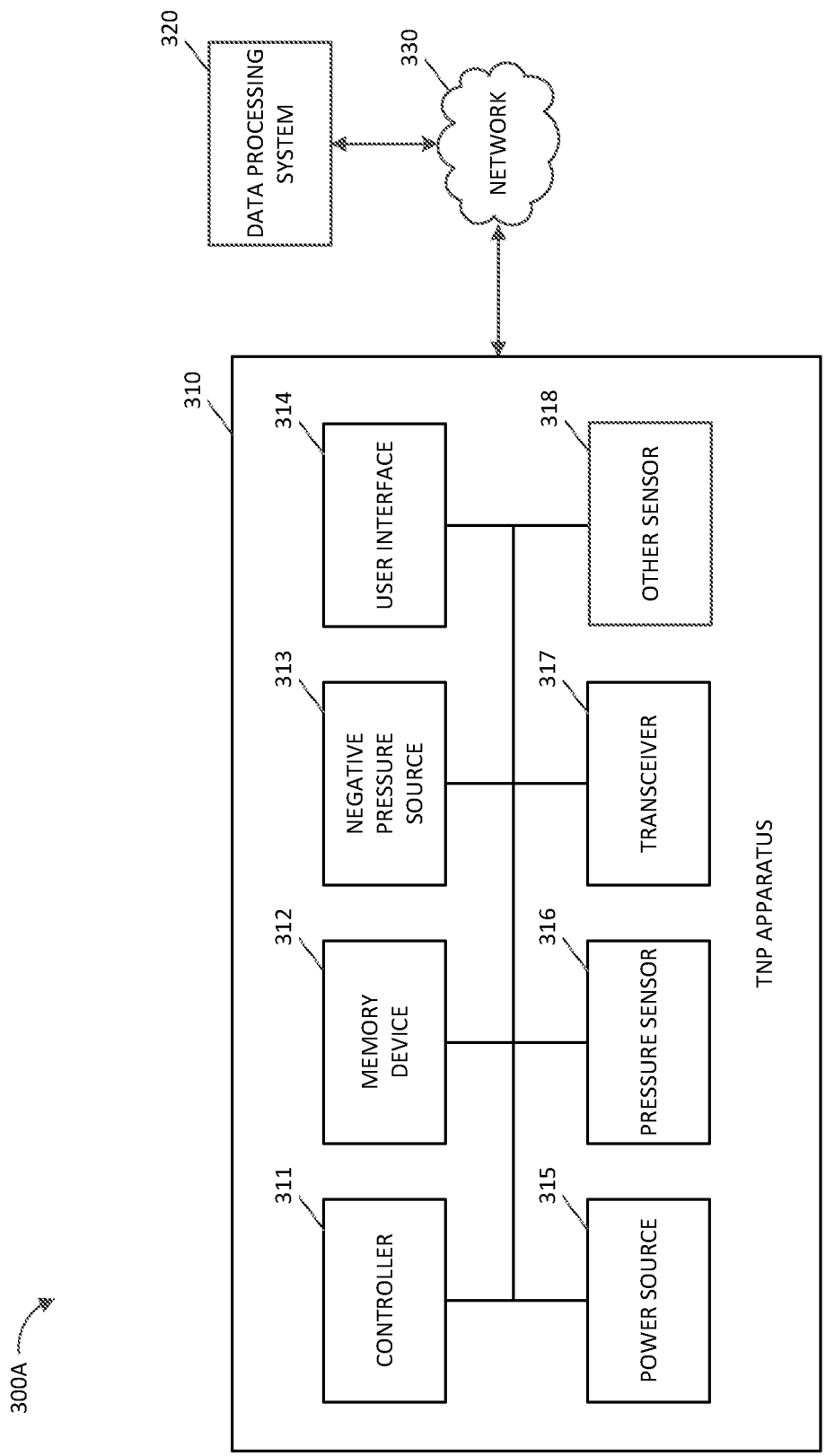
FIGS. 3A, 3B, 3C, 3D, 3E, 3F, and 3G illustrate components of a negative pressure therapy system according to some embodiments.

FIG. 3A illustrates components of a negative pressure therapy system 300A that includes a TNP apparatus 310 and a remote data processing system 320 according to some embodiments. The TNP apparatus 310 can be used to treat a wound using a wound dressing that is in fluidic communication with the TNP apparatus 310 via a fluid flow path. The TNP apparatus 310 can include a controller 311, a memory device 312, a negative pressure source 313, a user interface 314, a power source 315, a pressure sensor 316, a transceiver 317, and one or more other sensors 318 that are configured to electrically communicate with one another. The power source 315 can provide power to one or more components of the TNP apparatus 310. The TNP apparatus 310 can operate at the pressure levels and using control approaches as described herein or similar to those described in U.S. Patent Publication Nos. 2016/0136339 and 2016/0184496, which are incorporated by reference in their entirety. The TNP apparatus 310 can be similar to or the same as the TNP apparatus 150 in some embodiments.

The controller 311 can control operations of one or more other components of the TNP apparatus 310 according at least to instructions stored in the memory device 312. The controller 311 can, for instance, control operations of and supply of negative pressure by the negative pressure source 313. The negative pressure source 313 can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combinations of the foregoing.

The user interface 314 can include one or more elements that receive user inputs or provide user outputs to a patient or caregiver. The one or more elements that receive user inputs can include buttons, switches, dials, touch screens, or the like. The user interface 314 can, for example, be used to generate and display a report or other information reflecting data from therapy use, data from non-compliant use, or a comparison of data from therapy use versus non-compliant use. As another example, the user interface 314 may receive a user input providing a patient reference number or another unique identifier, and the TNP apparatus 310 may then be activated for use by the patient and data collected and stored as described herein may be associated with the patient reference number for usage monitoring for a particular patient. The user interface 314 can also provide an alert to the user. For example, the user interface 314 can include a screen that may visibly present the alert or a speaker that may audibly present the alert.

Figure 3B:
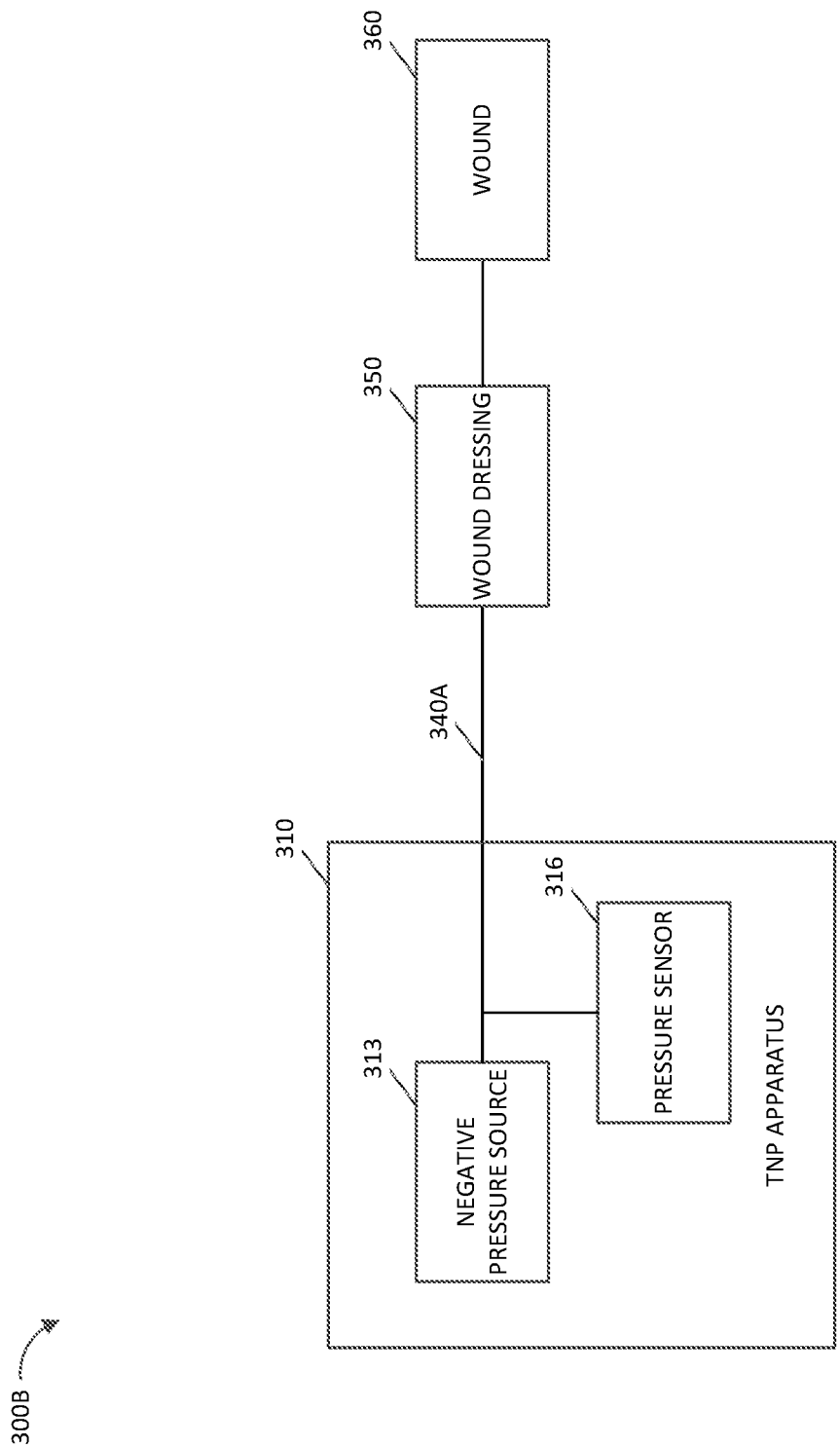
Figure 3C:
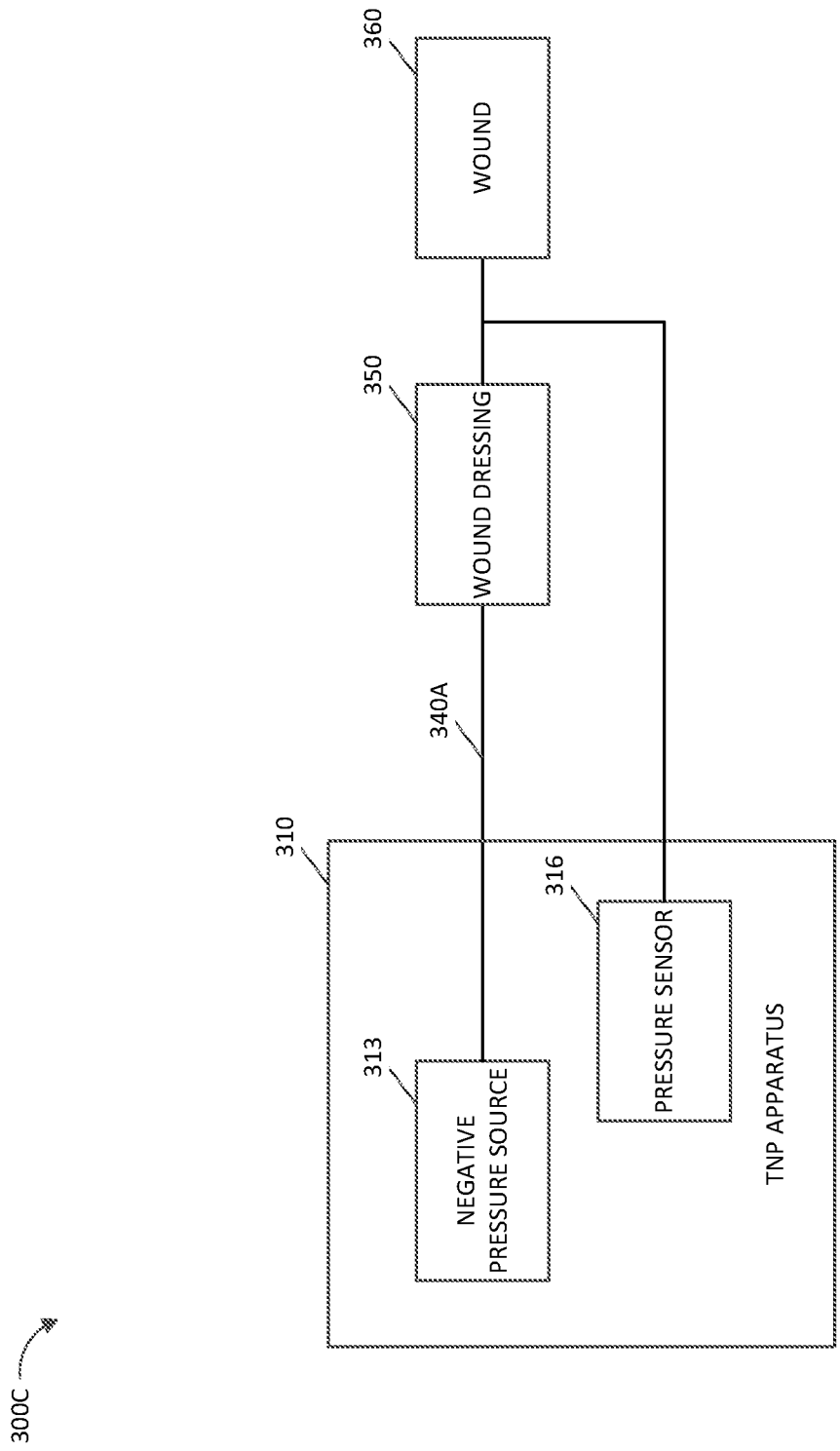
Figure 3D:
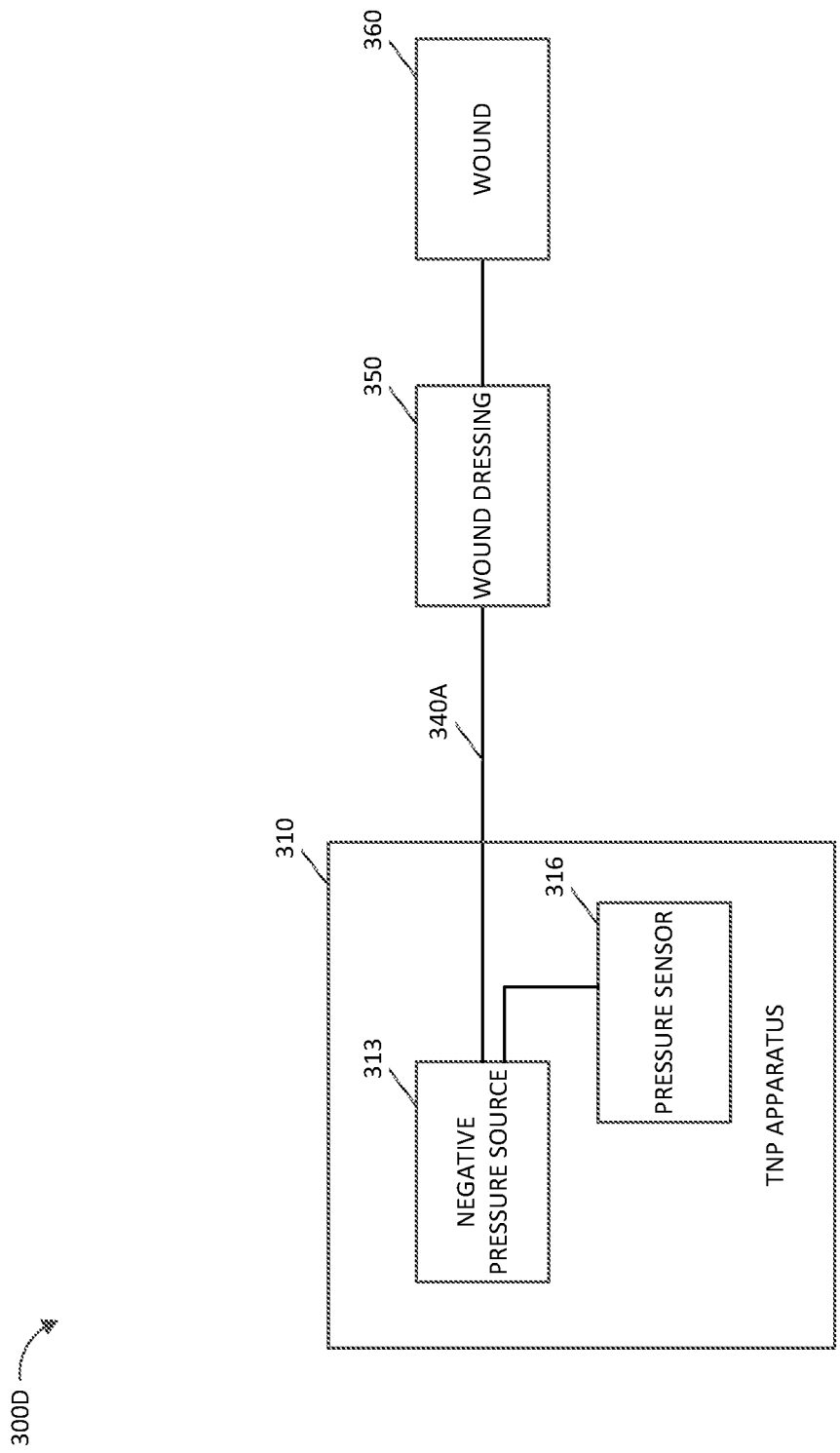

The pressure sensor 316 can be used to monitor pressure underneath a wound dressing, such as (i) pressure in a fluid flow path connecting the negative pressure source 313 and the wound dressing as illustrated by FIG. 3B, (ii) pressure at the wound dressing as illustrated by FIG. 3C, or (iii) pressure at or in the negative pressure source 313 as illustrated by FIG. 3D. As the negative pressure source 313 provides negative pressure, the negative pressure source 313 may generate pressure pulses that are propagated through the fluid flow path and detected by the pressure sensor 316. These pressure pulses may show as a change or bounce in the magnitude or frequency of a signal from the pressure sensor 316.

The controller 311 can analyze a signal output by the pressure sensor 316 to determine pressure in the fluid flow path. The controller 311 may examine the signal using one or more approaches including time domain or frequency domain calculations, such as with a digital signal processor.

The controller 311 or other circuitry of the TNP apparatus 310 may process one or more signals output by the pressure sensor 316 by filtering out noise and then dynamically amplifying the filtered one or more signals. Dynamic amplification can be performed without filtering. This may enable the features described herein to be applied to smaller wounds or weaker pressure signals. For example, the amplification can be performed by a programmable gain amplifier, which may be controlled by software or hardware.

The detection of pressure by the pressure sensor 316 can, in some instances, be enhanced by changing one or more settings of the negative pressure source 313, such as increasing or decreasing vacuum level delivered by the negative pressure source 313, stopping the negative pressure source 313, changing an operating speed of the negative pressure source 313, changing a cadence of the negative pressure source 313, combinations of the same, or the like. The controller 311 can, for example, automatically manage adjustment of the one or more settings.

Figure 3E:
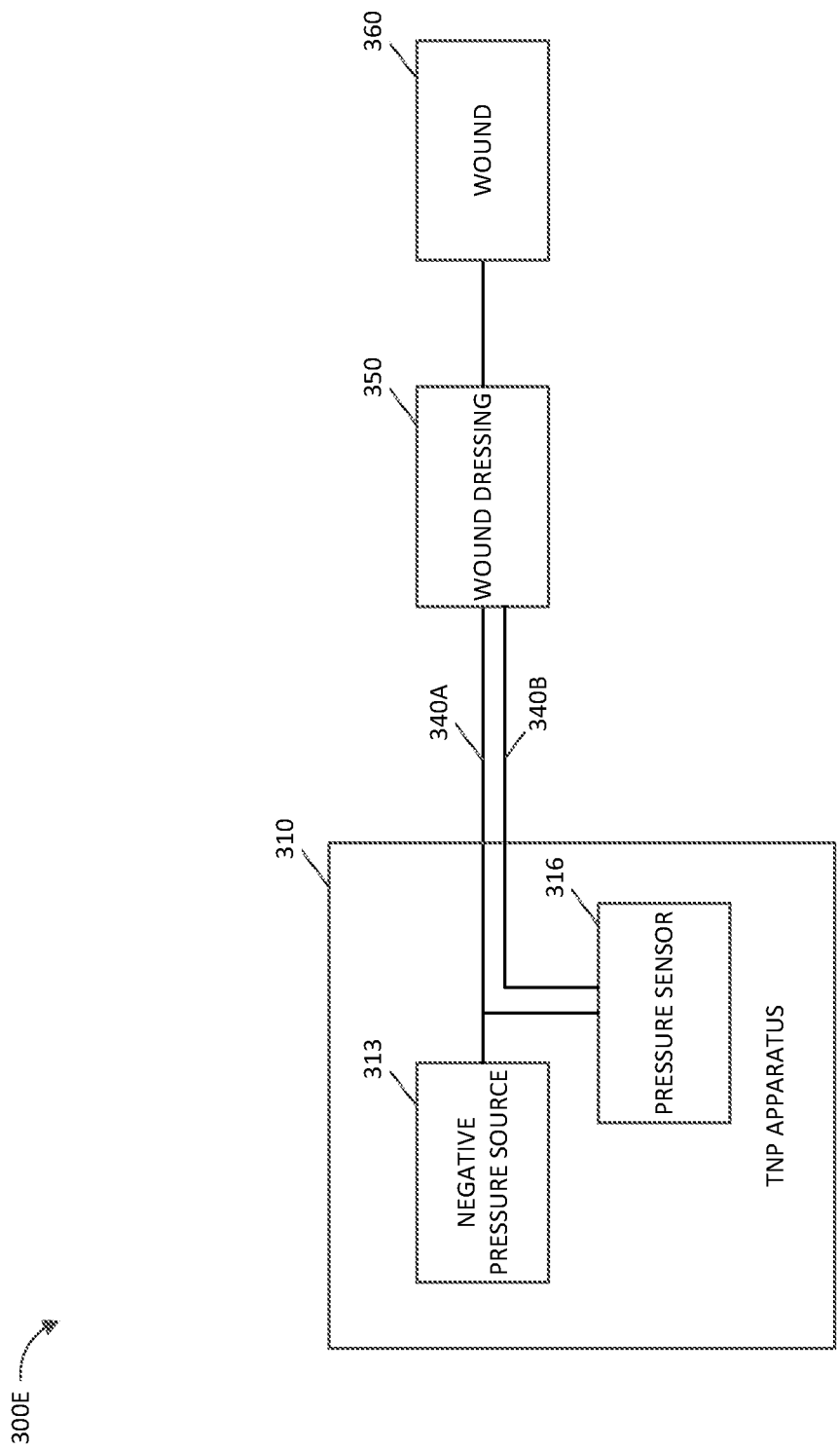

In some implementations, the pressure sensor 316 can be used in combination with another pressure sensor so that the at least two pressure sensors that are positioned in or fluidically connected to the fluid flow path to permit differential measurement of the pressure, such as illustrated by FIG. 3E. For example, a first pressure sensor can be positioned upstream of the wound (such as at or near the inlet of the negative pressure source 313C) and a second pressure sensor can be positioned to detect pressure at or near the wound or at or near a canister. This configuration can be accomplished by incorporating, in addition to one or more lumens forming a first fluid flow path connecting the negative pressure source 313 to the wound, a second fluid flow path that includes one or more lumens connecting the TNP apparatus 310 to the wound and through which the second pressure sensor can monitor pressure at or near the wound or at or near a canister. The first and second fluid flow paths can be fluidically isolated from each other. When the at least two pressure sensors are used, the rate of change of pressure (for example, in peak-to-peak pressure or maximum pressure) in the first and second fluid flow paths can be determined and the difference in pressure detected between the first and second pressure sensors can be determined. These values can be used separately or together to detect various operational conditions, such as leaks, blockages, canister full, presence of blood in the first fluid flow path or the second fluid flow path, etc. In some implementations, multiple redundant pressure sensors can be provided to protect against failure of one or more of the pressure sensors.

The transceiver 317 can be used to communicate with the data processing system 320 via a network 330. The transceiver 317 can, for example, transmit device usage data like alarms, measured pressure, or changes to a therapy program administered by the TNP apparatus 310 to the data processing system 320. The network 330 can be a communication network, such as a wireless communications network like a cellular communications network. The memory device 312 can be used to store the device usage data that may be transmitted by the transceiver 317.

The one or more other sensors 318 can be or include one or more motion sensors (for example, an accelerometer, gyroscope, inertial measurement unit, or orientation detector). The TNP apparatus 310 can adjust its operation according to one or more outputs from the one or more other sensors 318. The one or more other sensors 318 can be attached to an outside of a housing of the TNP apparatus 310. The one or more other sensors 318 can be removable, such that it can be interchangeably replaced with another type sensor. Additionally or alternatively, the one or more other sensors 318 can be positioned or placed within a housing of the TNP apparatus 310.

The one or more other sensors 318 can detect multiple parameters, such as acceleration in x, y, z direction or an angle between the orientation of the TNP apparatus 310 and the direction of gravity. Further, by taking measurement multiple times within an interval, the one or more other sensors 318 may provide information about a change in acceleration in x, y, z direction or change in angle between the orientation of the TNP apparatus 310 and the direction of gravity. In some implementations, the one or more other sensors 318 can take measurement 50 times per second, more than 50 times per second, more than 100 times per second, or more than 200 time per second. If data is taken more frequently, a change in acceleration or orientation may be calculated more accurately. The one or more other sensors 318 can communicate sensor data wirelessly, such as via Bluetooth® protocol, to the controller 311 or other components of the TNP apparatus 310.

The output from the one or more other sensors 318 can provide information about various conditions of or situations around the TNP apparatus 310 such that the TNP apparatus 310 may operate depending on such conditions or situations. For example, from the output of the one or more other sensors 318, the TNP apparatus 310 can be determined to be oriented upside-down, shocked, used by a user that may be walking, or positioned within a vehicle or an airplane.

The controller 311 can analyze a signal output by the one or more sensors 318, such as the one or more motion sensors, to determine a motion or orientation of the device as described herein.

The data processing system 320 can, in some implementations, analyze pressure data received from the transceiver 317 to determine whether the received pressure data is indicative of the negative pressure source 313 being in use on a patient, such as using analysis approaches as described with respect to the TNP apparatus 310. The data processing system 320 can, for instance, generate and display a report or other information reflecting data from therapy use, data from non-compliant use, or a comparison of data from therapy use versus non-compliant use. In one example, a user of the data processing system 320 may input a patient reference number or TNP apparatus number associated with a TNP apparatus, and the data processing system 320 can then provide or display data like data from therapy use or data from non-compliant use for the patient reference number or TNP apparatus number.

FIG. 3B illustrates a negative pressure therapy system 300B that includes the TNP apparatus 310 of FIG. 3A, as well as a first fluid flow path 340A, a wound dressing 350, and a wound 360 according to some embodiments. The TNP apparatus 310 can be used to treat the wound 360 using the wound dressing 350 that is in fluidic communication with the negative pressure source 313 via the first fluid flow path 340A. In particular, FIG. 3B depicts that the pressure sensor 316 can be positioned in the first fluid flow path 340A, such as at or near an inlet of the TNP apparatus 310, to measure pressure in the first fluid flow path 340A.

FIG. 3C illustrates a negative pressure therapy system 300C that differs from the negative pressure therapy system 300B in that the pressure sensor 316 can instead be positioned to measure pressure at or near the wound dressing 350, such as pressure underneath the wound dressing 350 when the wound dressing 350 is coupled to the wound 360.

FIG. 3D illustrates a negative pressure therapy system 300D that differs from the negative pressure therapy system 300B in that the pressure sensor 316 can instead be positioned to measure pressure at the negative pressure source 313. In one example, the pressure sensor 316 can be a part of and within the negative pressure source 313 to measure pressure generated by the negative pressure source 313. In another example, the pressure sensor 316 can be separate from the negative pressure source 313 and positioned to measure pressure at or near an inlet of the negative pressure source 313.

FIG. 3E illustrates a negative pressure therapy system 300E that differs from the negative pressure therapy system 300B in that the negative pressure therapy system 300E further includes a second fluid flow path 340B, and the pressure sensor 316 can be a differential pressure sensor or include two pressure sensors. If the pressure sensor 316 may include the two pressure sensors, one of the two pressure sensors of the pressure sensor 316 can be positioned in the first fluid flow path 340A to measure pressure in the first fluid flow path 340A, and the other of the two pressure sensors the pressure sensor 316 can be positioned in the second fluid flow path 340B to measure pressure in the second fluid flow path 340B. If the pressure sensor 316 may be the differential pressure sensor, the pressure sensor 316 can be fluidically connected to the first fluid flow path 340A and the second fluid flow path 340B. The first fluid flow path 340A can thus be used by the negative pressure source 313 to provide negative pressure to the wound dressing 350, and the second fluid flow path 340B can be used primarily by the pressure sensor 316 to measure pressure at or near the wound dressing 350, such as under the wound dressing 360. The pressure sensor 316 can thereby be used by the TNP apparatus 310 to perform differential measurement of pressure between pressure supplied by the negative pressure source 313 and pressure at or near the wound dressing 350.

Figure 3F:
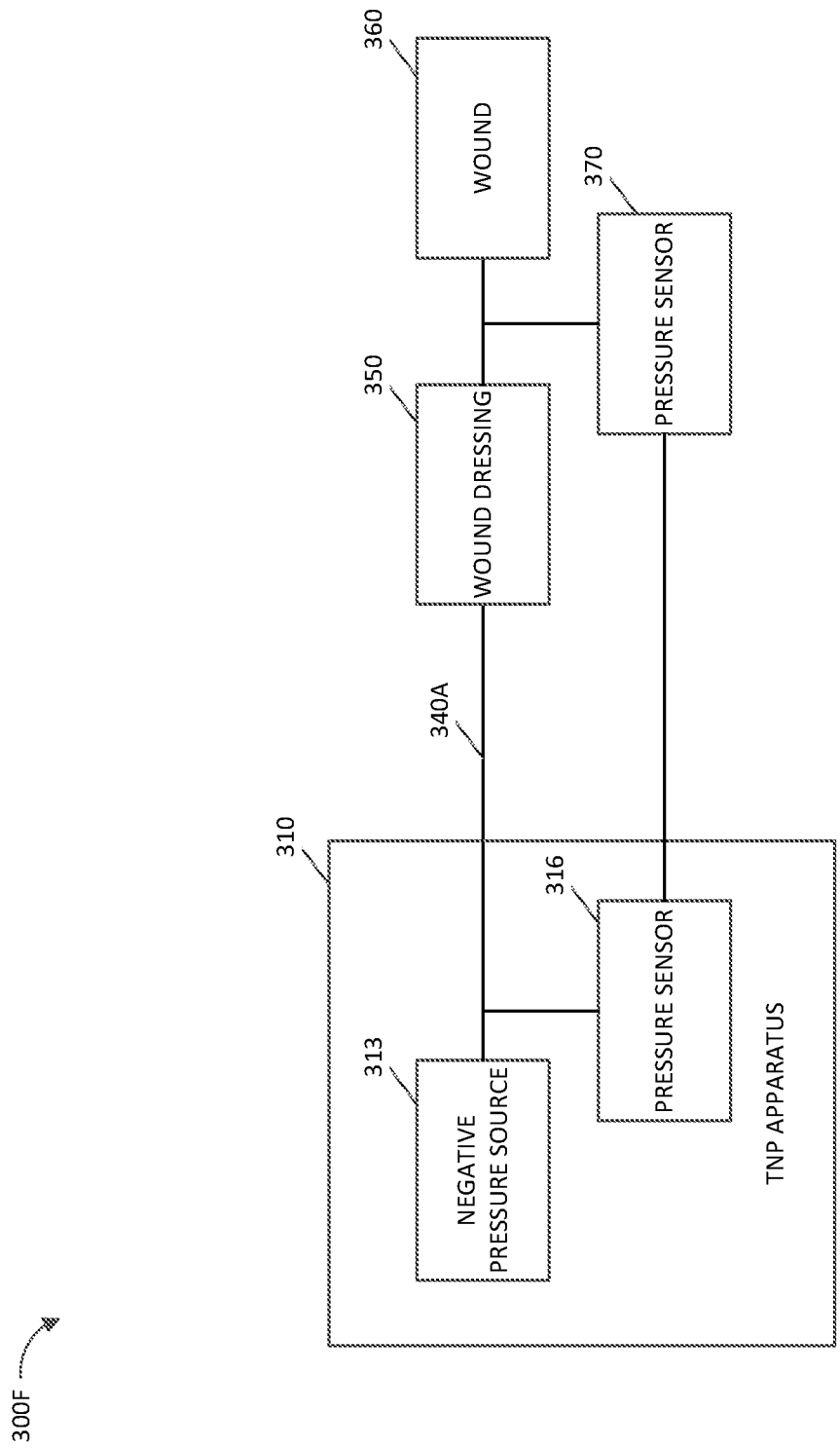

FIG. 3F illustrates a negative pressure therapy system 300F that differs from the negative pressure therapy system 300B in that the negative pressure therapy system 300F can further include an additional pressure sensor 370 positioned to measure pressure at or near the wound dressing 350, such as pressure underneath the wound dressing 350 when the wound dressing 350 is coupled to the wound 360. The additional pressure sensor 370 can generate and output a signal to the TNP apparatus 310 responsive to the pressure measured at the wound dressing 350. The pressure sensor 316 and the additional pressure sensor 370 can thus be used by the TNP apparatus 310 to perform differential measurement of pressure between pressure supplied by the negative pressure source 313 and pressure at or near the wound dressing 350.

Figure 3G:
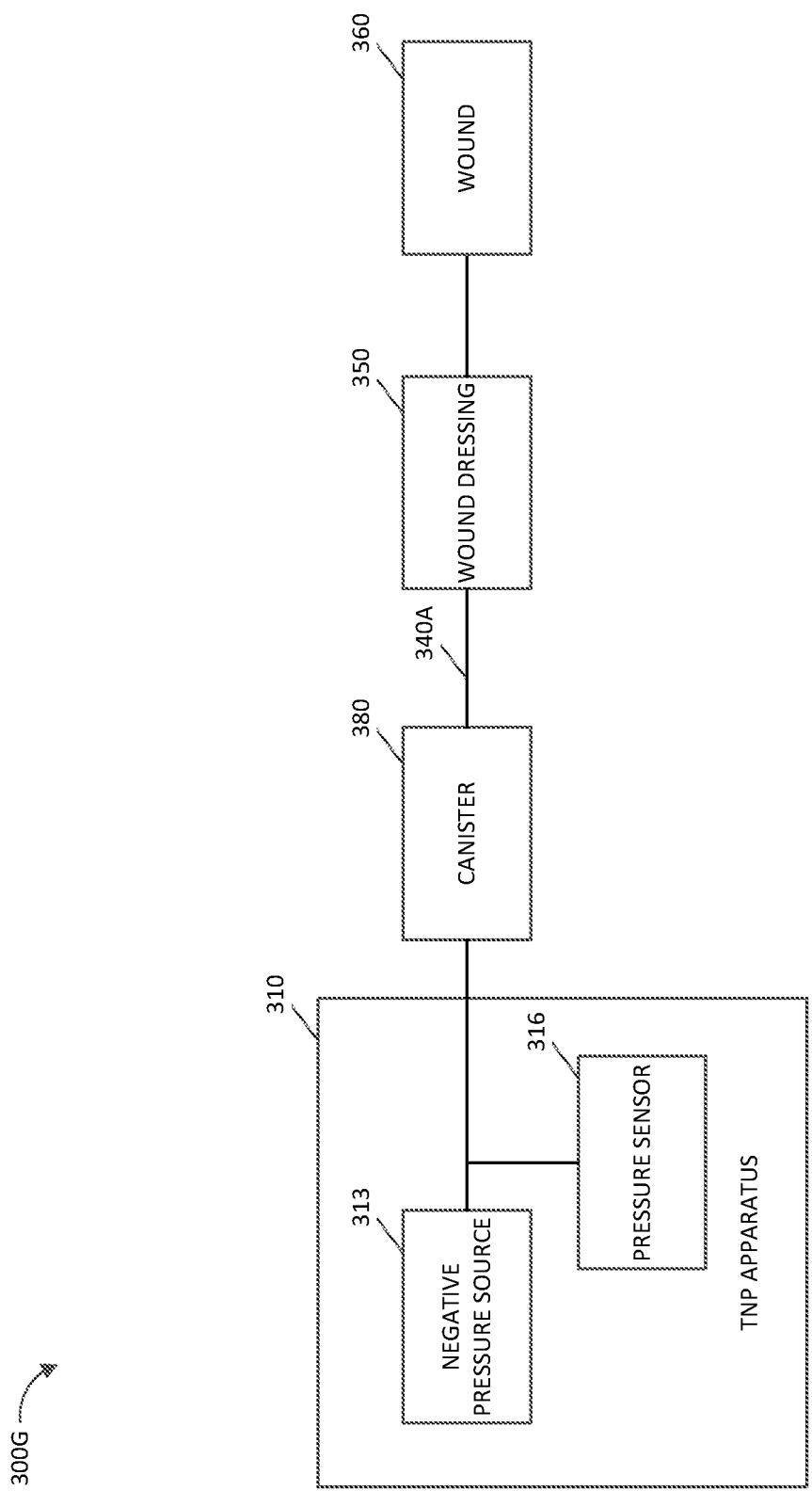

FIG. 3G illustrates a negative pressure therapy system 300G that differs from the negative pressure therapy system 300B in that a canister 380 can be coupled between the negative pressure source 313 and the wound dressing 350 in the first fluid flow path 340A. The canister 380 can collect exudate removed from the wound 360. The examples of FIGS. 3C-3F can be similarly modified to also include the canister 380, in some implementations.

Figure 4:
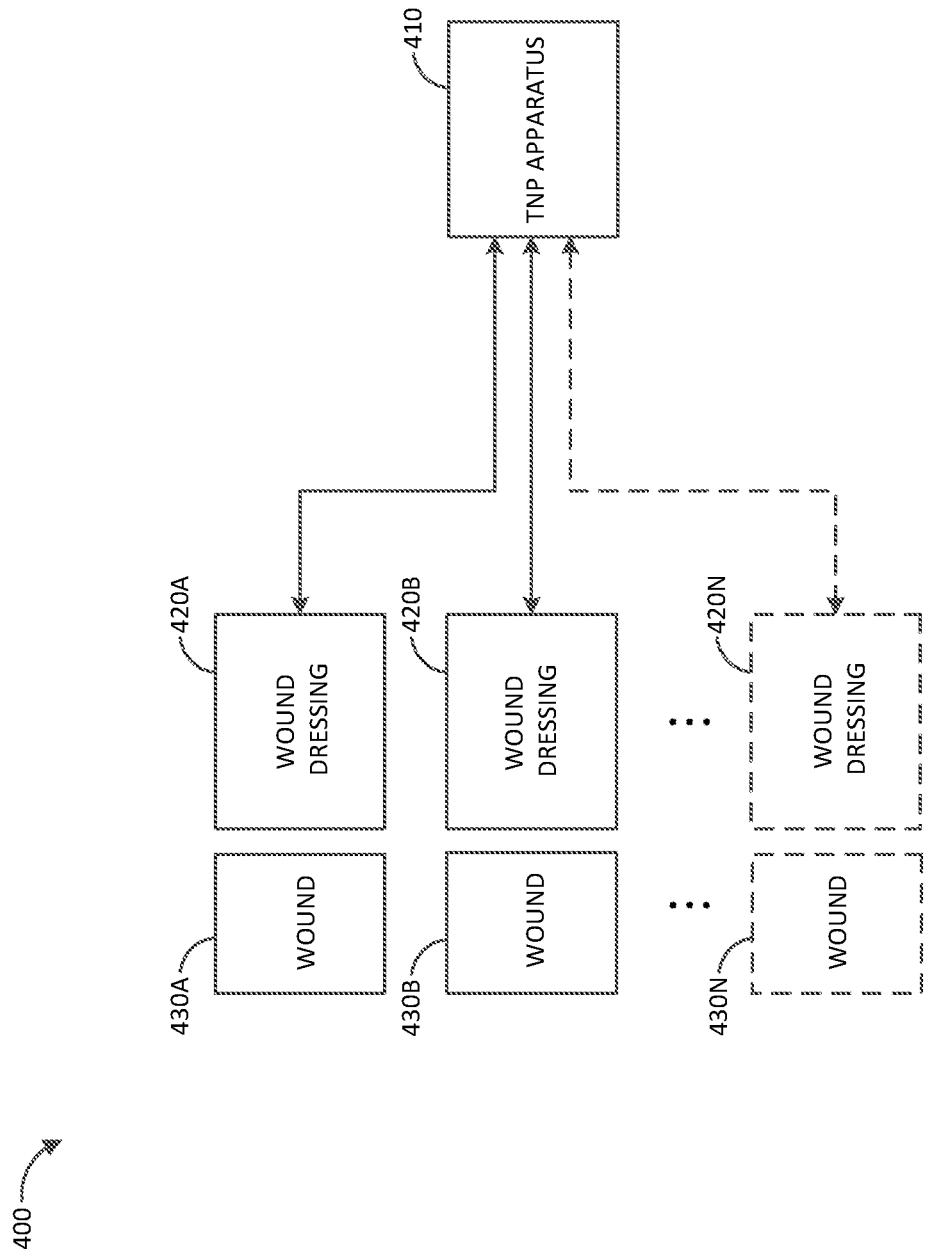
FIG. 4 illustrates components of a negative pressure therapy system that includes multiple wound dressings according to some embodiments.

FIG. 4 illustrates a negative pressure therapy system 400 that includes a TNP apparatus 410 and wound dressings 420A, 420B, . . . , 420N according to some embodiments. The wound dressings 420A, 420B, . . . , 420N can be in fluidic communication with the TNP apparatus 410 and each be used to treat a different wound of wounds 430A, 430B, . . . , 430N on a patient. The TNP apparatus 410 can be similar to or the same as the TNP apparatus 310 in some embodiments.

The TNP apparatus 310 can separately monitor each of the wound dressings 420A, 420B, . . . , 420N so that the TNP apparatus 310 is able to generate an alarm for a subset of the wounds 430A, 430B, . . . , 430N (for instance, one, two, or three of the wounds) without having to generate an alarm for the one or more other of the wounds 430A, 430B, . . . , 430N. As a result, control can be consolidated with the TNP apparatus 310 and multiple TNP apparatuses may not be used for treating the wounds 430A, 430B, . . . , 430N.

In yet further implementations, the negative pressure therapy system 400 can include two of the TNP apparatus 410 where the two of the TNP apparatus 410 communicate with one another to facilitate treatment of more wounds. The negative pressure therapy system 400 in some such implementations may also include a central hub device (not shown) that operates one or both of the TNP apparatus 410 and provides a communication interface for the two of the TNP apparatus 410 through which the two of the TNP apparatus 410 communicate.

Figure 5:
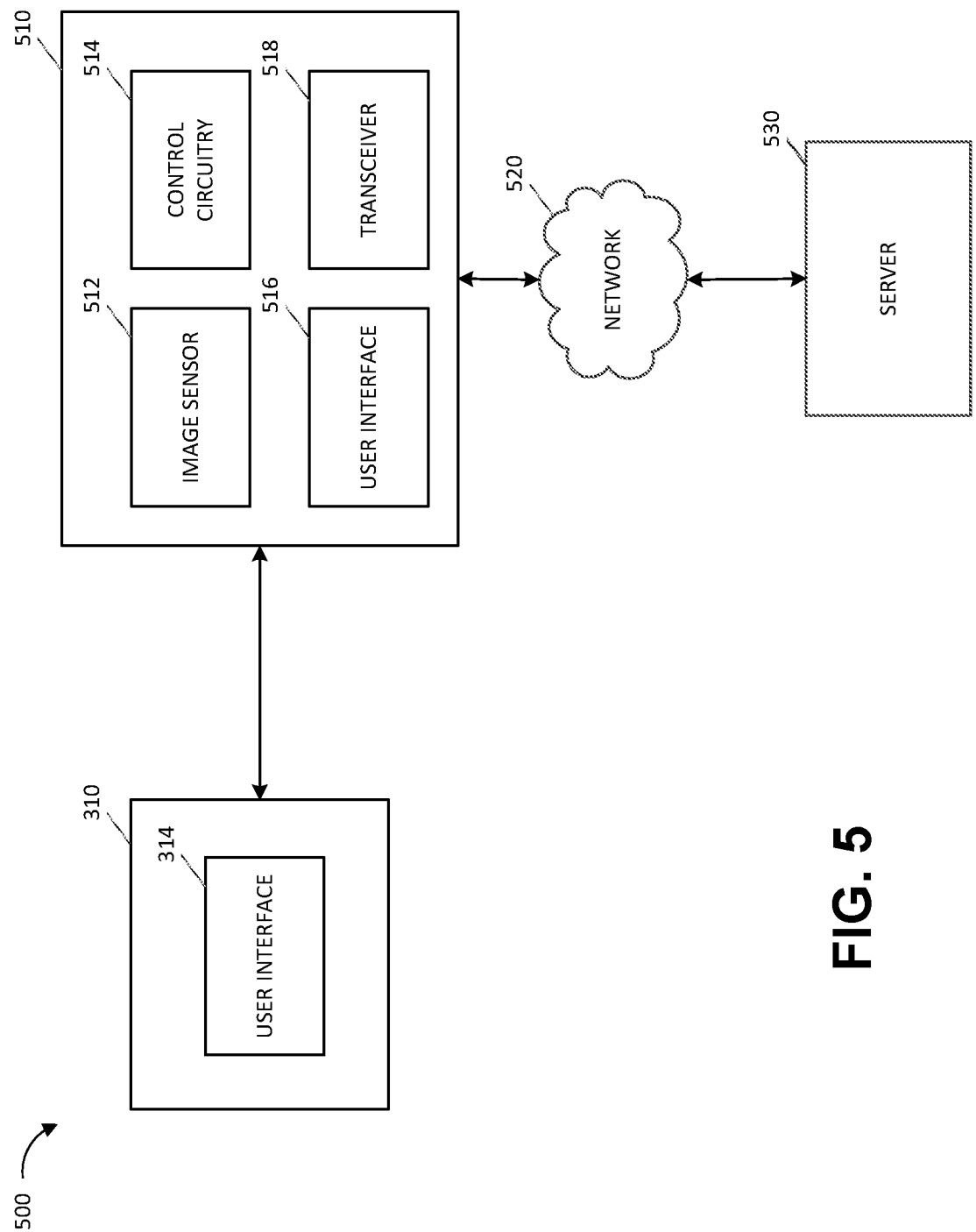
FIGS. 5 and 6 illustrate communications within negative pressure wound therapy systems according to some embodiments.

FIG. 5 illustrates communications within a negative pressure wound therapy system 500 according to some embodiments. The negative pressure wound therapy system 500 includes the TNP apparatus 310 of FIG. 3, as well as an electronic device 510 and a server 530. The TNP apparatus 310 can communicate with the electronic device 510 wirelessly, such as via electromagnetic radiation like optical radiation (for example, light visible to a person). The electronic device 510 can, in turn, wirelessly communicate with the server 530 via a network 520, such as a computer network. The electronic device 510 can, for example, be a smart phone, tablet, personal computer, or the like.

The electronic device 510 can include an image sensor 512, control circuitry 514, a user interface 516, and a transceiver 518. The image sensor 512 can be configured to detect optical radiation, such as in the form of a barcode, displayed by the user interface 314. The control circuitry 514 can process the optical radiation from the user interface 314 and determine to communicate with the server 530 via the network 520 using the transceiver 518. The user interface 316 can be used to display information, such as a label for the TNP apparatus 310, received from the server 530. Moreover, operations of the electronic device 510 and the TNP apparatus 310 can be controlled by a user via the user interface 516.

Figure 6:
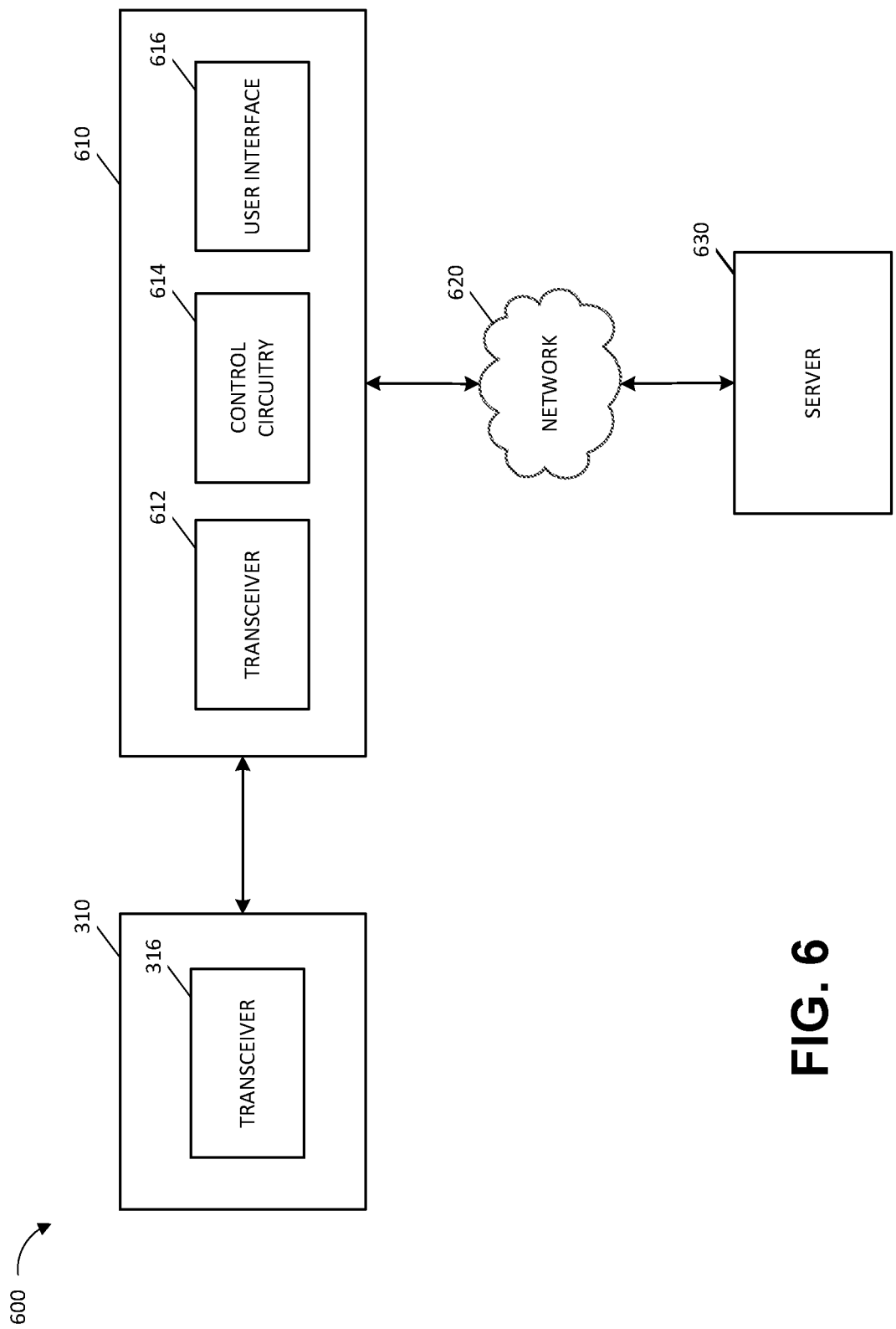

FIG. 6 illustrates communications within a negative pressure wound therapy system 600 according to some embodiments. The negative pressure wound therapy system 600 includes the TNP apparatus 310 of FIG. 3, as well as an electronic device 610 and a server 630. The negative pressure wound therapy system 600 can be similar to the negative pressure wound therapy system 500; however, the TNP apparatus 310 and the electronic device 610 can be configured to communicate via the transceiver 316 and a transceiver 612 of the electronic device 610 using ultra high frequency (UHF) radiation (for example, around 2.4 GHz radiation) or super high frequency (SHF) radiation (for example, around 5 GHz radiation) rather than optical radiation. The transceiver 316 and the transceiver 612 can, for instance, communicate via data packets and using a communication protocol, such as Bluetooth. The electronic device 610, the network 620, and the server 630 may otherwise operate similarly respectively to the electronic device 510, the network 520, and the server 530, and the transceiver 612 can communicate via the network 620 with the server 530. Control circuitry 614 of the electronic device 610 can be used to display information, such as a label for the TNP apparatus 310, received from the server 630, and operations of the electronic device 610 and the TNP apparatus 310 can be controlled by a user via the user interface 616.

Figure 7:
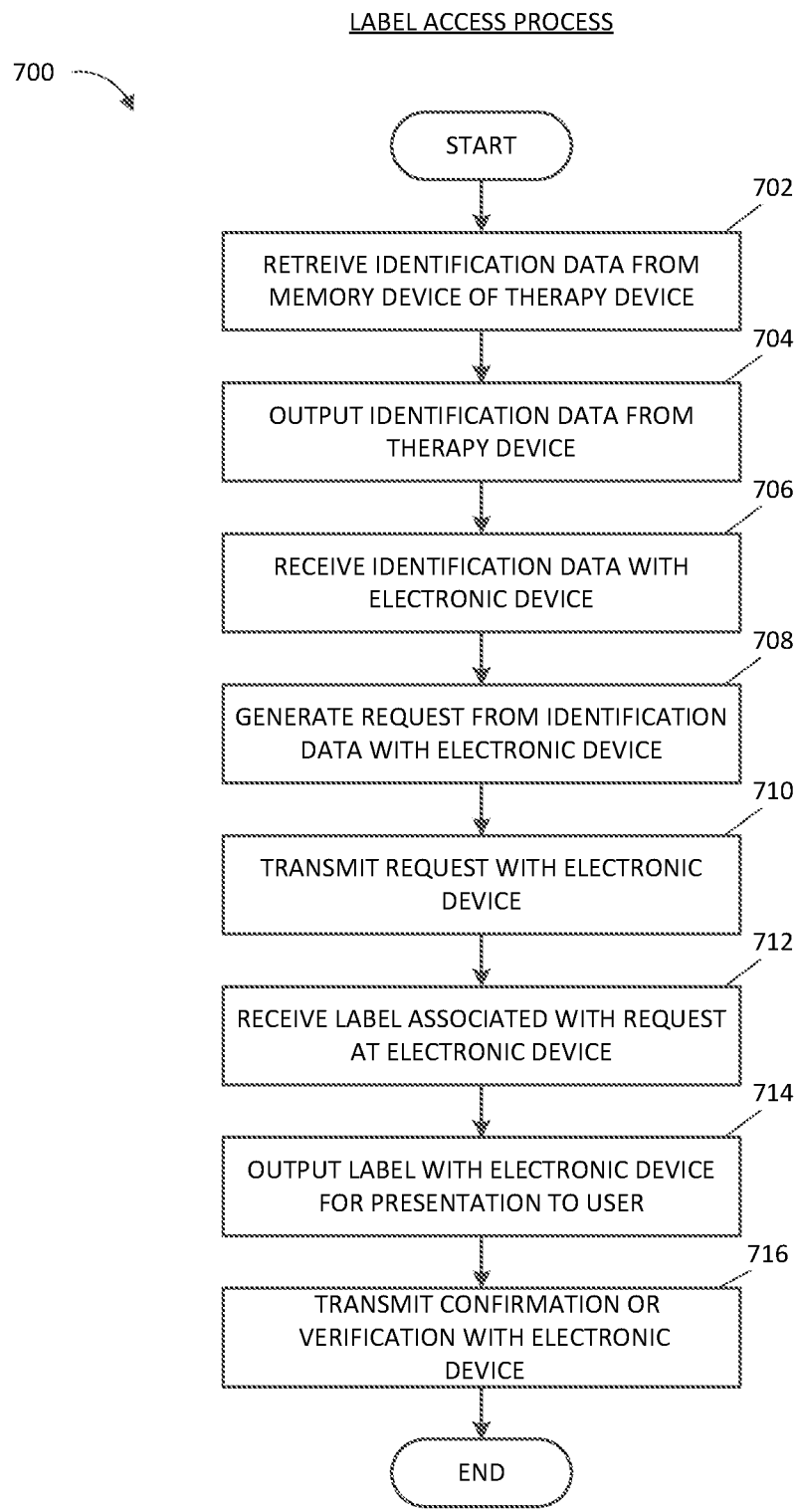
FIG. 7 illustrates a label access process according to some embodiments.
Figure 8A:
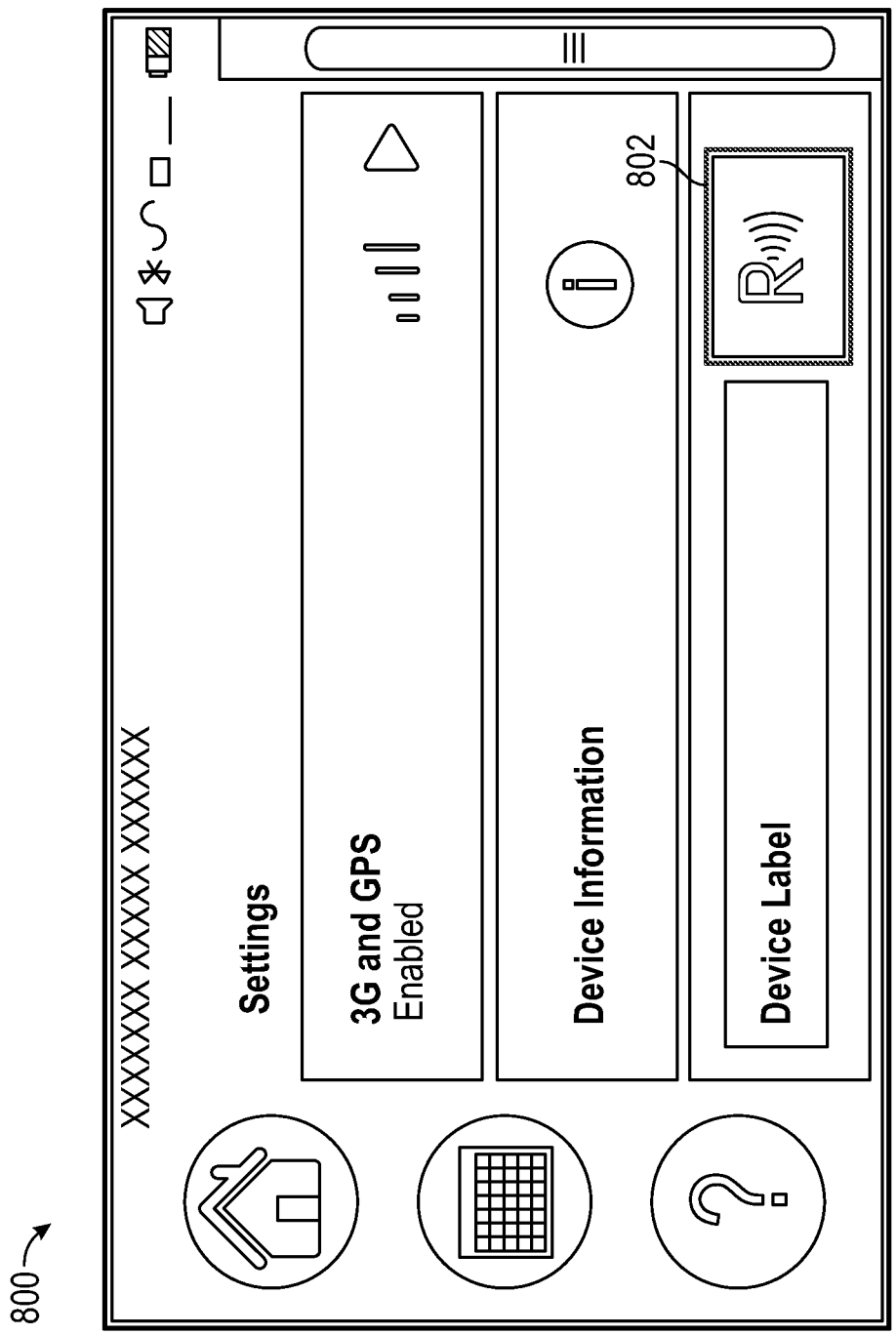
FIGS. 8A, 8B, 8C, and 8D illustrate user interfaces for managing a label access process and performing other operations according to some embodiments.

FIG. 7 illustrates a label access process 700 according to some embodiments. The label access process 700 can be performed by a therapy system, such as the negative pressure wound therapy system 500 or the negative pressure wound therapy system 600. The label access process 700 can be initiated, for instance, when a user selects a device label area 802 on a menu screen 800 as shown in FIG. 8A and that is displayed on a user interface of a TNP apparatus, such as the TNP apparatus 310.

For convenience, the label access process 700 is described in the context of the negative pressure wound therapy system 500 and the negative pressure wound therapy system 600, but may instead be implemented in other systems described herein or by other systems not shown. Advantageously, the label access process 700 provides, in certain embodiments, an approach for a TNP apparatus to provide an up-to-date label without the TNP apparatus itself receiving or presenting updated label information.

At block 702, the label access process 700 can retrieve identification data from a memory device of a therapy device. For example, the TNP apparatus 310 can retrieve identification data from the memory device 312. The identification data can be data usable to access an up-to-date label for the TNP apparatus 310.

Figure 8B:
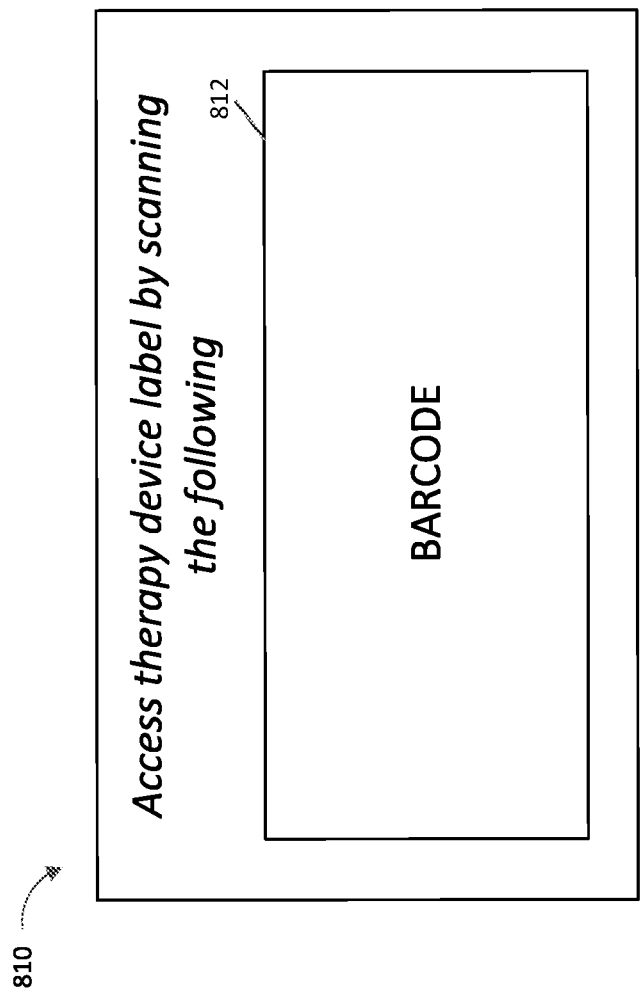

At block 704, the label access process 700 can output the identification data from the therapy device. For example, the user interface 314 can output the identification data by presenting the identification data as a two-dimensional barcode on a display of the user interface 314. The two-dimensional barcode may, for instance, be displayed in a barcode area 812 of a label access screen 810 as shown in FIG. 8B and that is displayed on a user interface of a TNP apparatus, such as the TNP apparatus 310. As another example, the user interface 314 can output the identification data by outputting the identification data wirelessly via the transceiver 316. In some implementations, the two-dimensional barcode or the identification data can include information such as an identifier associated with the TNP apparatus 310 or its type of apparatus, as well as an address or other directions for contacting the server 530 to request the up-to-date label.

At block 706, the label access process 700 can receive the identification data output by the therapy device with an electronic device. For example, the electronic device 510 can detect the two-dimensional barcode output by the user interface 314 with the image sensor 512. As another example, the electronic device 610 can detect the identification data output wirelessly by the transceiver 316 with the transceiver 612.

At block 708, the label access process 700 can generate a request from the identification data with the electronic device. For example, the control circuitry 516 can generate a request from the two-dimensional barcode to access to the up-to-date label for the TNP apparatus 310. As another example, the control circuitry 614 can generate a request from the wirelessly received identification data to access to the up-to-date label for the TNP apparatus 310.

At block 710, the label access process 700 can transmit the request with the electronic device. For example, the transceiver 518 can transmit the request via the network 520 to the server 530, or the transceiver 612 can transmit the request via the network 620 to the server 630. The request can be usable by the server 530 or the server 630 to retrieve and provide the up-to-date label for the TNP apparatus 310 to the electronic device 510 or the electronic device 610.

At block 712, the label access process 700 can receive the label associated with the request at the electronic device. For example, the electronic device 510 can receive the up-to-date label via the network from the server 530, or the electronic device 610 can receive the up-to-date label via the network from the server 630. The server 530 may have provided the up-to-date label to the electronic device 510 in response to the request from the electronic device 510, and the server 630 may have provided the up-to-date label to the electronic device 610 in response to the request from the electronic device 610.

The label can include information such as intended purpose of the therapy device, general therapy device warnings, related therapy device supplies and materials, therapy device components, conditions of therapy device use, user preparation information, regulatory numbers or codes for the therapy device or components thereof, name and place of business of manufacturer or distributor, unique therapy device identifiers, combinations of the same, or the like for the TNP apparatus 310. The label can include information in the form of symbols, pictures, alphanumeric characters, combinations of the same, or the like. Some or all of the information of the label can be encrypted prior to communication to the electronic device in view of the potentially safety critical nature of the information and to prevent, for instance, tampering with of the information by others. In some embodiments, the electronic device or the therapy device can hold one or more encryption keys to which message headers point for decryption.

At block 714, the label access process 700 can output the label with the electronic device for presentation to a user. For example, the electronic device 510 can present the label to a user on a display of the user interface 514, or the electronic device 610 can present the label to a user on a display of the user interface 616.

Figure 8C:

The label can, for instance, be displayed in a label area 821 of a label display screen 820 as shown in FIG. 8C and that is displayed on a user interface of an electronic device, such as the electronic device 510 or the electronic device 610. The label as displayed can include a therapy device name section 822 presenting a therapy device name, a therapy device provider name section 823 presenting a therapy device provider name, a provider contact information section 824 presenting provider contact information, a usage information section 825 presenting usage information, a regulatory or serial number section 826 presenting regulatory or serial numbers for the therapy device, a symbols section 827 presenting symbols denoting features of or related to the therapy device, and a machine-readable code section 828 presenting a barcode or the like. In some implementations, the label displayed in the label area 821 can include one or more other sections not shown, a subset of the sections shown in FIG. 8C, or multiple repeat or similar sections to those shown in FIG. 8C.

Figure 8D:
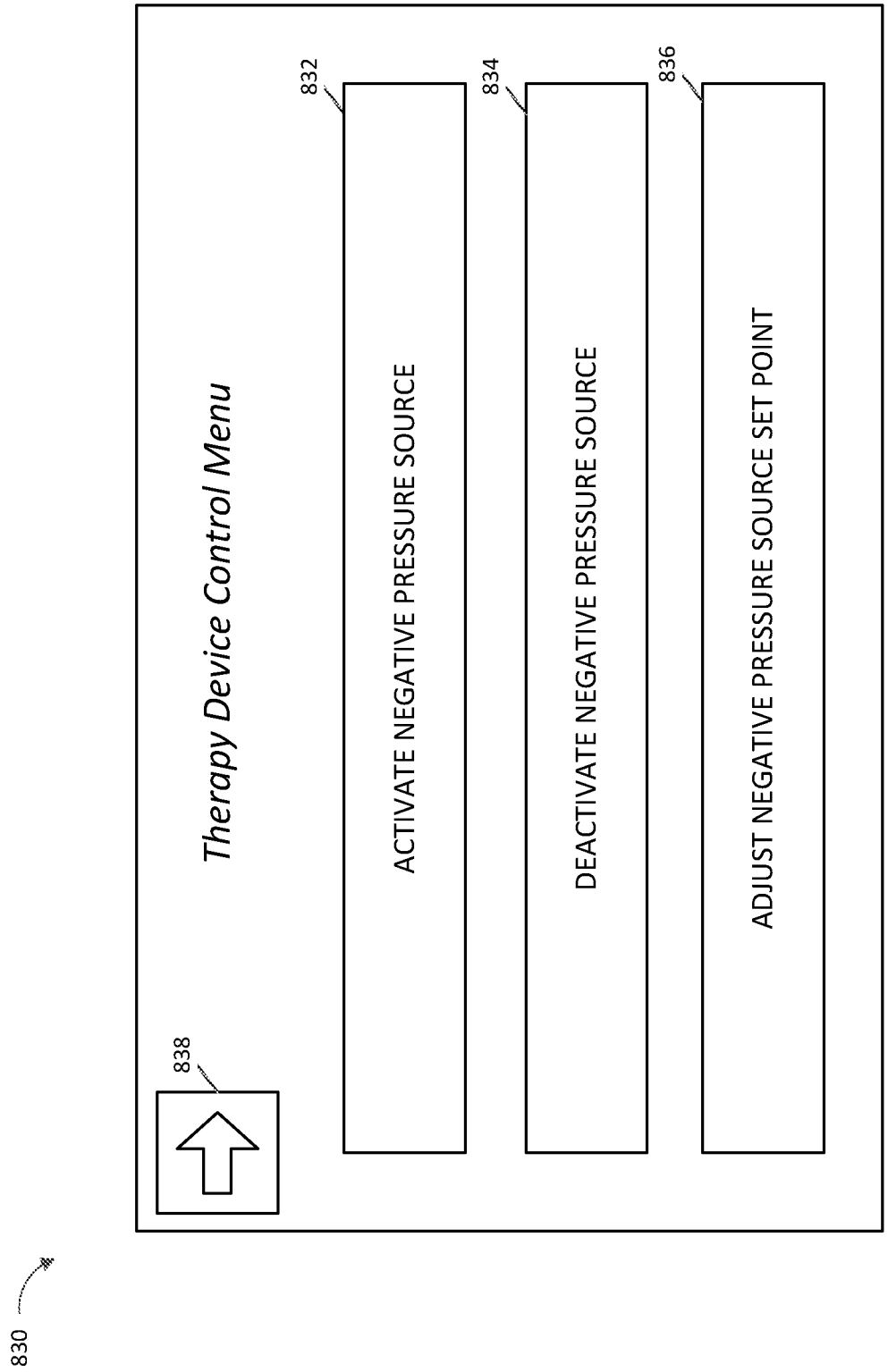

The label display screen 820 can also include a navigation control section 829 that, upon selection by a user, can cause navigate within an application running on an electronic device to another screen, such as a control screen 830 as shown in FIG. 8D. The control screen 830 can include an activation area 832 selectable by a user to activate a therapy device like the TNP apparatus 310, a deactivation area 834 selectable by the user to deactivate the therapy device, and an adjustment area 836 selectable by the user to adjust settings of the therapy device like a pressure set point. The control screen 830 can also include a navigation control section 838 that, upon selection by a user, can cause navigate within an application running on an electronic device to another screen, such as the label display screen 820.

At block 716, the label access process 700 can transmit a confirmation or verification with the electronic device. For example, the transceiver 518 can transmit the confirmation or verification via the network 520 to the server 530, or the transceiver 612 can transmit the confirmation or verification via the network 620 to the server 630. The confirmation or verification may include a code usable to confirm or verify that some or all of the information of the label has been presented by the display or that a correct or latest version of the label has been presented by the display. Moreover, the confirmation or verification can be indicative of a readiness of the TNP apparatus 310 (such as for use to perform therapy) and usable to monitor a therapy compliance for the TNP apparatus 310 (such as for device manufacturer, prescribing physician, or insurance provider). In one example, the confirmation or verification can include a combination of a device serial number and a software/data file update version, which may be logged in a database for regulatory or post market surveillance and maintenance use. The confirmation or verification can be encrypted or unique to a certain type of devices, which may provide increased cybersecurity protection. The confirmation or verification can be generated in some implementations at least from a label file. In some embodiments, one or more features of the TNP apparatus 310 or the electronic device 510 or the electronic device 610 may be disabled until the confirmation or verification has be generated or transmitted.

The label access process 700 can further include one or more other features in certain implementations. For example, a therapy device may not operate to provide therapy until the identification data is output by the therapy device. In another example, a therapy device may not operate to provide therapy until the identification data is output by the therapy device and the therapy device receives confirmation from an electronic device receiving the identification data that the identification data has been used to present an up-to-date label.

The electronic device or the therapy device can include one or more cybersecurity mechanisms to protect the integrity of their operations. For example, the electronic device or the therapy device may store data received from a remote server (such as, updated label or other information) on a memory which is physically separate from another memory used to control or operate therapy, so that malicious code may not be placed to adjust operations even if the communication with the remote server is compromised. In some instances, a control software of the electronic device or the therapy device can verify the data received from the remote server. When therapy settings are received remotely, the settings may be stored in a memory separate from the control software, such that the control software can check the memory for a setting against any pre-defined protocol or other limit. If the protocol or other limit is not met, the control software may not operate the electronic device or the therapy device.

Figure 9A:
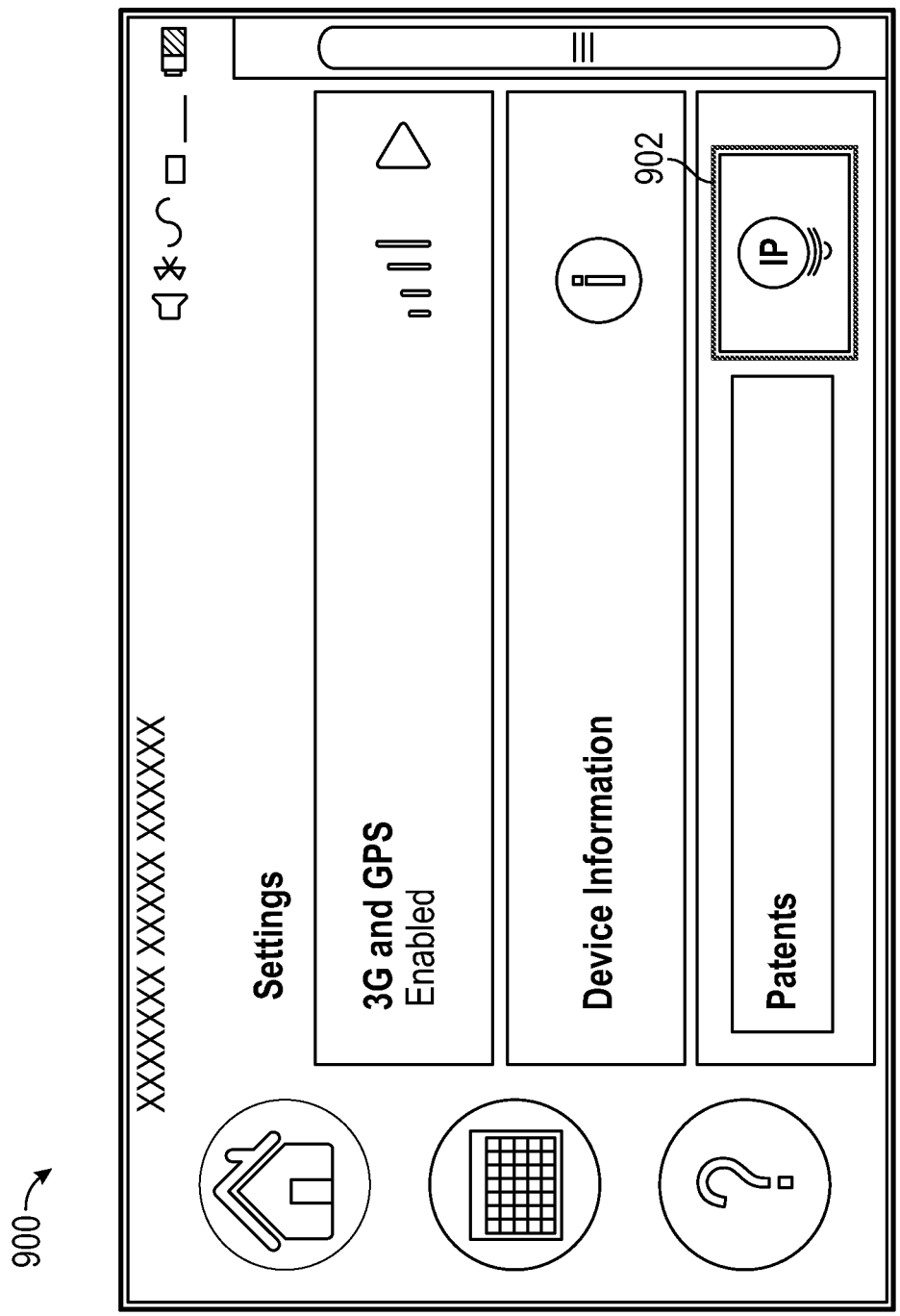
FIGS. 9A and 9B illustrate user interfaces for accessing intellectual property related information according to some embodiments.
Figure 9B:
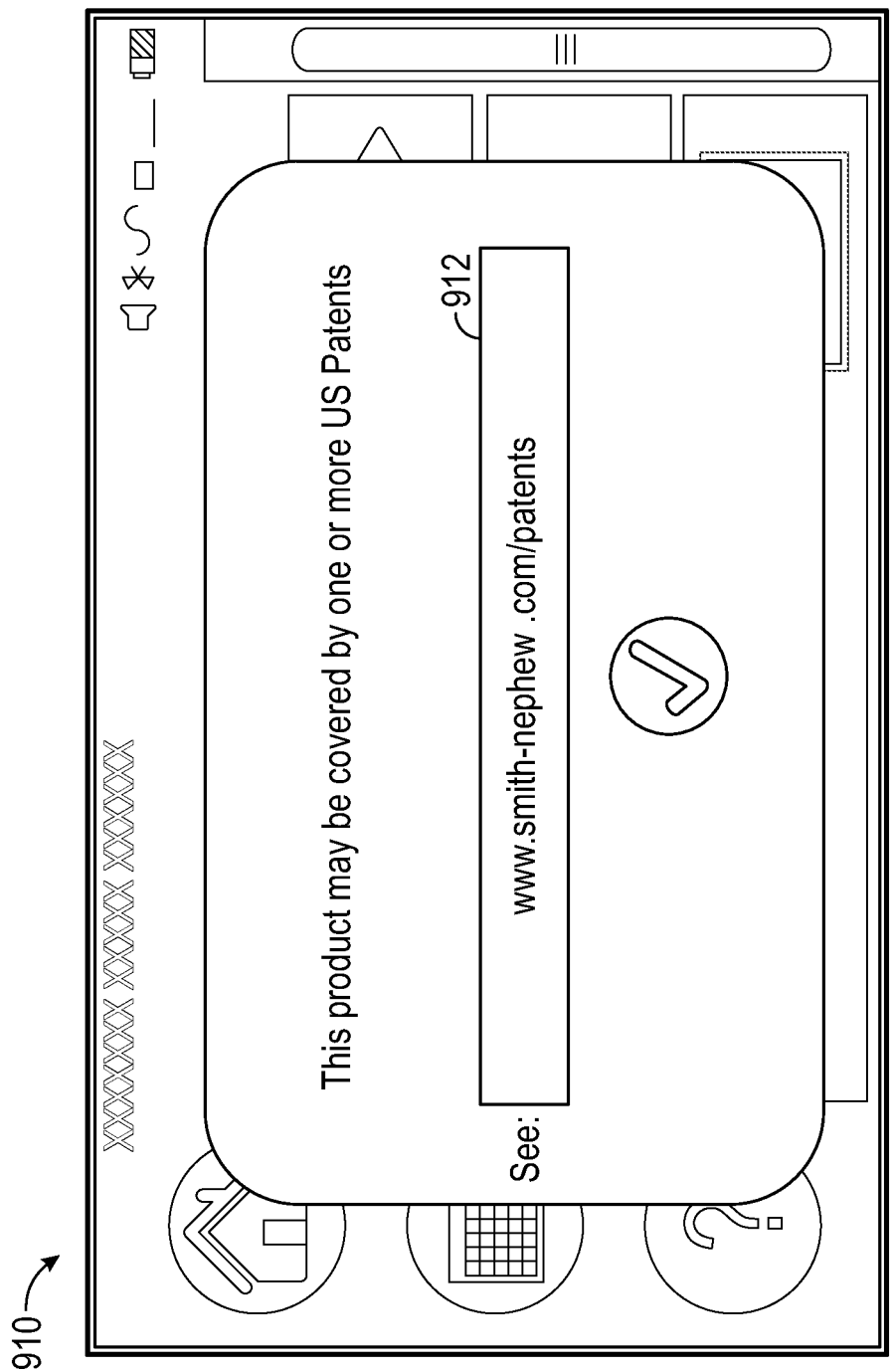

FIG. 9A illustrates a menu screen 900 that is displayable on user interface of a therapy device, such as the TNP apparatus 310. The menu screen 900 can include a patents area 902 selectable by a user to view patent or other intellectual property information related to the therapy device. Moreover, upon selection of the patents area 902, a patents screen 910 as shown in FIG. 9B can appear in place of the menu screen 900. The patents screen 910 can include a patents link area 912, which may be selectable by a user to load a link, such as a Uniform Resource Locator (URL), in an application like a browser.

Therapy Device Control Process

Figure 10:
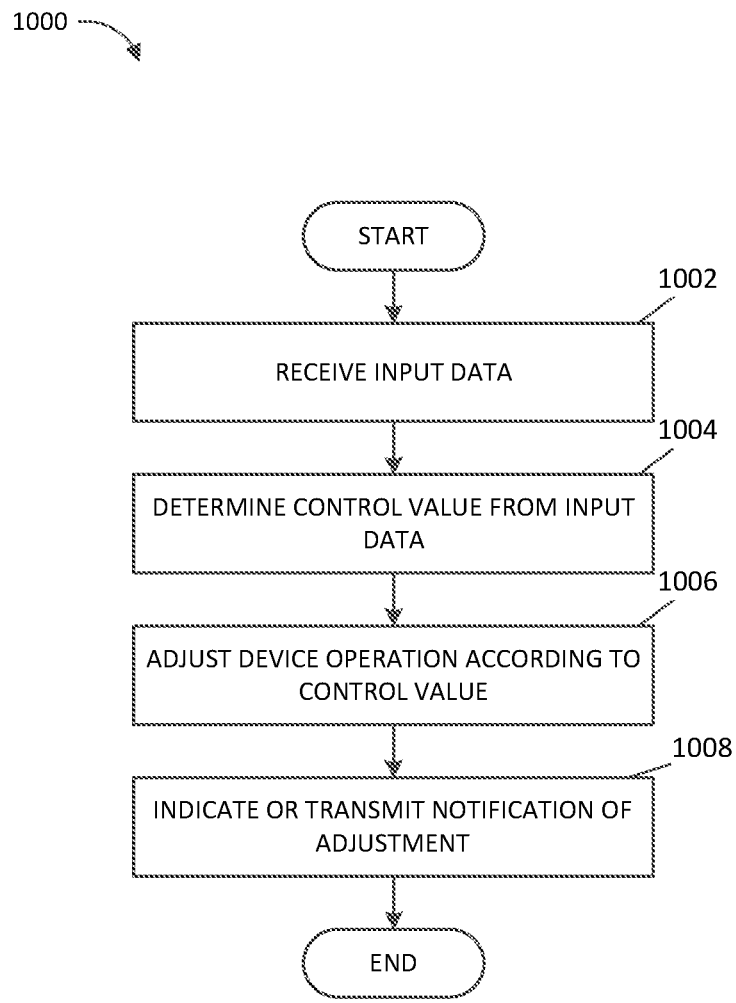
FIG. 10 illustrates a control process according to some embodiments.

FIG. 10 illustrates a control process 1000 performable by a device, such as the TNP apparatus 150 of FIG. 1, the pump assembly 230 of FIG. 2A-C, the TNP apparatus 310 of FIG. 3A, or other TNP apparatuses like those described in U.S. Patent Publication Nos. 2016/0136339 and 2016/0184496 that were previously incorporated herein by reference in their entireties. For convenience, the control process 1000 is described in the context of the TNP apparatus 310 of FIG. 3A, but may instead be implemented in other systems described herein or by other systems not shown.

The control process 1000 can advantageously enable the TNP apparatus 310 to perform more efficiently, effectively, or safely than other TNP apparatuses, such as by functioning dynamically and intelligently to prevent degradation in performance of therapy, prevent device misuse, help ensure that therapy is completed, preserve performance of the negative pressure source 313, or ensure that the negative pressure source 313 adapts to a changing external environment.

At block 1002, the controller 311 can receive input data. The input data can include, for instance, device operating information, information about the environment around the TNP apparatus 310, information about current conditions of a patient using the TNP apparatus 310, or prescribed therapy and information. The input data can be collected using a sensor (such as the pressure sensor 316 or the one or more other sensors 318), a user input (such as via the user interface 314), or a received control input (such as via a communication received by the transceiver 317 from another device via the network 330), among other possible sources like those described herein or the like.

At block 1004, the controller 311 can determine a control value from the input data. The control value can be, for example, a control parameter usable to adjust an operation controlled by the controller 311.

At block 1006, the controller 311 can adjust a device operation according to the control value. The controller 311 can, for instance, change a processing by the TNP apparatus 310 (such as an alarming, an applied pressure control algorithm, when or how to report data, when or how to collect inputs used to alter processing, device power usage, or noise suppression in signals) according to the control value.

At block 1008, the controller 311 can indicate adjustment of the device operation or transmit a notification of adjustment of the device operation. The controller 311 can, for example, set a flag in a memory device indicating successful or unsuccessful adjustment or transmit a confirmation or verification indicative of the successful or unsuccessful adjustment to another device, such as via a communications network.

Remote Programming and Local Confirmation Example

The control process 1000 can be the process by which remote programming is manually validated locally at the TNP apparatus 310. The data processing system 320 can provide via the network 330 an instruction message to the TNP apparatus 310 to function according to certain instructions, such as a prescribed treatment for a patient assigned to use the TNP apparatus 310. To ensure, however, that the function provided by the certain instructions are appropriate and safe for the patient, a caregiver can use the user interface 314 to review and confirm the function and provide authentication that activates the function. In the absence of the local authentication by an appropriate caregiver, the TNP apparatus 310 can receive the certain instructions but may not function according to the certain instructions. In one implementation, the caregiver may have caused the data processing system 320 to provide the certain instructions, and the local authentication can thus provide a check that the certain instructions were correctly received or to be implemented by the TNP apparatus 310. Once the local authentication has been received, the TNP apparatus 310 can further transmit a confirmation or verification of receipt of the local authentication, such as to another device via a communications network. For instance, the confirmation or verification can be indicative of a readiness of the TNP apparatus 310 (such as for use to perform therapy) and usable to monitor a therapy compliance for the TNP apparatus 310. In one implementation, the confirmation or verification can include a combination of a device serial number and a software/data file update version as described herein that may be encrypted or unique to a certain type of devices. Additionally or alternatively, a failure to successfully perform the local authentication can cause the TNP apparatus 310 to transmit failure notification, such as to another device via a communications network.

The authentication described in the preceding paragraph can be additionally or alternatively implemented using one or more approaches. For example, the authentication can be performed using a validation code entered via the user interface 314, via a radio-frequency identification (RFID) tag, or a handheld device of the caregiver (such as a smart phone). Moreover, the authentication described in the preceding paragraph can be desirable, in certain instances, for use in a home healthcare setting where a clinician in a patient's home may review and confirm the certain instructions.

Two-Way Control of Negative Pressure Source Example

The control process 1000 can be the process by which the TNP apparatus 310 is remotely set into different modes, such as a home-use mode (for instance, where the pressure settings for using the TNP apparatus 310 may not be changed) or a hospital mode (for instance, where the pressure settings for using the TNP apparatus 310 may be changed). The data processing system 320 can provide via the network 330 an instruction to the TNP apparatus 310. The TNP apparatus 310 can, in turn, adjust its mode according to the instruction. In some implementations, the change in mode by the TNP apparatus 310 can trigger an alarm of the user interface 314 or an alarm at the data processing system 320 via a communication from the TNP apparatus 310 through the network 330.

Alarm Setting Example

The control process 1000 can be the process by which the TNP apparatus 310 changes its alarming (such as by (i) raising or lowering an alarm sensitivity like an alarm threshold for audibly or visibly alarming depending on a particular mode or (ii) adjust help screen shown to the patient depending on a particular mode) according to whether a patient using the TNP apparatus 310 may be at a particular location, moving around, or situated in a certain environment.

For instance, the TNP apparatus 310 can have an ambulatory mode or a stationary mode. The mode of the TNP apparatus 310 can be set according to a user input to the user interface 314 or via a sensor input using a sensor like a motion sensor (for example, an accelerometer or gyroscope) or an orientation detector. The TNP apparatus 310 can activate an audible or visible alarm of user interface 314 or display a particular help screen depending both device operating parameters and the mode of the device. In another instance, the TNP apparatus 310 can suppress or alternatively present one or more alarms presented by the TNP apparatus 310 when the TNP apparatus 310 determines that its location is within an area (such as, using GPS data or Wi-Fi or location communication triangulation data collected by the TNP apparatus 310) where a caregiver would be expected to be present, such as at a hospital. In yet another instance, the TNP apparatus 310 can suppress or alternatively present one or more alarms presented by the TNP apparatus 310 when the TNP apparatus 310 determines that a local time where the TNP apparatus 310 is positioned (which may be automatically determined by the TNP apparatus 130 with GPS data or Wi-Fi or location communication triangulation data collected by the TNP apparatus 310) falls within a suppression period (such as, during late night hours when a patient would be expected to be sleeping) of an alarm suppression schedule, which may be programmed at manufacture or set or adjusted by user input to the user interface 314.

As another example, the TNP apparatus 310 can determine a transportation environment (for instance, transportation in an automobile, train, or airplane) in which the TNP apparatus 310 is positioned. The transportation environment can be set according to a user input to the user interface 314 or via a sensor output from the one or more other sensors 318 (for instance, a motion sensor or an audio sensor for detect frequencies of vibration or noise). In one example, when the one or more other sensors 318 includes a motion sensor, the output of the motion sensor can be used to detect a movement pattern indicative of a certain transportation or the audio sensor detects certain noise or vibration, such as in a range of 1 Hz to 1 KHz, over a threshold level, and the TNP apparatus 310 can, for instance, adjust certain settings like the alarm sensitivity (such as, by decreasing the sensitivity) or sound volume (such as, by increasing the volume). In environments where low noise or vibration levels are detected, the sensitivity of alarms may, for instance, be increased or sound volume may be decreased.

The alarm sensitivity adjustment described in the preceding paragraph can, in some implementations, be used to adjust a threshold for triggering an alarm to indicate a blockage. As described in U.S. Patent Publication Application No. 2016/0184496, the entire disclosure of which is hereby incorporated by reference in its entirety, peak-to-peak measurements of pressure can be used to detect a blockage. In one example, a trigger for the blockage alarm in one condition can be counting the number of peak-to-peak measurements that exceed a threshold level in a period of time. When the sensitivity of alarms is reduced, the peak-to-peak threshold can, for example, be increased for the period of time. As a result, the alarming for a therapy device may be a less sensitive when a patient is walking than when a patient is riding in a moving vehicle.

Noise Rejection or Suppression Example

The control process 1000 can be the process by which the TNP apparatus 310 adjusts its functioning to reject or suppress noise so that the TNP apparatus 310 may continue to accurately function. The TNP apparatus 310 can, for example, stop operating when the TNP apparatus 310 detects an environment of high interference (such as, a high temperature, humidity, position, or acceleration) or operate more conservatively and with lower confidence that instructed operations are being performed. The TNP apparatus 310 can, moreover, communicate data to the data processing system 320 via the network 330 when the TNP apparatus 310 detects that an interference level around the TNP apparatus 310 or in the network 330 is below an interference threshold.

Power Management Example

The control process 1000 can be the process by which the TNP apparatus 310 shuts off one or more components or services provided by the TNP apparatus 310 depending on a remaining amount of energy or operating temperature of the power source 315. This can desirably, in certain embodiments, enable the TNP apparatus 310 to preserve power for operating the negative pressure source 313.

Location Services Selection Example

The control process 1000 can be the process by which the TNP apparatus 310 selects from one or more sources of location information. For instance, in response to the TNP apparatus 310 determining that the patient is moving (such as using a motion sensor or an orientation sensor), the TNP apparatus 310 can attempt to use Wi-Fi or location communication triangulation data to determine the location of the TNP apparatus 310 rather than GPS data. Moreover, in response to the TNP apparatus 310 determining that the patient is stationary (such as using the motion sensor or the orientation sensor), the TNP apparatus 310 can attempt to use GPS data to determine the location of the TNP apparatus 310 rather than Wi-Fi or location communication triangulation data.

Control Using Analog Rather Than Digital Example

The control process 1000 can be the process by which the TNP apparatus 310 selects to use analog data or digital data to control the negative pressure source 313. For instance, when operating in certain environments like high noise environments (such as, when the therapy device may be exposed to significant amounts of motion, electromagnetic radiation, or heat), an analog pressure sensor may provide a more accurate pressure reading than a digital pressure sensor for use in the controller 311 controlling the negative pressure source 313.

User Interface Menu Configuration Example

The control process 1000 can be the process by which the TNP apparatus 310 configures behavior of menus of the user interface 314 according to environmental conditions detected by the TNP apparatus 310.

The TNP apparatus 310 can, for example, automatically display a particular help screen on the user interface 314 responsive to detecting a certain detected environmental condition (for instance, using a motion sensor, an orientation sensor, or other sensor) associated with the particular help screen. The particular help screen may present information usable by a user of the TNP apparatus 310 to diagnose and resolve the detected environmental condition. The TNP apparatus 310 can thus timely present the particular help screen on the user interface 314 in anticipation of the user seeking out the particular help screen to address the environmental condition.

In yet another example, the TNP apparatus 310 can simplify one or more user interfaces displayed to a user (for instance, by reducing an amount of presented data, reducing a number of available inputs, or changing a presentation scheme such as to have different colors, interface element sizes, or presented durations of interface elements) when the TNP apparatus 310 detects an environmental condition associated with a less friendly environment for operating the TNP apparatus 310, such as when the TNP apparatus 310 is determined to be moving (such as using a motion sensor or an orientation sensor) or a detected ambient temperature is below a first temperature threshold (for instance, 30° F., 40° F., or 50° F.) or is above a second temperature threshold (for instance, 100° F., 110° F., or 120° F.).

In yet another example, the TNP apparatus 310 can vary an amount of user interface interactivity that is requested from a user depending on a determined patient health or activity level (such as, may be determined from a user input indicating patient health or activity level or inferred from one or more past user inputs or detected conditions around the TNP apparatus 310 or about the user. For instance, the TNP apparatus can simplify one or more user interfaces displayed to a user (such as, by reducing an amount of presented data, reducing a number of available inputs, or changing a presentation scheme such as to have different colors, interface element sizes, or presented durations of interface elements) when the TNP apparatus 310 detects less than a threshold amount of movement, or when the TNP apparatus 310 receives other information like vital signs that indicate the patient may not healthy enough to provide much user input.

Flow-Based Pressure Control Example

The control process 1000 can be the process by which the TNP apparatus 310 automatically increases pressure provided by the negative pressure source 313 responsive to determining that a flow of liquid has increased from a wound to which the negative pressure is provided. This increase can desirably, in certain embodiments, help prevent a decrease in an effectiveness of therapy provided by the TNP apparatus 310 as the flow of liquid from the wound increases.

Time Configuration Example

The control process 1000 can be the process by which the TNP apparatus 310 automatically determines local time, date, or daylight savings data, and accordingly adjusts its settings. The TNP apparatus 310 may include a communications module, such as a 3G module, which enables the TNP apparatus 310 to obtain the local time, date, and daylight savings time data from a computer network like a cellular network. In response to the TNP apparatus 310 determining local time, date or daylight savings data, the TNP apparatus 310 can adjust its display or use of time, date, or any other time or date associated data for the TNP apparatus 310. As a result, a user of the TNP apparatus 310 may or may not need to manually provide time information, so a possibility of use error is reduced. Further, the TNP apparatus 310 may or may not need to have an internal clock which keeps running from user start-up or manufacture of the TNP apparatus 310. In some implementations, the TNP apparatus 310 can use GPS data to obtain a location of the TNP apparatus 310 to automatically determine a local time as described herein.

Altitude Configuration Example

The control process 1000 can be the process by which the TNP apparatus 310 determines an altitude of where the TNP apparatus 310 is located and adjusts one or more therapy parameters according to the determined altitude. For instance, the TNP apparatus 310 may include a sensor, such as an altimeter, atmospheric pressure sensor, accelerometer, or GPS sensor, usable to detect altitude at which the TNP apparatus 310 is positioned. In response to determining that the detected altitude is within one or more altitude ranges or above a threshold (for example, above 10,000 ft. altitude), the TNP apparatus 310 can adjust one or more therapy parameters, such as a pressure setting level, pressure variation pattern, mode of operation of pressure source, alarm threshold, alarm sensitivity, sensor sensitivity, or the like.

Hyperbaric Chamber Example

The control process 1000 can be the process by which the TNP apparatus 310 detects the presence of a hyperbaric chamber nearby and adjusts an operation of the TNP apparatus 310 when the hyperbaric chamber is detected. For instance, the TNP apparatus 310 can include one or more sensors to detect an elevated ambient pressure level or an elevated ambient oxygen level, which may be caused by the use of a hyperbaric chamber. In response to the detection of the hyperbaric chamber, the TNP apparatus 310 can adjust its operation (such as, by powering off the TNP apparatus 310, diminishing an operating power level, or deactivating certain functionality) to reduce a risk of fire.

Motion Detection Example

The control process 1000 can be the process by which the TNP apparatus 310 detects a movement or orientation of the TNP apparatus 310 and adjusts its operation according to the movement or orientation. In some instances, the TNP apparatus 310 may determine an acceleration or orientation of the TNP apparatus 310 using the one or more other sensors 318 where the one or more other sensors 318 includes one or more motion sensors. The TNP apparatus 310 further select an operation mode based at least on the detected acceleration or orientation, and adjust an operation of the controller 311 according to the operation mode.

The control process 1000 may be useful for adjusting the operation of the TNP apparatus 310 in various situations. For example, the TNP apparatus 310 may experience an error condition that may trigger an alarm where the error condition may be caused by an inversion of the TNP apparatus 310 that saturates a filter positioned between the canister and a negative pressure source of the TNP apparatus 310 with fluid stored in the canister. In another instance, when the TNP apparatus 310 may detect an aircraft environment, the TNP apparatus 310 can automatically turn off certain wireless data communication functionality (for instance, 3G-GPS communications) so that a user may not have to manually turn off the functionality as may be required by regulatory authorities. The TNP apparatus 310 can additionally or alternatively change the sound volume of alarm according to the operation mode or change a threshold value for a blockage alarm at least based on an acceleration or orientation of the TNP apparatus 310.

Figure 11:
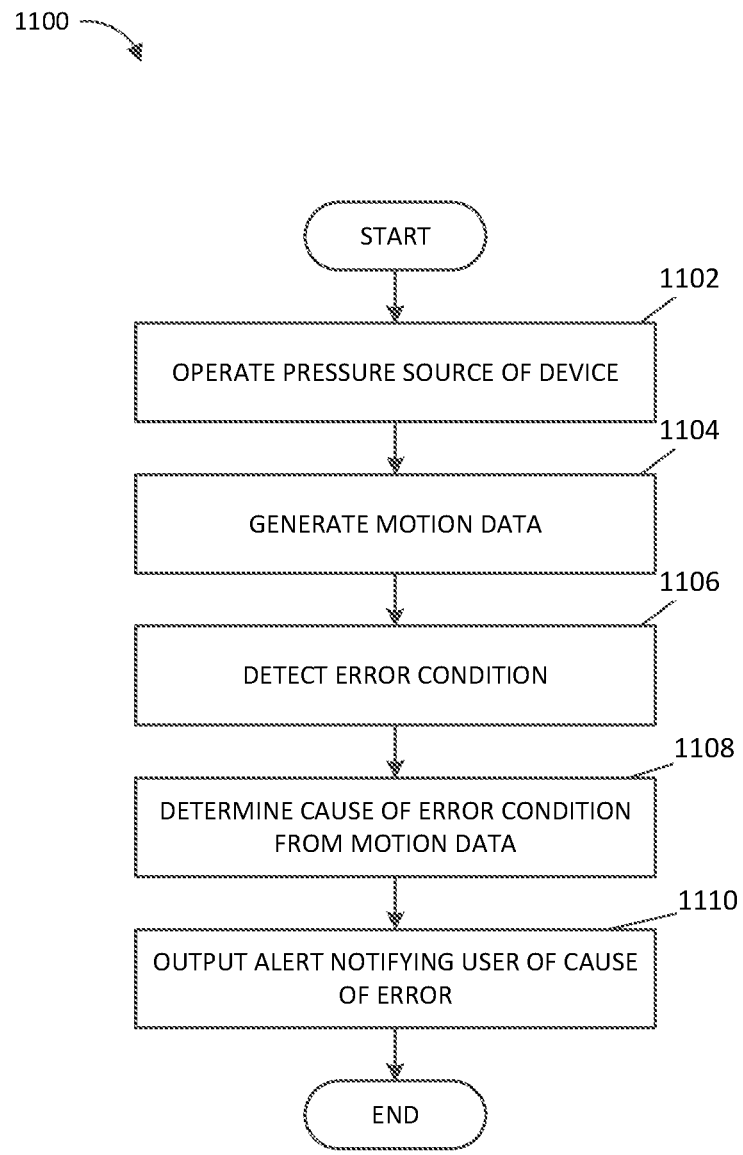
FIG. 11 illustrates a monitoring process according to some embodiments.

FIG. 11 illustrates a monitoring process 1100 according to some embodiments. The monitoring process 1100 can be performed by a therapy system, such as the negative pressure wound therapy system 300A. The therapy system can include a TNP apparatus having a motion sensor, such as the TNP apparatus 310 having the one or more other sensors 318 including the one or more motion sensors. The monitoring process 1100 can be initiated, for instance, when a user selects a motion detecting on/off area (not shown) on a user interface of the TNP apparatus, such as the menu screen 800 as shown in FIG. 8A. In some instances, the monitoring process 1100 can be initiated automatically when the TNP apparatus is active or powered.

For convenience, the monitoring process 1100 is described in the context of the negative pressure wound therapy system 300A but may instead be implemented in other systems described herein or by other systems not shown. Advantageously, the monitoring process 1100 provides, in certain embodiments, an approach for a TNP apparatus to determine a cause of an error condition and provide information about the cause of the error condition.

At block 1102, the monitoring process 1100 can operate a pressure source of a therapy device. For example, the TNP apparatus 310 can operate the negative pressure source 313.

At block 1104, the monitoring process 1100 can generate motion data indicative of a motion of the therapy device using a motion sensor. For example, the TNP apparatus 310 can generate motion data indicative of a motion of a housing of the TNP apparatus 310 using the one or more sensors 318. The motion data can include acceleration, direction of acceleration, change in acceleration, or an angle formed with the direction of gravity, among other information. Various motion data and determination of a motion of the device from motion data are further described herein. The motion data can be stored or recorded in a log in the memory device 312 by the TNP apparatus 310 to permit the motion data to be accessed later.

At block 1106, the monitoring process 1100 can detect an error condition associated with providing of negative pressure to the wound with the pressure source. For example, the error condition can be a blockage in the fluid flow path or a low pressure level at the wound. The TNP apparatus 310 may determine the blockage from a flow in the fluid path or a level of activity of the negative pressure source 313 from pressure values determined using the pressure sensor 316. The error condition may or may not trigger an alarm by the TNP apparatus 310. Examples of error conditions, including leaks or blockages, are described in U.S. Patent Publication Nos. 2015/0025482, 2016/0184496, 2017/0216501, which are incorporated by reference in their entirety. The TNP apparatus 310 can additionally create or add to an entry in a log indicating the occurrence of the error condition. The log may be stored in the memory device 312. In some instances, the TNP apparatus 310 can determine a frequency of the error condition from the log. The TNP apparatus 310 can operate the negative pressure source 313 differently than prior to the detection of the error condition. For instance, the TNP apparatus 310 can deactivate the negative pressure source 313 or change a set point or mode of operation for the negative pressure source 313, among other possibilities.

At block 1108, the monitoring process 1100 can determine a cause of the error condition from the motion data. The cause of the error condition may be determined from the motion data generated prior to, at the time of, or subsequent to the occurrence of the error condition. The TNP apparatus 310 can, for example, analyze the motion data for one or more features indicative of particular causes of error conditions or compare the motion data to model motion data indicative of particular causes of error conditions. If the TNP apparatus 310 determines that the motion data, such as over a duration of time (for example, 0.2, 0.5, 1, 1.5, 2, 3, 5, 10, 20, or 30 seconds), satisfies a threshold associated with a feature indicative of a particular cause or has a threshold degree of similarity to the model motion data associated with a certain cause, the TNP apparatus 310 can determine that the particular or certain cause is the cause of the error condition.

In one example, the TNP apparatus 310 may include a canister, such as the canister 220 of FIGS. 2A-C, which is supported by a housing of the TNP apparatus 310, such that the canister can collect fluid aspirated from the wound. When the housing of the TNP apparatus 310 is mishandled, such as rotated or vibrated inappropriately, it may cause a filter between the canister and a pump assembly of the apparatus to become saturated with the fluid within the canister. The monitoring process 1100 can detect a threshold magnitude of the rotation or vibration from the motion data and determine that a blockage detected by the TNP apparatus 310 may likely be caused by the canister becoming saturated with the fluid due to the the rotation or vibration. As another example, exertion of the unusual shock to the TNP apparatus 310 can be detected from the motion data, and the shock can be determined to be the cause of a blockage or leak. Other examples of improper handling of the TNP apparatus 310 are further described herein.

At block 1110, the monitoring process 1100 can output an alert for presentation to a user notifying the user of the cause of the error condition. The alert may be presented together with or separate from an alarm associated with the error condition. The alert can identify an improper rotation, vibration, shock, or other motion of the housing of the TNP apparatus 310 or may identify how a motion of the housing resulted in an error condition associated with one or more components of the TNP apparatus 310. The alert can be visually or audibly presented to the user. In one example, the TNP apparatus 310 can output a warning or an alarm, such as for presentation via the user interface 314, notifying that the filter of the canister may be saturated due to a rotation or vibration of the housing of the TNP apparatus 310.

The TNP apparatus 310 can additionally or alternatively output a user instruction to the user, such as for presentation via the user interface 314, indicating how to remedy the error condition. For example, the TNP apparatus 310 may output a user instruction to replace the filter of the canister responsive to the detection of the rotation or vibration that likely caused the filter of the canister to become saturated with the fluid. In some embodiments, the TNP apparatus 310 may output a user instruction to the user indicating how to prevent future occurrences of the error condition, such as how not to repeat the cause of the error condition. For example, the TNP apparatus 310 can indicate not to rotate or vibrate the housing of the TNP apparatus 310 as detected from the motion data, such as by outputting one or more images or videos for presentation to the user that illustrate proper or improper device handling corresponding to the cause of the error condition.

In addition to or instead of outputting an alert or a user instruction, the monitoring process 1100 can operate differently responsive to determining the cause of the error condition, such as by operating the negative pressure source 313 differently than prior to determining the cause of the error condition. For instance, the TNP apparatus 310 can deactivate the negative pressure source 313 or change a set point or mode of operation for the negative pressure source 313, among other possibilities.

Figure 12:
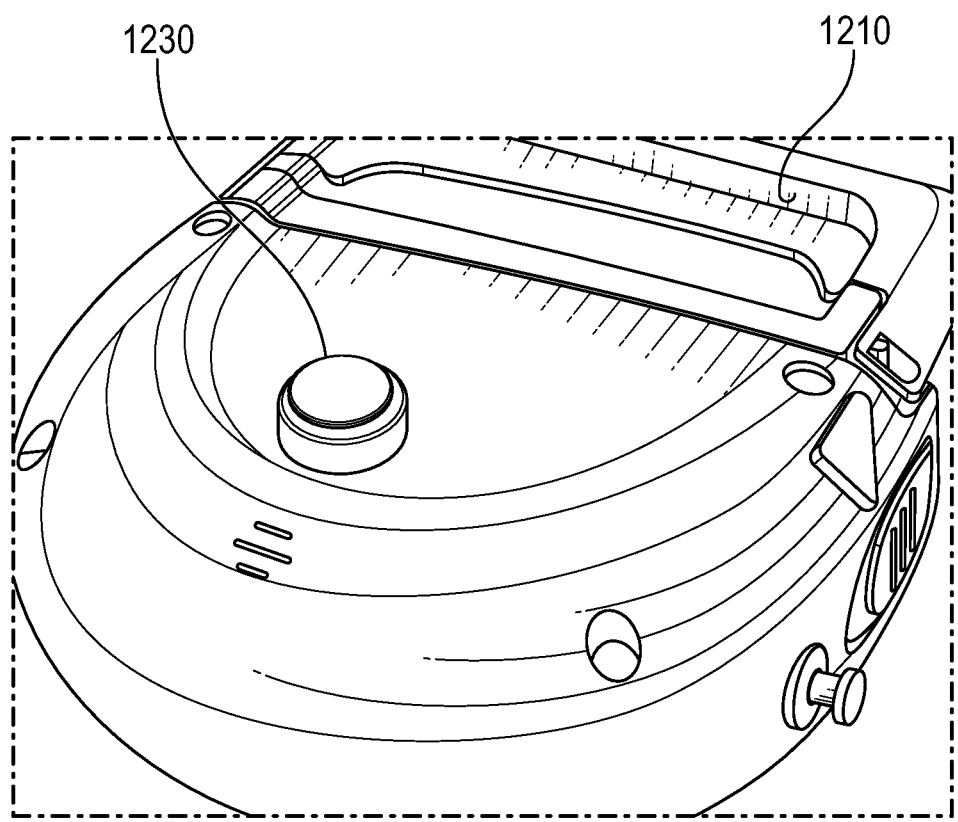
FIG. 12 illustrates a TNP apparatus according to some embodiments.

FIG. 12 illustrates a TNP apparatus 1210, which can be similar to the pump assembly 230 and the canister 220 of FIG. 2A and further include a motion sensor 1230, which can be similar to the one or more other sensors 318 of FIG. 3A. The motion sensor 1230 can be attached to a housing of the TNP apparatus 1210. The motion sensor 1230 can detect a movement or an orientation of the TNP apparatus 1210.

FIGS. 13A-13J illustrate plots of measurements from a motion sensor attached to a TNP apparatus, such as the motion sensor 1230 of FIG. 12 or another motion sensor described herein. In FIGS. 13A-13J, "Steps" can be determined and output by the motion sensor 1230. "Pitch" may indicate the orientation of the TNP apparatus, and can be determined by the angle formed by the motion sensor 1230 with respect to the direction of gravity. "RMS" can be determined by a root-mean-square of the accelerations measured by the motion sensor 1230 in x, y, and z directions. "Shock" can be determined and output by the motion sensor 1230 and indicative of large changes in acceleration.

Figure 13A:
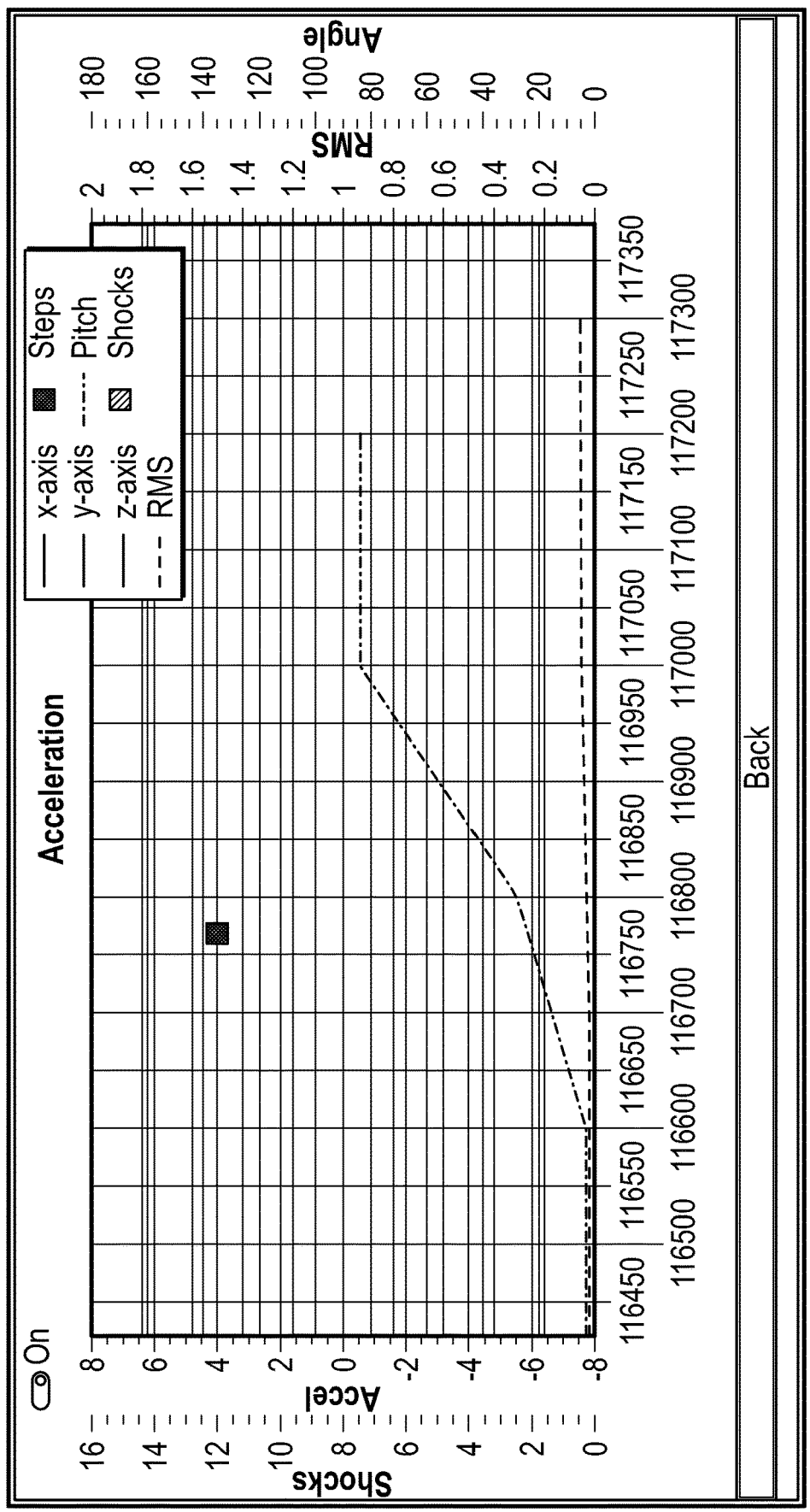
FIGS. 13A-13J illustrate plots of motion data over time collected when the TNP apparatus of FIG. 12 was moved.
Figure 13B:
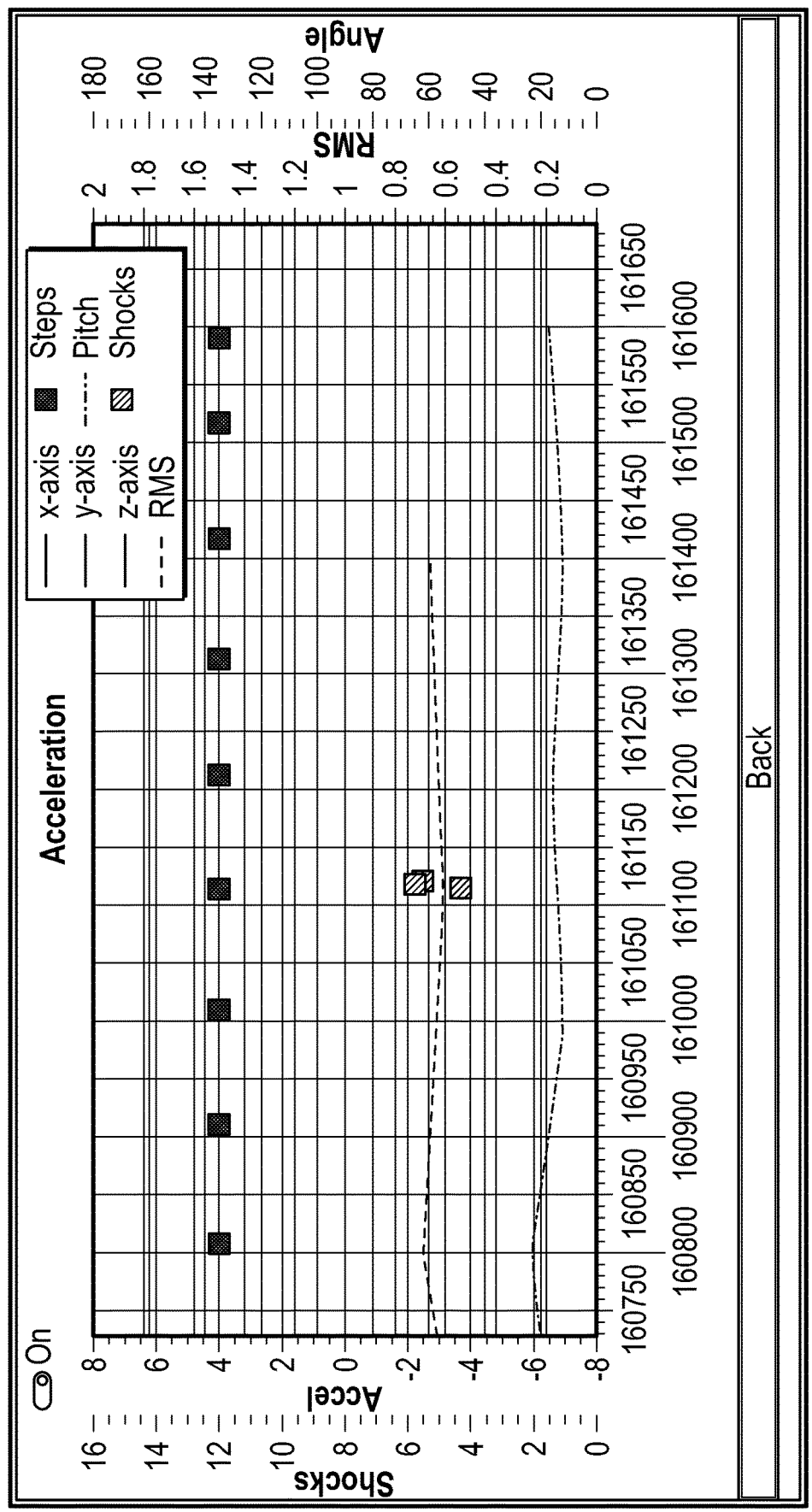
Figure 13C:
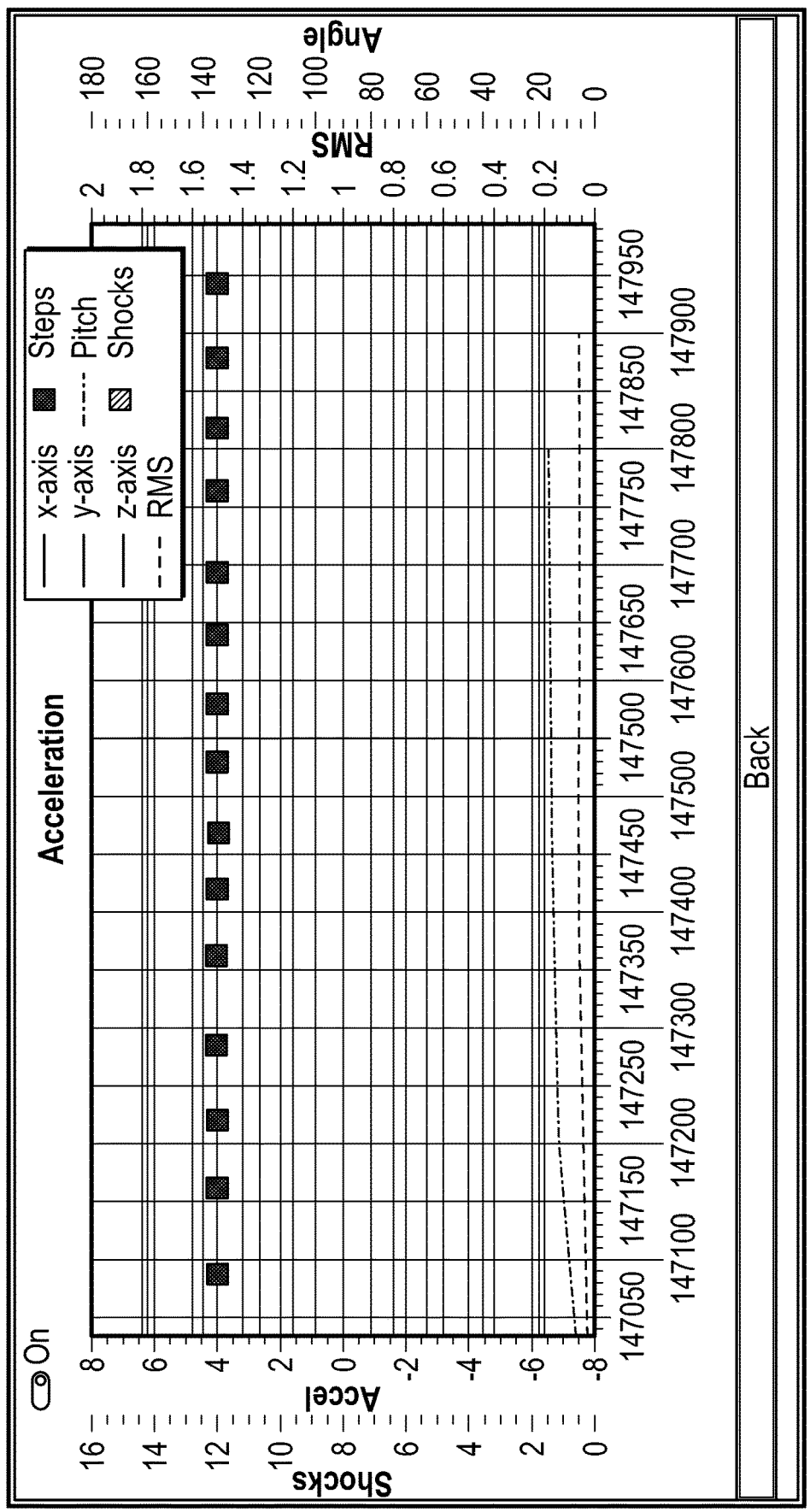
Figure 13D:
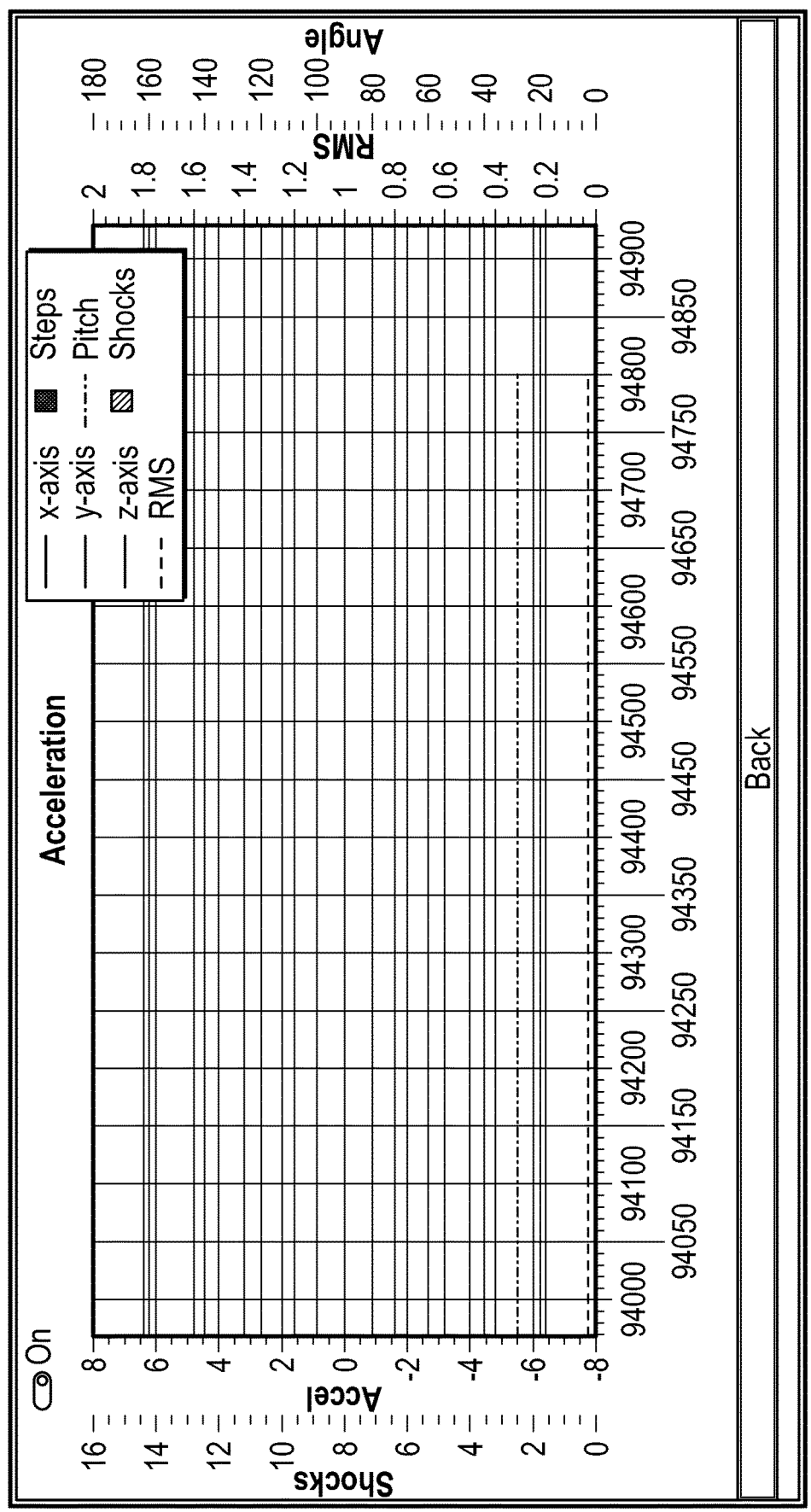
Figure 13E:
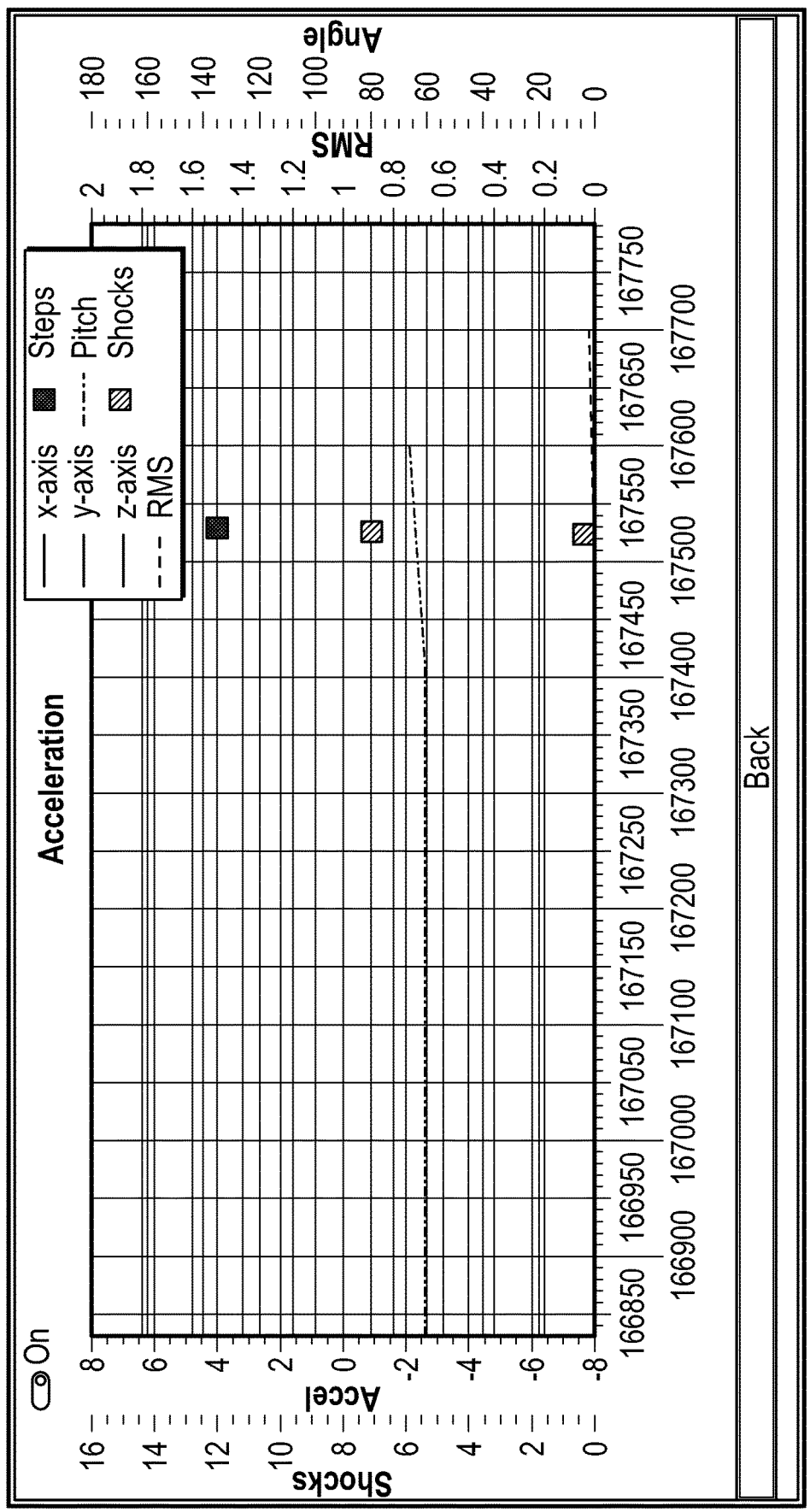
Figure 13F:
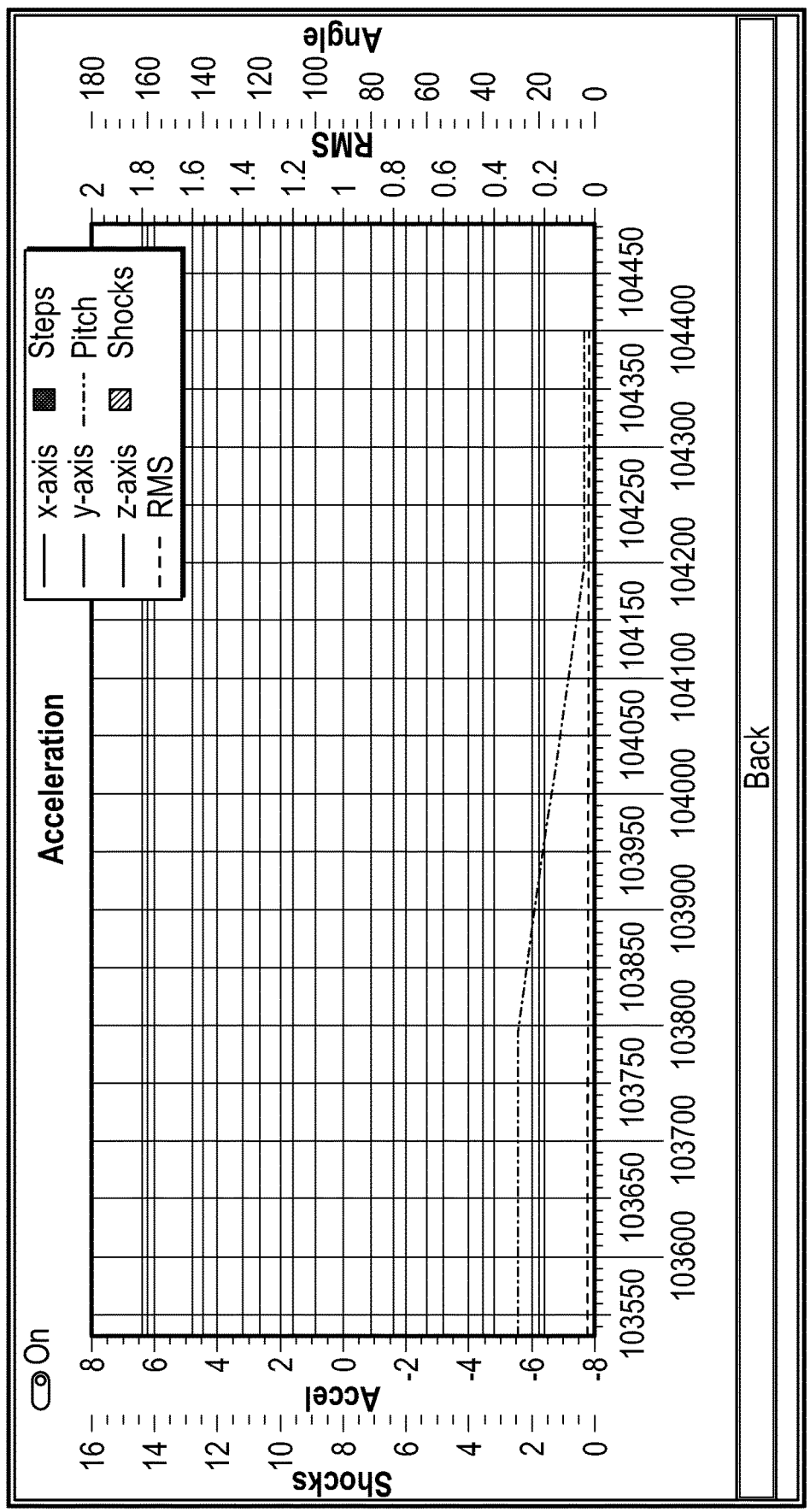
Figure 13G:
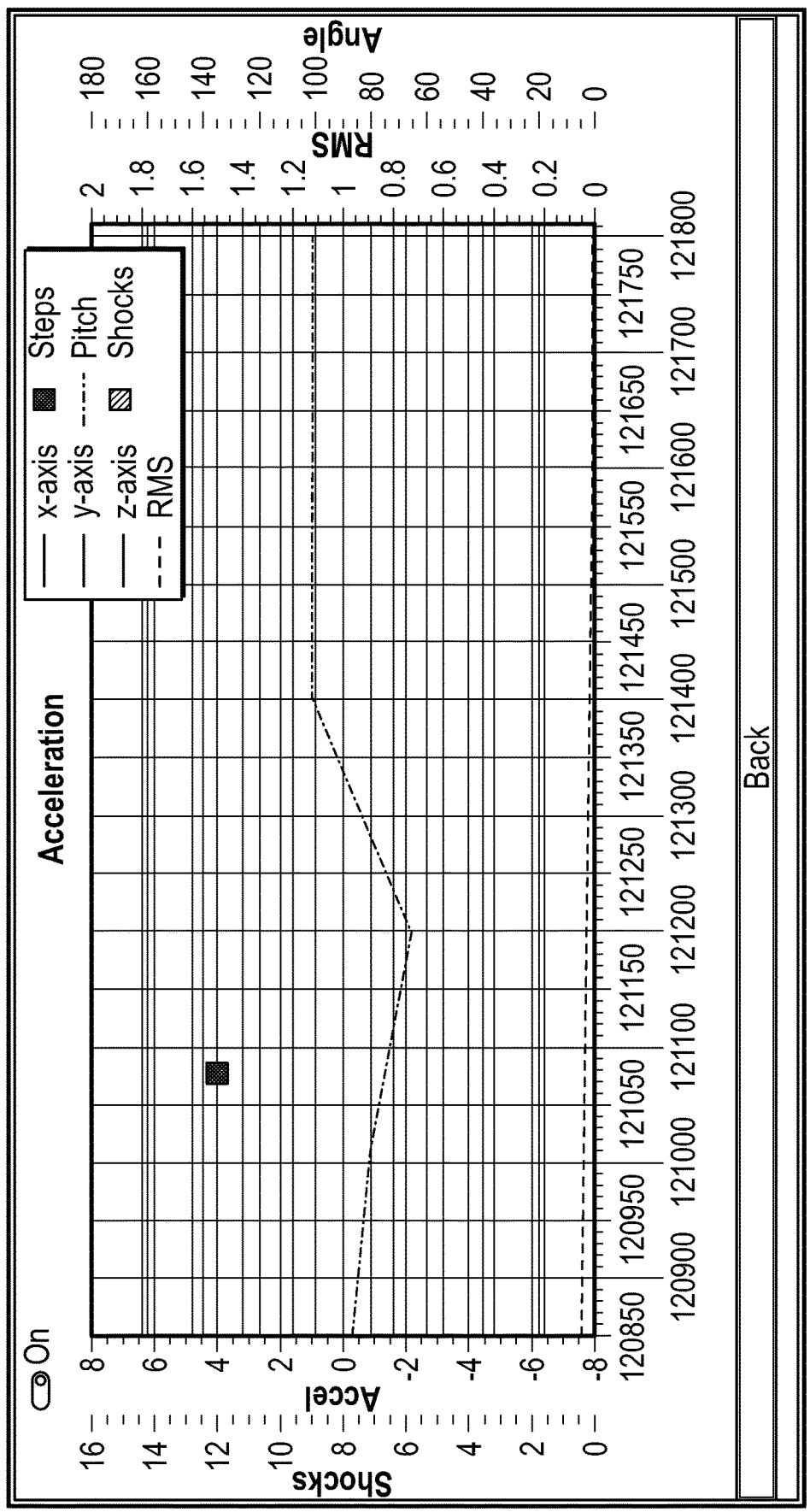
Figure 13H:
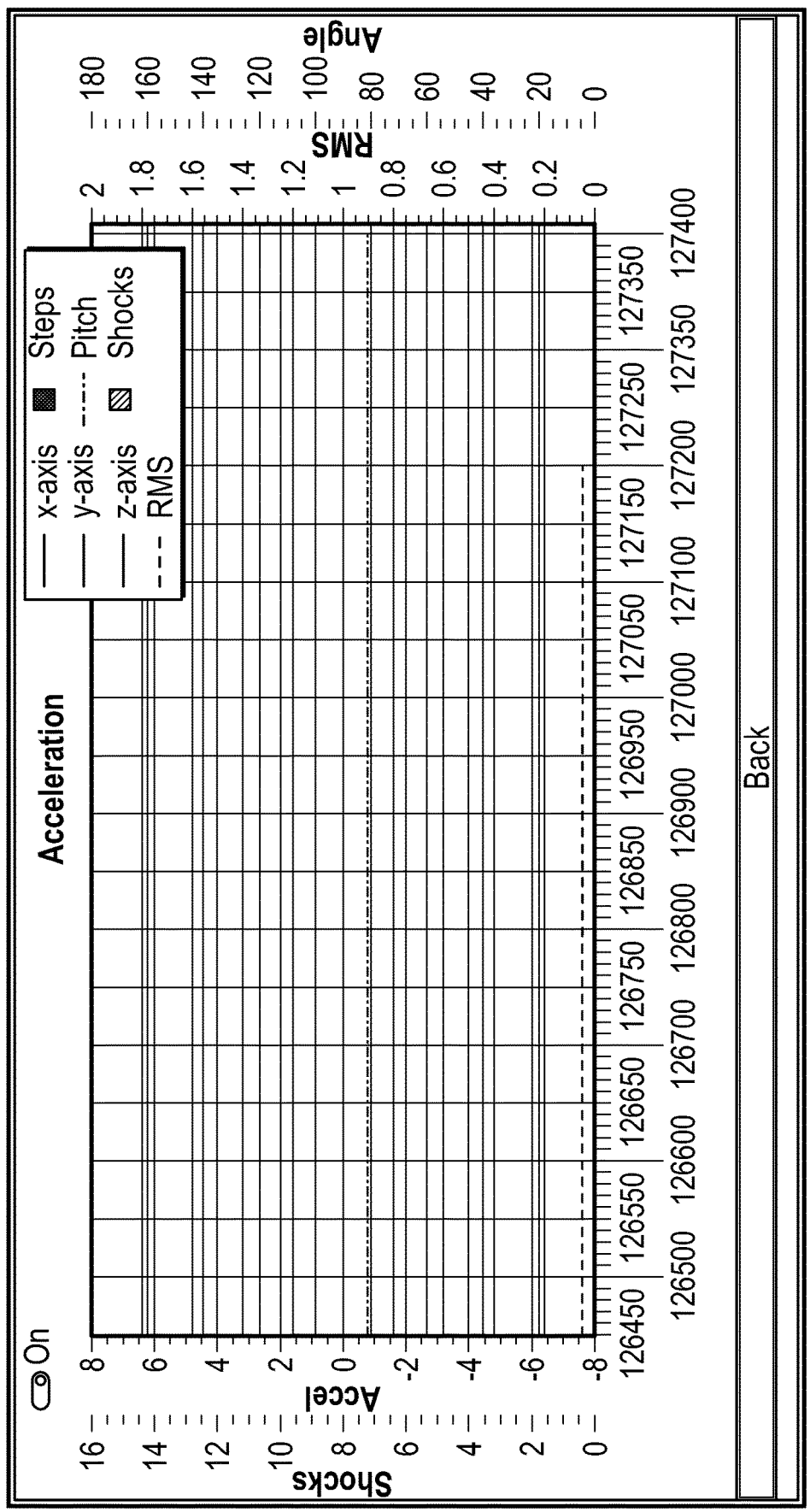
Figure 13I:
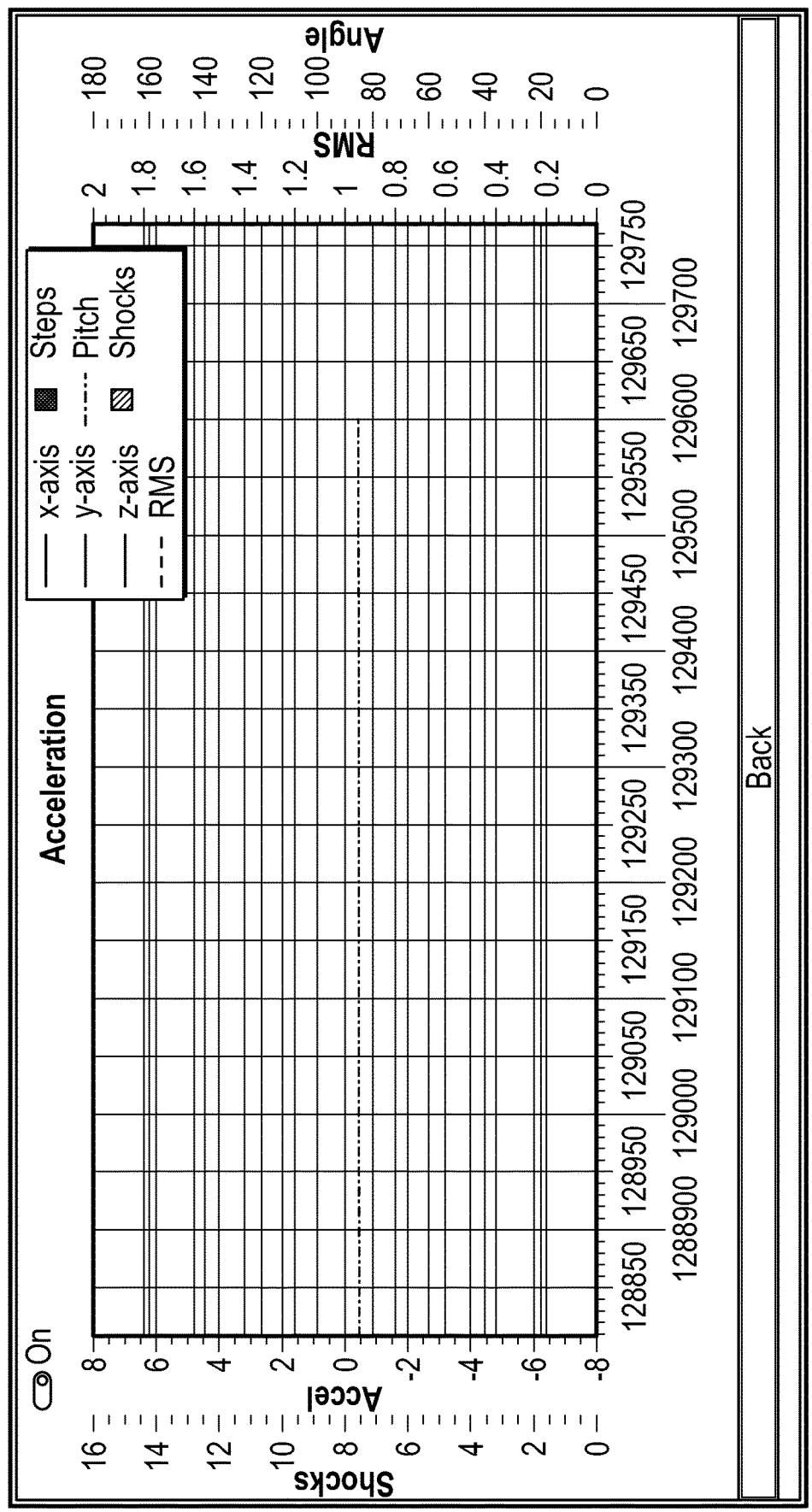
Figure 13J:
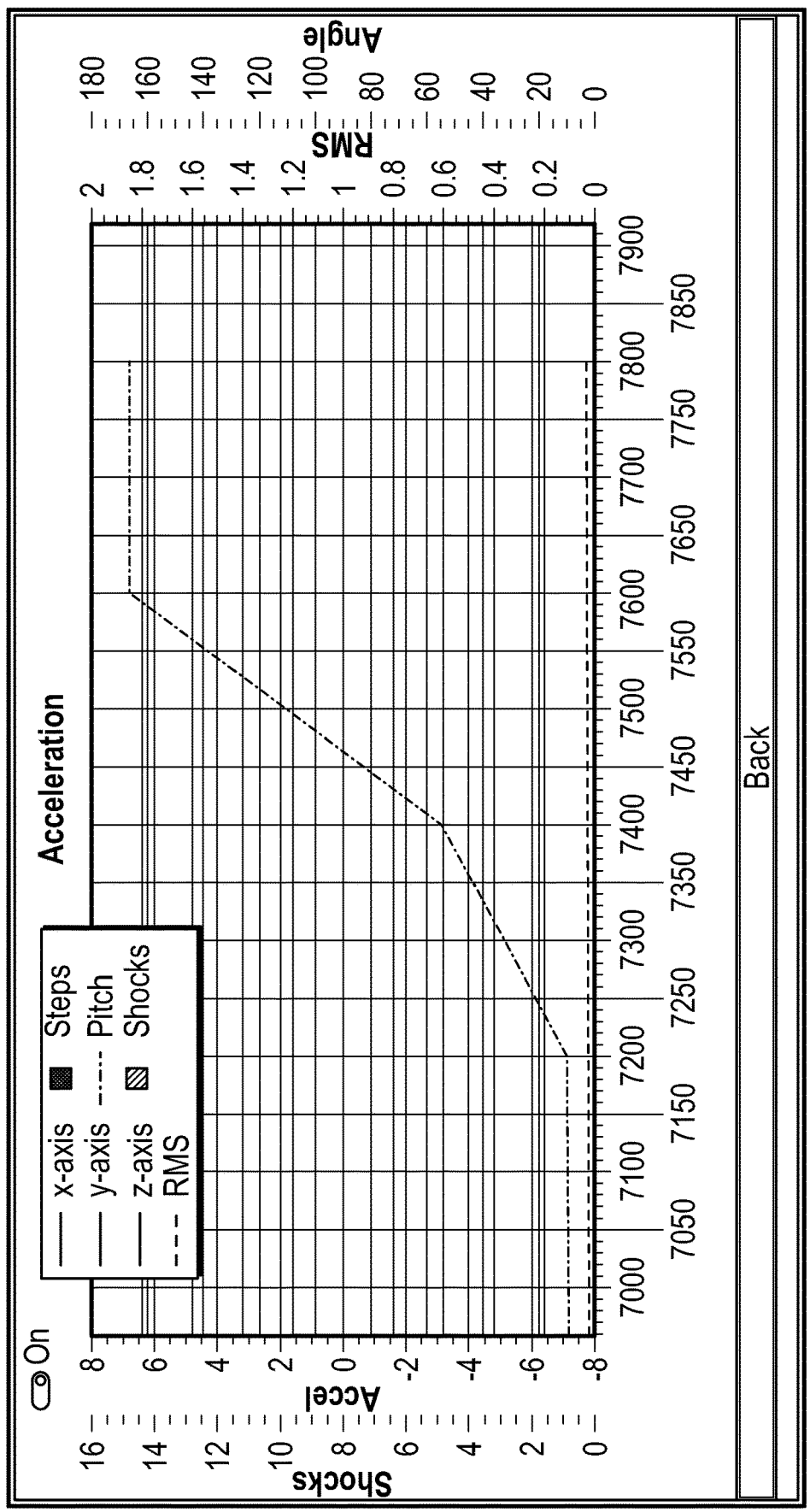

FIG. 13A illustrates a plot of motion data over time collected as the TNP apparatus was moved from a stand-up position to a laying-on-back position, and FIG. 13A shows a change in the pitch accordingly. FIG. 13B illustrates a plot of motion data over time collected as the TNP apparatus was swung back and forth. FIG. 13C illustrates a plot of motion data over time collected as the TNP apparatus was carried by a user while walking, and a timing of each of the user's step is also shown in FIG. 13C. FIG. 13D illustrates a plot of motion data over time collected when the TNP apparatus was positioned on an angled stand. FIG. 13E illustrates a plot of motion data over time collected as the TNP apparatus was dropped suddenly and, as shown in FIG. 13E, when a shock was detected. FIG. 13F illustrates a plot of motion data over time collected as the TNP apparatus was moved from an angled stand to a stand-up position. FIG. 13G illustrates a plot of motion data over time collected as the TNP apparatus was moved from a laying-on-back position to a laying-on-front position. FIG. 13H illustrates a plot of motion data over time collected when the TNP apparatus was laying on its left side. FIG. 13I illustrates a plot of motion data over time collected when the TNP apparatus was laying on its right side. FIG. 13J illustrates a plot of motion data over time collected as the TNP apparatus was moved from an upright position to an upside down position. As shown FIG. 13J, the pitch increased from almost 0° to 180°, indicating that the TNP apparatus was inverted.

As shown in FIGS. 13A-13J, the orientation of the TNP apparatus as well as movements of the TNP apparatus such as walking or shocks can be detected by the motion sensor. As discussed herein, determinations from motion data, such as the motion data plotted in FIGS. 13A-13J, may be used by a TNP apparatus to determine a cause of an error condition at the TNP apparatus or trigger an alarm, notification, or provide instructions, or the like.

Reduced Pressure Therapy Systems and Methods

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Various example embodiments and features related to methods and apparatuses for dressing and treating a wound with reduced pressure therapy or TNP therapy are described and/or contemplated within International Patent Application No. PCT/US2014/026692 (herein referred to as the '692 application), which published as WO 2014/151930, incorporated herein by reference in its entirety. The embodiments described below are compatible with and can be part of the embodiments described in the '692 Application, and some or all of the features described below can be used or otherwise combined with any of the features described in the '692 application.

In some embodiments, a TNP apparatus may contain network connection capabilities allowing the TNP apparatus to transmit data via a communications network, such as a cellular network. The communications network can, for instance, provide access to the Internet or additional device functionality to the TNP apparatus. The TNP apparatus may include security measures to prevent exposure to security risks associated with network connection capabilities. As such, the security measures may be incorporated into the TNP apparatus or the negative pressure therapy system in which the TNP apparatus communicates to limit exposure of the TNP apparatus or the negative pressure therapy system to security concerns.

Figure 14:
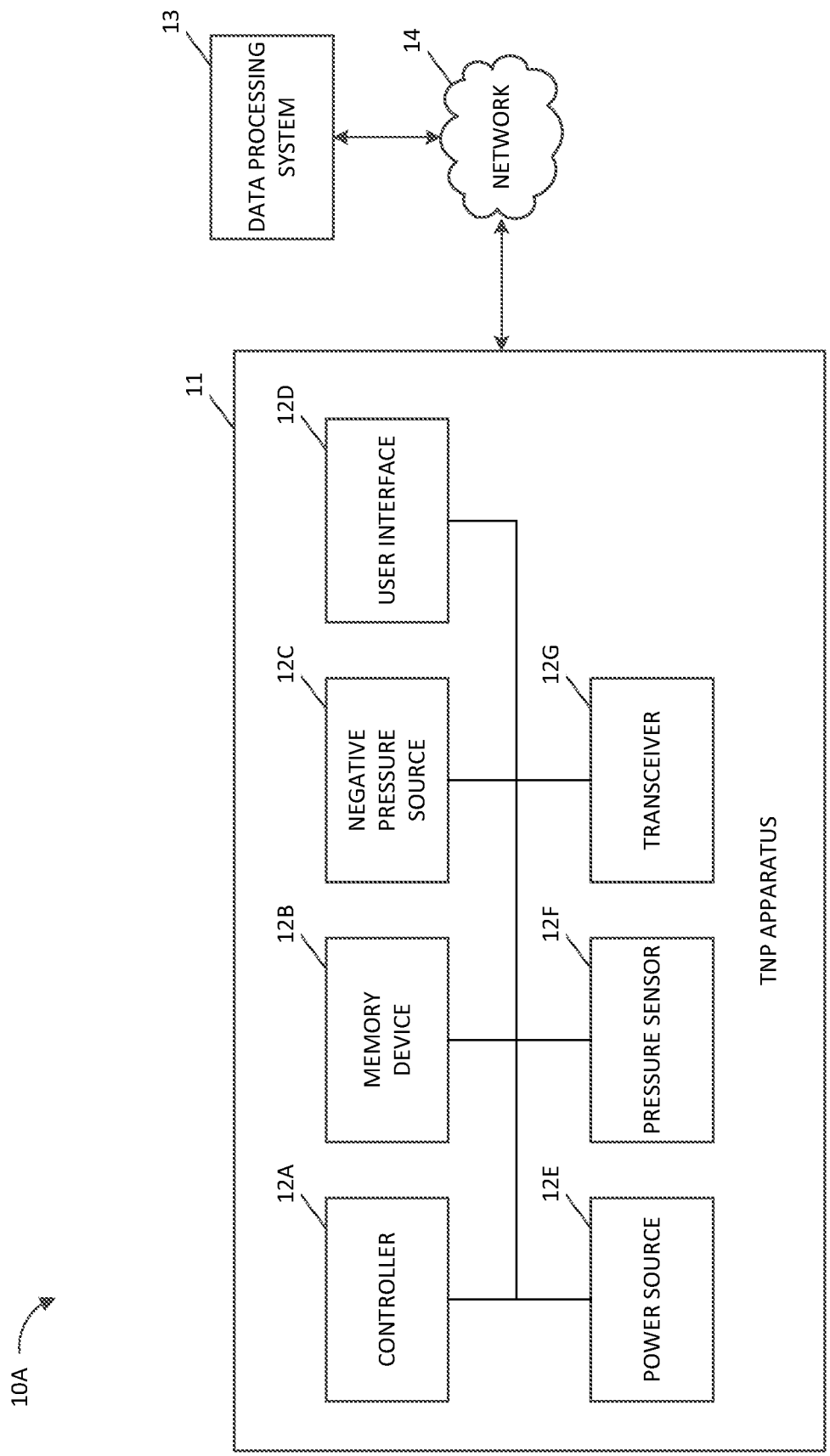
FIG. 14 illustrates a negative pressure therapy system according to some embodiments.

FIG. 14 illustrates a negative pressure therapy system 10A that includes a TNP apparatus 11 and a data processing system 13. The negative pressure therapy system 10A can be similar to any of the other negative pressure therapy systems described herein, such as the negative pressure therapy system 300A illustrated in FIG. 3A. The TNP apparatus 11 can be used to treat a wound using a wound dressing that is in fluidic communication with the TNP apparatus 11 via a fluid flow path. The TNP apparatus 11 can include a controller 12A, a memory device 12B, a negative pressure source 12C, a user interface 12D, a power source 12E, a pressure sensor 12F, and a transceiver 12G that are configured to electrically communicate with one another. The power source 12E can provide power to one or more components of the TNP apparatus 11. The TNP apparatus 11 can operate at the pressure levels and using control approaches similar to those described in the '692 Application, but may differ, at least in some instances, as described herein. In some implementations, the TNP apparatus 11 can configured the same as or similarly to the pump assembly 150 of FIG. 1, the pump assembly 230 of FIGS. 2A-F, or the pump assembly 1520 of FIG. 15 in the '692 application, and the data processing system 13 can be configured at least partially the same as or similarly to the remote computer 1540 of FIG. 15 in the '692 application.

The controller 12A can control operations of one or more other components of the TNP apparatus 11 according at least to instructions stored in the memory device 12B. The controller 12A can, for instance, control operations of and supply of negative pressure by the negative pressure source 12C. The negative pressure source 12C can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combinations of the foregoing. The user interface 12D can include one or more elements that receive user inputs or provide user outputs to a patient or caregiver. The one or more elements that receive user inputs can include buttons, switches, dials, touch screens, or the like.

The pressure sensor 12F can be used to monitor pressure underneath a wound dressing, such as (i) pressure in a fluid flow path connecting the negative pressure source 12C and the wound dressing as illustrated by FIG. 3B, (ii) pressure at the wound dressing as illustrated by FIG. 3C, or (iii) pressure at or in the negative pressure source 12C as illustrated by FIG. 3D. In some implementations, the pressure sensor 12F can include at least two pressure sensors that are positioned in or fluidically connected to the fluid flow path to permit differential measurement of the pressure, such as illustrated by FIG. 3E. For example, a first pressure sensor can be positioned upstream of the wound (such as at or near the inlet of the negative pressure source 12C) and a second pressure sensor can be positioned to detect pressure at or near the wound or at or near a canister. This configuration can be accomplished by incorporating, in addition to one or more lumens forming a first fluid flow path connecting the negative pressure source 12C to the wound, a second fluid flow path that includes one or more lumens connecting the TNP apparatus 11 to the wound and through which the second pressure sensor can monitor pressure at or near the wound or at or near a canister. The first and second fluid flow paths can be fluidically isolated from each other. When the at least two pressure sensors are used, the rate of change of pressure (for example, in peak-to-peak pressure or maximum pressure) in the first and second fluid flow paths can be determined and the difference in pressure detected between the first and second pressure sensors can be determined. These values can be used separately or together to detect various operational conditions, such as leaks, blockages, canister full, presence of blood in the first fluid flow path or the second fluid flow path, etc. In some implementations, multiple redundant pressure sensors can be provided to protect against failure of one or more of the pressure sensors.

The transceiver 12G can be used to communicate with the data processing system 13 via a network 14. The transceiver 12G can, for example, transmit device usage data like alarms, measured pressure, or changes to a therapy program administered by the TNP apparatus 11 to the data processing system 13. The network 14 can be a communication network, such as a wireless communications network like a cellular communications network. The memory device 12B can be used to store the device usage data that may be transmitted by the transceiver 12G. The data processing system 13 can, in some implementations, analyze pressure data received from the transceiver 12G to determine whether the received pressure data is indicative of the negative pressure source 12C being in use on a patient, such as using analysis approaches as described with respect to the TNP apparatus 11.

Network Connection Capabilities and Security

The TNP apparatus 11 may contain network connection capabilities, such as via the transceiver 12G, allowing the TNP apparatus 11 to transmit data via a communications network, such as a cellular network. The communications network can provide access to the Internet. In some instances, when a HTTP request is made from the TNP apparatus 11 to the data processing system 13, which can be a cloud service in some instances, the TNP apparatus 11 is temporarily assigned an IP address. The TNP apparatus 11 address IP may change for each request made by the TNP apparatus 11. In some instances, the TNP apparatus 11 may initiate communication with other devices and may not accept incoming requests from other devices, such as via the Internet.

Once the TNP apparatus 11 has established a connection interface, such as a cellular and TCP/IP backend, the TNP apparatus 11 may make various HTTP requests to the data processing system 13. For example, health or diagnostic information about the negative pressure therapy system 10A may be passed from or to the TNP apparatus 11 to the data processing system 13. Additionally, patient or therapy data may be transmitted from the TNP apparatus 11 to the data processing system 13. The data processing system 13 may respond with various responses based on processing of received data. In some instances, the various responses utilize a simple response including a minimalistic set of HTTP headers. The negative pressure therapy system 10A may not conduct extensive parsing of data processing system responses. For example, if the data processing system 13 responds with a HTTP 302 redirect, the TNP apparatus 11 may not follow the redirect message to a new URL.

The TNP apparatus 11 can be configured so that software updates may be performed via physical access to a USB or Serial port located on the TNP apparatus 11. Once physical access to the TNP apparatus 11 is established, technicians may utilize custom software to update a motor controller firmware and the apparatus interface software. In some instances, operating system and bootloader updates may be accomplished via a separate process which involves a case of the TNP apparatus 11 being fully opened. The operating system updates may utilize a different set of hardware targeted commercial software.

The software updates to the TNP apparatus 11 may use code signing. Code signing enables verification of the identity of the author of a particular piece of software and provide a means to help ensure the software has not been tampered. Enforcing code signing for uploaded firmware can ensure that software updates developed by the manufacturer of the TNP apparatus 11 may be loaded while software from other providers may not be loaded. Implementing code signing for the TNP apparatus 11 software can span multiple software development lifecycles.

In some instances, the manufacturer of the TNP apparatus 11 or the data processing system 13 may provide "known good" hashes to a third party validation service. Third party validation services can help detect tampered firmware or software during investigations or system inspections. Third party validation services can also provide a mechanism for third party integrity and forensics validation.

In some instances, a data processing system's uniform resource locators (URLs) may be limited to "https://." In alternative instances, the data processing system URL may be pointed to an arbitrary URL. However, allowing for arbitrary URLs to be passed to the negative pressure therapy system 10A components can allow for arbitrary code execution on the software executing the arbitrary URL.

The name and serial number assigned to the TNP apparatus 11 may be restricted to alphanumeric characters. To accomplish this, the TNP apparatus 11 or the data processing system 13 may incorporate validation checks which use alphanumeric characters for the TNP apparatus 11 serial number and name. Setting the serial number and name for the TNP apparatus 11 to alphanumeric characters can help to avoid security vulnerabilities that may be introduced if other external services assume that the serial number for the TNP apparatus 11 includes alphanumeric characters and consume a non-alphanumeric character value. In alternative instances, the name and serial number of the TNP apparatus 11 may not contain the alphanumeric character restriction.

The TNP apparatus 11 or the data processing system 13 may enforce transport encryption via transport layer security (TLS), for example https://, for data processing system connections. TLS can provide an encrypted tunnel for data to traverse through, thus providing protection against data tampering and data observation, confidentiality of data while in transit over the network, integrity verification of transmitted or received data, and endpoint verification. The Certificate Authority for the transport encryption certificate may be loaded on the TNP apparatus 11 and certificates may also be loaded on the data processing system 13.

The TNP apparatus 11 may be configured to so that its access to web server management consoles is restricted in some implementations. Access to web management interfaces may include access to the data processing system 13. Generally, users of the TNP apparatus 11 may not be expected to access web management interfaces. As such, the management interfaces can be disabled in some instances.

Connection to the data processing system 13 may utilize mutual authentication in some instances. Mutual authentication may prevent unauthorized entities from communicating with the data processing system 13. Additionally, if the TNP apparatus 11 is ever inadvertently connected to a communications networks, such as the Internet, and reachable via TCP/IP, mutual authentication may prevent an alternative device that is not associated with the TNP apparatus 11 or the data processing system 13 from interacting with the TNP apparatus 11 or the data processing system 13. A common form of mutual authentication is provided via certificates placed on both the TNP apparatus 11 and the data processing system 13. Traffic between the TNP apparatus 11 and the data processing system 13 may be "tunneled" through the established, secure connection provided by the mutual authentication. Generally, the mutual authentication can help ensure that systems developed by the manufacturer may communication with the data processing system 13 and not with other devices.

Mutual authentication can be established through the use of server and client certificates. To implement mutual authentication, transport encryption can first be in place, as discussed above. Once transport encryption is in place, client side authentication certificates (typically PKCS12) may be incorporated within the TNP apparatus 11 itself. The client side certificates can be created from the same Certificate Authority used by the transport encryption certificates. The TNP apparatus 11 may have a unique client side certificate, which allows the system's manufacturer to uniquely identify the TNP apparatus 11 when communicating to the data processing system 13. In some instances, a revocation mechanism may be in place to revoke tampered and stolen certificates which might be used to communicate with the data processing system 13.

A file firmware file uploaded to the TNP apparatus 11 may be a compressed representation of the system's file system. Once the compressed file is uploaded, the TNP apparatus 11 may reboot, decompress the file, check each file within the file system for changes, verify the files against a list of MD5 checksums, and then install the file to the appropriate location.

In some instances, several portions of the update process described herein may be circumvented by monitoring update files for path traversal issues, including files with directory traversal strings within the file name. For example, if a directory traversal string is included in a file name within the compressed firmware file, this file can be written to an arbitrary location on the TNP apparatus 11. This process may occur before validation of MD5 checksums occurs and may allow a remote user to place files in locations not normally allowed by a file system update.

The TNP apparatus 11 or the data processing system 13 can be configured to perform obfuscation of data. The TNP apparatus 11 or data processing system 13 may contain sensitive information (such as passwords, proprietary logic, or keys), and these values may be easily extracted from the TNP apparatus 11 without additional security measures. This can make it more difficult to reverse engineer and identify vulnerable segments of the software of the TNP apparatus 11 or the data processing system 13.

The TNP apparatus 11 may include anti-tamper mechanisms to prevent unauthorized personnel from accessing the internals associated with the TNP apparatus 11. These anti-tamper mechanisms can be tamper seals which can provide technicians with an indication that an unauthorized entity has tampered the TNP apparatus 11. Additional or alternative mechanisms can include the usage of technologies, such as eFuse, which separates sensitive device logic from traditional components and makes it difficult to extract information from the TNP apparatus 11. For example, anti-tamper mechanisms that may be incorporated into the TNP apparatus 11 include tamper proof security nuts, bolts, and fasteners; anti-tamper adhesive and seals; cutting or limiting debugging interfaces; antiFuse, and any combination thereof.

EXAMPLE EMBODIMENTS

1. An apparatus for applying negative pressure to a wound, comprising:
    a negative pressure source configured to provide negative pressure via a fluid flow path to a wound dressing; and
    a controller configured to:
    operate the negative pressure source to provide negative pressure to the wound dressing, and
    process data communicated via a computer network according to a security rule.
2. The apparatus of any one or more preceding embodiments, wherein the controller is configured to process the data according to the security rule so that access to the data provided by the controller via the computer network is limited to one or more authenticated devices.
3. The apparatus of any one or more preceding embodiments, wherein the controller is configured to receive the data according to the security rule so that the data is enabled to adjust a first function performable by the controller and prevented from adjusting a second function performable by the controller.
4. The apparatus of any one or more preceding embodiments, wherein the data comprises data indicative of operations of the negative pressure source or identification information for a user of the negative pressure source.
5. A method of operating, using, or manufacturing the apparatus of any preceding embodiment.

Other Variations

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy apparatus comprising:
   a housing;
   a sensor supported by the housing and configured to determine whether the housing is positioned in a moving transporter;
   a negative pressure source supported by the housing and configured to couple via a fluid flow path to a wound dressing covering a wound, the negative pressure source configured to provide negative pressure to the wound;
   a pressure sensor configured to detect pressure in the fluid flow path; and
   an electronic control circuitry supported by the housing and configured to operate the negative pressure source, the electronic control circuitry further configured to:
      responsive to a determination that the housing is positioned in the moving transporter based on the output of the sensor, cause the negative pressure wound therapy apparatus to operate in a first mode in which a threshold is decreased, thereby increasing sensitivity of a blockage alarm indicating a presence of blockage in the fluid flow path;
      responsive to a determination that the housing is not positioned in the moving transporter based on the output of the sensor, cause the negative pressure wound therapy apparatus to operate in a second mode in which the threshold is increase, thereby decreasing sensitivity of the blockage alarm;
      detect the presence of blockage in the fluid flow path based on comparing one or more peak-to-peak measurements of pressure in the fluid flow path measured by the pressure sensor to a threshold; and
      provide indication of the blockage alarm responsive to the detection of the presence of blockage in the fluid flow path.

2. The negative pressure wound therapy apparatus of claim 1, wherein the sensor configured to determine whether the housing is positioned in a moving transporter is configured to detect motion or vibration of the housing.

3. The negative pressure wound therapy apparatus of claim 1, wherein the sensor configured to produce the output usable to determine whether the housing is positioned in a moving transporter comprises a motion sensor, and wherein the electronic control circuitry is configured to determine that the housing is positioned in the moving transporter based on detecting that a movement pattern determined from the output of the motion sensor is indicative of the housing being positioned in the moving transporter.

4. The negative pressure wound therapy apparatus of claim 1, wherein the sensor configured to produce the output usable to determine whether the housing is positioned in a moving transporter comprises an audio sensor, and wherein the electronic control circuitry is configured to determine that the housing is positioned in the moving transporter based on detecting that noise or vibration determined from the output of the audio sensor satisfies a threshold indicative of the housing being positioned in the moving transporter.

5. The negative pressure wound therapy apparatus of claim 1, further comprising a sound generator, wherein the electronic control circuitry is further configured to:
   increase output level of the sound generator responsive to the determination that the housing is positioned in the moving transporter; and
   decrease output level of the sound generator responsive to a determination that the housing is not positioned in the moving transporter.

6. The negative pressure wound therapy apparatus of claim 1, wherein the moving transporter comprises an automobile, train, or airplane.

7. The negative pressure wound therapy apparatus of claim 1, wherein the pressure sensor is supported by the housing.

8. The negative pressure wound therapy apparatus of claim 1, further comprising a canister supported by the housing and configured to store fluid aspirated from the wound.

9. A kit comprising the negative pressure wound therapy apparatus of claim 1 and the wound dressing.

10. A method of controlling a negative pressure wound therapy apparatus, the method comprising:
    by an electronic control circuitry supported by a housing of the negative pressure wound therapy apparatus:
      causing provision of negative pressure wound therapy to a wound covered by a wound dressing;
      at a first time:
         determining that the housing is positioned in a moving transporter based on an output of a sensor; and
         responsive to determining that the housing is positioned in a moving transporter, causing the negative pressure wound therapy apparatus to operate in a first mode in which a threshold is decreased, thereby increasing sensitivity of a blockage alarm indicating a presence of blockage in a fluid flow path configured to connect the housing to a wound covered by a wound dressing:
      at a second time:
         determining that the housing is not positioned in the moving transporter based on the output of the sensor; and
         responsive to determining that the housing is not positioned in the moving transporter, causing the negative presssure wouud therapy apparatus to operate in a second mode in which the threshold is increased, thereby decreasing sensitivity of the blockage alarm;
      detecting the presence of blockage in a fluid flow path based on comparing one or more peak-to-peak measurements of pressure in the fluid flow path to the threshold; and
      providing indication of the blockage alarm responsive to detecting the presence of blockage in the fluid flow path.

11. The method of claim 10, wherein the sensor is configured to detect motion or vibration of the housing.

12. The method of claim 10, wherein the sensor comprises a motion sensor, and wherein the method comprises, by the electronic control circuitry, determining that the housing is positioned in the moving transporter based on detecting that a movement pattern determined from the output of the motion sensor is indicative of the housing being positioned in the moving transporter.

13. The method of claim 10, wherein the sensor comprises an audio sensor, and wherein the method comprises, by the electronic control circuitry, determining that the housing is positioned in the moving transporter based on detecting that noise or vibration determined from the output of the audio sensor satisfies a threshold indicative of the housing being positioned in the moving transporter.

14. The method of claim 10, further comprising, by the electronic control circuitry:
- at the first time, increasing output level of a sound generator of the negative pressure wound therapy apparatus responsive to determining that the housing is positioned in the moving transporter; and
- at the second time, decreasing output level of the sound generator responsive to determining that the housing is not positioned in the moving transporter.

15. The method of claim 10, wherein the moving transporter comprises an automobile, train, or airplane.

16. The negative pressure wound thereapy apparatus of claim 1, wherein the electronic control circuitry is further configured to, adjust operation of the negative pressure source responsive to the detection of the presence of blockage in the fluid flow path.

17. The method of claim 10, further comprising, adjusting provision of negative pressure wound therapy responsive to detecting the presence of blockage in the fluid flow path.

* * * * *

UNITED STATES PATENT AND TRADEMARK OFFICE
CERTIFICATE OF CORRECTION

PATENT NO. : 12,263,294 B2
APPLICATION NO. : 17/457647
DATED : April 1, 2025
INVENTOR(S) : Edward Yerbury Hartwell Page 1 of 2

It is certified that error appears in the above-identified patent and that said Letters Patent is hereby corrected as shown below:

On the Title Page

Column 2 Item (57) (Abstract), Line 8, delete "electronic controller circuitry" and insert -- electronic control circuitry --.

Column 2 Item (57) (Abstract), Line 11, delete "peak measurments of" and insert -- peak measurements of --.

In the Specification

Column 9, Line 28, delete "Renasys Aft and" and insert -- Renasys AB, and --.

Column 28, Line 15, delete "FIG. 131 illustrates" and insert -- FIG. 13I illustrates --.

In the Claims

Column 35, Line 5-6, Claim 1, delete "configured to determine" and insert -- configured to produce an output usable to determine --.

Column 35, Line 30 (approx.), Claim 1, delete "is increase, thereby" and insert -- is increased, thereby --.

Column 35, Line 36 (approx.), Claim 1, delete "to a threshold;" and insert -- to the threshold; --.

Column 35, Line 41, Claim 2, delete "configured to determine" and insert -- configured to produce the output usable to determine --.

Column 36, Line 34 (approx.), Claim 10, delete "wound dressing:" and insert -- wound dressing; --.

Signed and Sealed this
Third Day of June, 2025

Coke Morgan Stewart
*Acting Director of the United States Patent and Trademark Office*

Column 36, Line 41 (approx.), Claim 10, delete "negative presssure wouud therapy" and insert -- negative pressure wound therapy --.

Column 37, Line 12 (approx.), Claim 16, delete "wound thereapy apparatus" and insert -- wound therapy apparatus --.